(12) United States Patent
Miller et al.

(10) Patent No.: US 8,748,177 B2
(45) Date of Patent: Jun. 10, 2014

(54) COMPOSITIONS FOR PROLIFERATION OF CELLS AND RELATED METHODS

(75) Inventors: Freda Miller, Toronto (CA); David Kaplan, Toronto (CA); Kristen Smith, San Clemente, CA (US); Maryline Paris, Toronto (CA); Sibel Naska, Toronto (CA)

(73) Assignee: The Hospital for Sick Children, Toronto (CA)

( * ) Notice: Subject to any disclaimer, the term of this patent is extended or adjusted under 35 U.S.C. 154(b) by 146 days.

(21) Appl. No.: 13/075,647

(22) Filed: Mar. 30, 2011

(65) Prior Publication Data

US 2011/0301105 A1 Dec. 8, 2011

Related U.S. Application Data

(63) Continuation-in-part of application No. PCT/US2009/058723, filed on Sep. 29, 2009.

(60) Provisional application No. 61/101,443, filed on Sep. 30, 2008, provisional application No. 61/367,780, filed on Jul. 26, 2010, provisional application No. 61/426,160, filed on Dec. 22, 2010.

(51) Int. Cl.
*C12N 5/00* (2006.01)

(52) U.S. Cl.
USPC ........... 435/377; 435/375; 435/325; 424/93.7

(58) Field of Classification Search
None
See application file for complete search history.

(56) References Cited

U.S. PATENT DOCUMENTS

| | | | |
|---|---|---|---|
| 5,318,907 A | 6/1994 | Ronnett et al. | |
| 5,338,839 A | 8/1994 | McKay et al. | |
| 5,589,376 A | 12/1996 | Anderson et al. | |
| 5,633,426 A | 5/1997 | Namikawa et al. | |
| 5,654,183 A | 8/1997 | Anderson et al. | |
| 5,672,499 A | 9/1997 | Anderson et al. | |
| 5,691,327 A | 11/1997 | Blank | |
| 5,693,482 A | 12/1997 | Anderson et al. | |
| 5,733,727 A | 3/1998 | Field | |
| 5,753,506 A | 5/1998 | Johe | |
| 5,800,811 A | 9/1998 | Hall et al. | |
| 5,824,489 A | 10/1998 | Anderson et al. | |
| 5,849,553 A | 12/1998 | Anderson et al. | |
| 5,912,175 A | 6/1999 | Wille, Jr. | |
| 5,928,947 A | 7/1999 | Anderson et al. | |
| 5,942,225 A | 8/1999 | Bruder et al. | |
| 5,980,888 A * | 11/1999 | Dimoudis et al. | 424/93.7 |
| 6,001,654 A | 12/1999 | Anderson et al. | |
| 6,050,990 A | 4/2000 | Tankovich et al. | |
| 6,093,531 A | 7/2000 | Bjornson et al. | |
| 6,114,126 A * | 9/2000 | Schnaar et al. | 435/7.21 |
| 6,136,332 A | 10/2000 | Grollier et al. | |
| 6,153,388 A | 11/2000 | Reintgen | |
| 6,266,560 B1 * | 7/2001 | Zhang et al. | 604/20 |
| 6,299,900 B1 * | 10/2001 | Reed et al. | 424/449 |
| 6,497,872 B1 | 12/2002 | Weiss et al. | |
| 6,497,875 B1 | 12/2002 | Sorrell et al. | |
| 6,528,245 B2 | 3/2003 | Sanchez-Ramos et al. | |
| 6,787,355 B1 | 9/2004 | Miller et al. | |
| 6,835,567 B1 * | 12/2004 | Sah et al. | 435/377 |
| 6,969,608 B1 | 11/2005 | Miller et al. | |
| 7,105,571 B2 * | 9/2006 | Yeager et al. | 514/573 |
| 7,294,459 B1 | 11/2007 | Yang et al. | |
| 7,544,509 B2 | 6/2009 | Toma et al. | |
| 2002/0016002 A1 | 2/2002 | Toma et al. | |
| 2002/0123143 A1 | 9/2002 | Toma et al. | |
| 2003/0003572 A1 | 1/2003 | Anderson et al. | |
| 2003/0003574 A1 | 1/2003 | Toma et al. | |
| 2003/0077823 A1 | 4/2003 | Li et al. | |
| 2003/0175256 A1 | 9/2003 | Laurent-Applegate et al. | |
| 2004/0033597 A1 | 2/2004 | Toma et al. | |
| 2004/0110288 A1 | 6/2004 | Morrison et al. | |
| 2004/0115808 A1 | 6/2004 | Pachnis | |
| 2005/0089512 A1 * | 4/2005 | Schlotmann et al. | 424/93.7 |
| 2005/0214344 A1 | 9/2005 | Barrows et al. | |
| 2006/0088505 A1 | 4/2006 | Hoffmann et al. | |
| 2006/0149345 A1 * | 7/2006 | Boggs et al. | 607/118 |
| 2006/0263876 A1 | 11/2006 | Miller et al. | |
| 2007/0248574 A1 | 10/2007 | Miller et al. | |
| 2008/0038770 A1 | 2/2008 | Hansford et al. | |
| 2009/0053802 A1 | 2/2009 | Toma et al. | |
| 2009/0142834 A1 | 6/2009 | Toma et al. | |

FOREIGN PATENT DOCUMENTS

| | | |
|---|---|---|
| EP | 1950284 A1 | 7/2008 |
| WO | WO-01/53461 A1 | 7/2001 |
| WO | WO-03/010243 A2 | 2/2003 |

(Continued)

OTHER PUBLICATIONS

Koenig A et al. 1997. IFN-g-induced HLA-DR but not ICAM-1 expression on cultured dermal papilla cells is downregulated by TNF-a. Arch Dermatol Res 289: 466-470.*

Haider DG et al. 2005. PGE1 analog alprostadil induces VEGF and eNOS expression in endothelial cells. Am J Physiol Heart Circ Physiol 289: H2066-H2072.*

Cooper et al. 1988. The effects of prostaglandin E1 on megakaryocyte proliferation in vitro. Adv Exp Med Biol 241: 217-224. Abstract only.*

(Continued)

*Primary Examiner* — Lora E Barnhart Driscoll
(74) *Attorney, Agent, or Firm* — Clark & Elbing LLP

(57) ABSTRACT

We have discovered that p63 inhibition results in increased cellular proliferation. We have also performed a screen for agents capable of increasing cellular proliferation, (e.g., of stem cells such as skin-derived precursors (SKPs)). The invention therefore invention provides compositions, methods, and kits for increasing proliferation of cells, using compounds that decrease p63 expression or activity or using the compounds described herein. The invention also features methods of using these compounds for increasing hair growth, improving skin health, or promoting skin repair in a subject.

4 Claims, 28 Drawing Sheets

(56) References Cited

FOREIGN PATENT DOCUMENTS

| WO | WO-03/024406 A2 | 3/2003 |
|---|---|---|
| WO | WO-2004/108908 A1 | 12/2004 |
| WO | WO-2005/071063 A1 | 8/2005 |
| WO | WO-2008/148218 A1 | 12/2008 |
| WO | WO-2010/039679 A1 | 4/2010 |

OTHER PUBLICATIONS

Goodlad RA et al. 1989. Prostaglandins and the gastric epithelium: effects of misoprostol on gastric epithelial cell proliferation in the dog. Gut 30: 316-321.*
Kaneko F et al. 1995. Prostaglandin 11 analogues, SM-10902 and SM-10906, affect human keratinocytes and fibroblasts in vitro in a manner similar to PGEI: therapeutic potential for wound healing. Arch Dermatol Res 287: 539-545.*
Alonso et al., "Stem Cells of the Skin Epithelium," *Proc. Natl. Acad. Sci. USA* 100:11830-11835 (2003).
Anderson, "Molecular Control of Cell Fate in the Neural Crest: The Sympathoadrenal Lineage," *Annu. Rev. Neurosci.* 16:129-158 (1993).
Biernaskie et al., "Isolation of skin-derived precursors (SKPs) and differentiation and enrichment of Their Schwann Cell Progeny," *Nat. Protoc.* 1:2803-2812 (2006).
Cai et al., "Stem Cell and Precursor Cell Therapy," *Neuromol. Med.* 2:233-249 (2002).
Cao et al., "Stem Cell Repair of Central Nervous System Injury," *J. Neurosci. Res.* 68:501-510 (2002).
Chepko et al., "Ultrastructure of the Putative Stem Cell Niche in Rat Mammary Epithelium," *Tissue Cell.* 35:83-93 (2003).
Dupin et al., "The Neural Crest Stem Cells: Control of Neural Crest Cell Fate and Plasticity by Endothelin-3," *An. Acad. Bras. Cienc.* 73:533-545 (2001).
Fernandes et al., "A Dermal Niche for Multipotent Adult Skin-Derived Precursor Cells," Nature Cell Biology. 6(11):1082-1093 (2004).
Freshney, *Culture of Animal Cells: A Manual of Basic Technique*, New York: A.R. Liss, Inc. 215-225 (1987).
Gambardella et al., "The Multifaceted Adult Epidermal Stem Cell," *Curr. Opin. Cell Biol.* 15:771-777 (2003).
Huard et al., "Adult Olfactory Epithelium Contains Multipotent Progenitors That Give Rise to Neurons and Non-neural Cells," *J Comp Neurol.* 400:469-486 (1998).
Jahoda et al., "Hair Follicle Dermal Cells Differentiate into Adipogenic and Osteogenic Lineages," *Exp. Dermatol.* 12:849-859 (2003).
Jahoda et al., "Induction of Hair Growth by Implantation of Cultured Dermal Papilla Cells," *Nature* 311:560-562 (1984).
Kishimoto et al., "Selective Activation of the Versican Promoter by Epithelial-Mesenchymal Interactions during Hair Follicle Development", *Proc. Natl. Acad. Sci. USA* 96:7336-7341, (1999).
Kruger et al., "Neural Crest Stem Cells Persist in the Adult Gut but Undergo Changes in Self-renewal, Neuronal Subtype Potential, and Factor Responsiveness," *Neuron.* 35:657-669 (2002).
Kumamoto et al., "Hair Follicles Serve as Local Reservoirs of Skin Mast Cell Precursors," *Blood* 102:1654-1660 (2003).
Lako et al., "Hair Follicle Dermal Cells Repopulate the Mouse Haematopoietic System," *J. Cell Sci.* 115:3967-3974 (2002).
Lavker et al., "Hair Follicle Stem Cells," *J. Investig. Dermatol Symp. Proc.* 8:28-38 (2003).
Li et al.,"Nestin Expression in Hair Follicle Sheath Progenitor Cells," *Proc. Natl.Acad. Sci. USA* 100:9958-9961 (2003).
Lindvall et al., "Stem Cell Therapy for Human Neurodegenerative Disorders—How to Make it Work," *Nat. Med.* 10:S42-S50 (2004).
Lyle et al., "The C8/144B Monoclonal Antibody Recognizes Cytokeratin 15 and Defines the Location of Human Hair Follicle Stem Cells," *J. Cell Sci.* 111:3179-3188, (1998).
McElwee et al., "Cultured Peribulbar Dermal Sheath Cells Can Induce Hair Follicle Development and Contribute to the Dermal Sheath and Dermal Papilla," *J. Invest. Dermatol.* 121:1267-1275 (2003).
Morrison et al., "Prospective Identification, Isolation by Flow Cytometry, and in Vivo Self-renewal of Multipotent Mammalian Neural Crest Stem Cells," *Cell* 96:737-749 (1999).
Osada et al., "Characterization of Vibrissa Germinative Cells: Transition of Cell Types," *Exp. Dermatol.* 10:430-437 (2001).
Oshima et al., "Morphogenesis and Renewal of Hair Follicles from Adult Multipotent Stem Cells," *Cell* 104:233-245 (2001).
Ouji et al., "Promotion of Hair Follicle Development and Trichogenesis by Wnt-10b in Cultured Embryonic Skin and in Reconstituted Skin," *Biochem. Biophys. Res. Commun.* 345:581-587 (2006).
Oyelese et al., "Neural Trans-Differentiation of Plastic Adherent and Non-adherent Bone Marrow Stem Cells," *31st Annual Meeting of the Society for Neuroscience*, California (Abstract/Poster) (Nov. 10-15, 2001).
Pellegrini et al., "The Control of Epidermal Stem Cells (Holoclones) in the Treatment of Massive Full-Thickness Burns with Autologous Keratinocytes Cultured on Fibrin," *Transplantation* 68:868-879 (1999).
Peters et al., "Kit Is Expressed by Epithelial Cells In Vivo," *J. Invest. Dermatol.* 121:976-984 (2003).
Peters et al., "Migration of Melanoblasts into the Developing Murine Hair Follicle Is Accompanied by Transient c-Kit Expression," *J. Histochem. Cytochem.* 50:751-766 (2002).
Prouty et al., "Fibroblast-Dependent Induction of a Murine Skin Lesion with Similarity to Human Common Blue Nevus," *American Journal of Pathology* 148:1871-1885, 1996.
Rao, "Multipotent and Restricted Precursors in the Central Nervous System," *Anat. Rec. (New Anat.)* 257:137-148 (1999).
Rendl et al., "BMP Signaling in Dermal Papilla Cells Is Required for Their Hair Follicle-Inductive Properties," *Genes Dev.* 22:543-57, (2008).
Schouten et al., "A Review and Rationale for the Use of Cellular Transplantation as a Therapeutic Strategy for Traumatic Brain Injury," *J. Neurotrauma.* 21(11):1501-1538 (2004).
Shamblott et al., "Derivation of Pluripotent Stem Cells from Cultured Human Primordial Germ Cells," *Proc. Natl. Acad. Sci. USA* 95: 13726-13731 (1998).
Shamblott et al., "Human Embryonic Germ Cell Derivatives Express a Broad Range of Developmentally Distinct Markers and Proliferate Extensively In Vitro," *Proc. Natl. Acad. Sci. USA* 98: 113-118 (2001).
Stemple et al., "Isolation of a Stem Cell for Neurons and Glia from the Mammalian Neural Crest," *Cell* 71:973-985 (1992).
Tiede et al., "Hair Follicle Stem Cells: Walking the Maze," *Eur. J. Cell Biol.* 86: 355-376 (2007).
Toma et al., "Isolation of Multipotent Adult Stem Cells from the Dermis of Mammalian Skin," *Nat. Cell Biol.* 3:778-784 (2001).
Trempus et al., "Enrichment for Living Murine Keratinocytes from the Hair Follicle Bulge with the Cell Surface Marker CD34," *J. Invest. Dermatol.* 120:501-511 (2003).
Wu et al., "Hair Follicle Reformation Induced by Dermal Papilla Cells from Human Scalp Skin," *Arch. Dermatol. Res.* 298:183-190 (2006).
Zheng et al., "Organogenesis from Dissociated Cells: Generation of Mature Cycling Hair Follicles from Skin-Derived Cells," *J.Invest. Dermatol.* 124:867-876 (2005).

* cited by examiner

In vivo drug application: Hair length measurements

| Day 16 | Day 19 | Day 23 |
|---|---|---|
| Contr: 4205.36 μm | Contr: 6120.7μm | Contr: 6841.6μm |
| Lat150: 3885.6 μm | Lat150: 6002.3 μm | Lat150: 7181.7 μm |
| Alp: 4165.4 μm | Alp: 6139.4 μm | Alp: 7361.6 μm |
| Kae: 4 932.3 μm | Kae: 5870.8 μm | Kae: 7371.0 μm |
| MG624: 4176.1μm | MG624: 6115.4 μm | MG624: 7010.7 μm |
| Pram: 3837.0 μm | Pram: 5822.9 μm | Pram: 7128.2 μm |
| AKTi: 4068.9 μm | AKTi: 6210.0 μm | AKTi: 6998.5μm |
| GoldBond: 3550.4μm | GoldBond: 5500.2μm | GoldBond: 6811.0μm |

Fig. 16

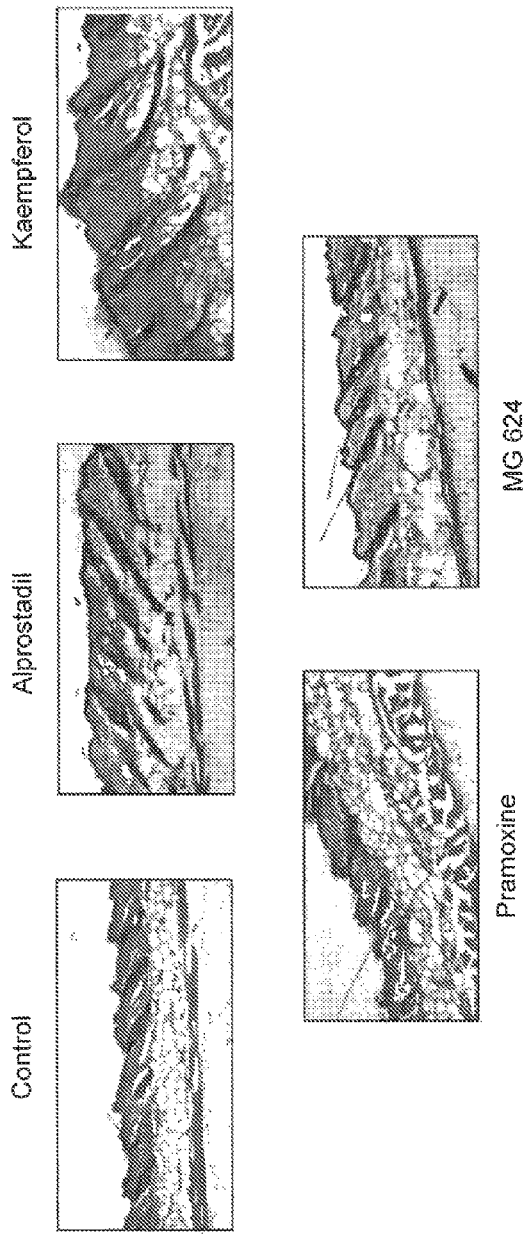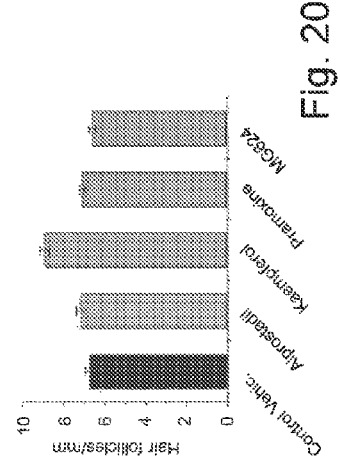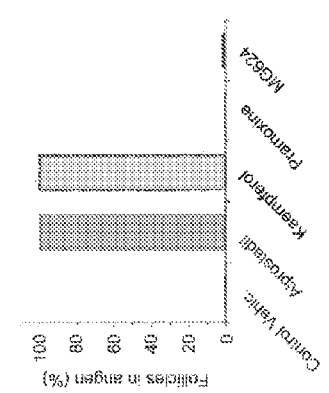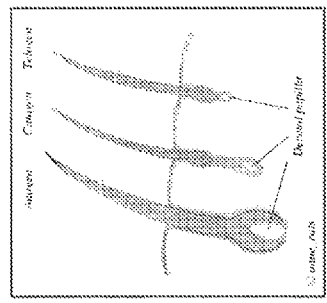
Fig. 20

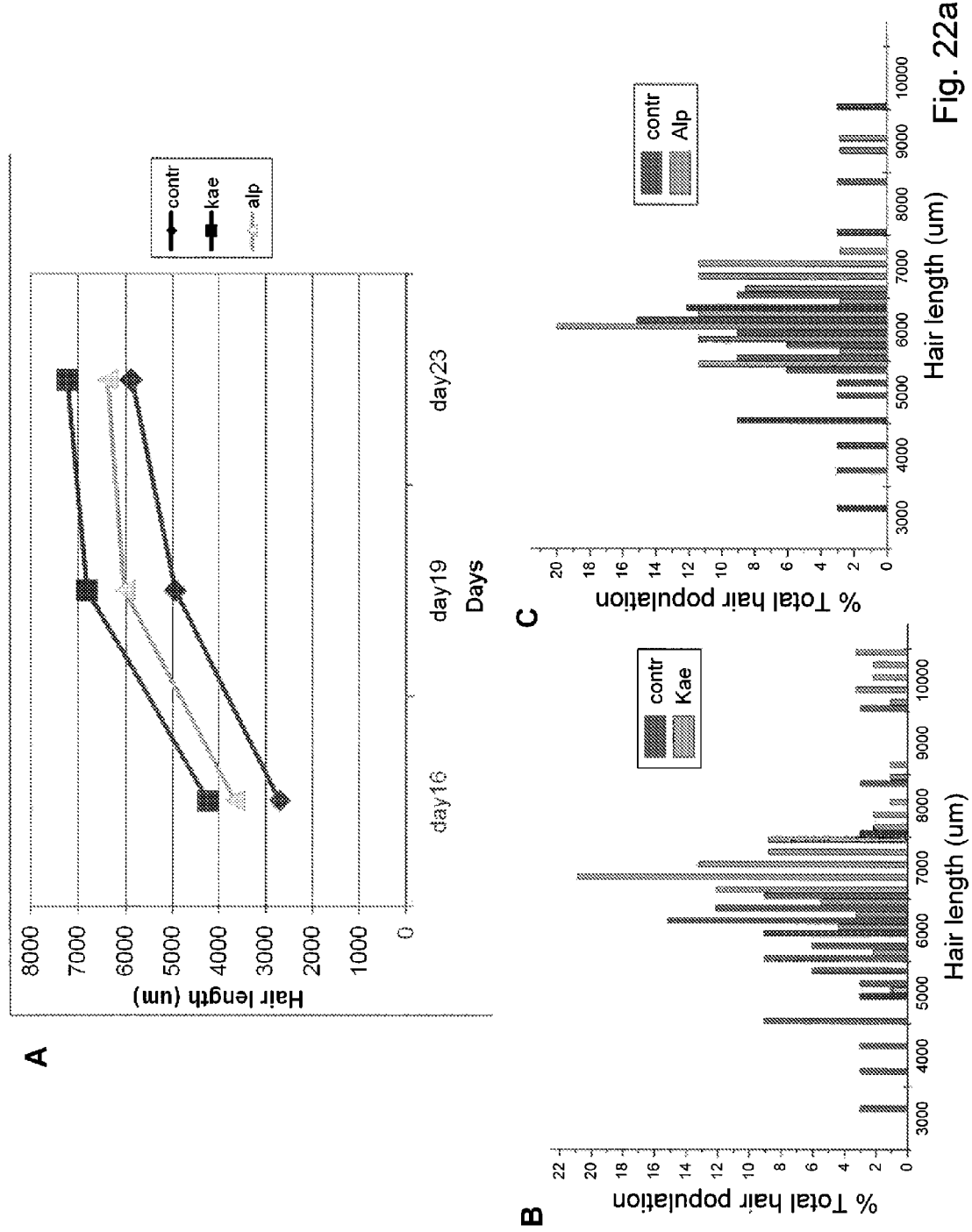
Fig. 22a-c

COMPOSITIONS FOR PROLIFERATION OF CELLS AND RELATED METHODS

CROSS-REFERENCE TO RELATED APPLICATIONS

This application is a continuation-in-part of International Application No. PCT/US2009/058723, filed Sep. 29, 2009, which, in turn, claims the benefit of U.S. Provisional Application No. 61/101,443, filed Sep. 30, 2008. This application also claims the benefit of U.S. Provisional Application Nos. 61/367,780, filed Jul. 26, 2010, and 61/426,160, filed Dec. 22, 2010. Each of these applications is hereby incorporated by reference.

BACKGROUND OF THE INVENTION

The invention relates to compositions and methods useful in the proliferation of cells, particularly stem cells such as skin-derived precursors (SKPs). Also provided are methods for treating a subject having a disease or condition where an increase in SKP proliferation is desired.

Expensive growth factors are often required for cell proliferation, and even then, expansion is often not optimal. Thus, molecules which replace or enhance the actions of growth factors and allow increased expansion of cells in culture are desirable.

In addition, there are inadequate methods for regenerating skin or inducing hair growth in a subject (e.g., for treatment of a disease or condition where regenerating skin or inducing hair growth is beneficial).

Thus, there is a need for molecules that promote the proliferation and self-renewal of cells such as SKPs. These molecules may be highly advantageous for cosmetic and medical purposes.

SUMMARY OF THE INVENTION

We have discovered that p63 inhibits proliferation of skin-derived precursors (SKPs) and, further have screened for and identified compounds that increase proliferation of SKPs and neuroblastoma cells. On the basis of these discoveries, the invention features methods and compositions useful for increasing cell proliferation, as well as methods for increasing SKP proliferation in subject (e.g., for treating diseases and conditions where increased SKP proliferation is desired).

Accordingly, in a first aspect, the invention features a method of increasing proliferation of a cell (e.g., cultured in vitro). The method includes contacting the cell with a sufficient amount of one or more of a compound that decreases (e.g., selectively decreases) p63 expression or activity or a compound selected from the group consisting of acyclovir, alprostadil, aristolochic acid, carbadox, chlorpyrifos, cyclocreatine, 7,4'-dimethoxyisoflavone, dorzolamide, S(−)eticlopride, evoxine, guaifenesin, hydroxyprogesterone, kaempferol, linamarin, mexicanolide, MG 624, pramoxine, tannic acid, targinine, alpha-methyllycacontine, mecamylamine hexamethonium, alsterpaullone, and yohimbic acid, or an analog thereof, under conditions that support cell proliferation. The cell may be from a tumor cell line, may be a stem cell (e.g., a SKP), or any cell described herein capable of proliferation. The cell may be a human or non-human cell (e.g., from a mammal such as a mouse or rat). In certain embodiments, the compound is a p63 antibody, or an antigen-binding fragment thereof; an RNAi molecule that decreases p63 expression, or a nucleic acid encoding the RNAi molecule; or a polypeptide substantially identical to a dominant negative form of p63, a fragment thereof, or a nucleic acid encoding such a polypeptide, where the polypeptide or the fragment has dominant negative p63 activity. In particular embodiments, the compounds are (a) alprostadil and kaempferol or (b) alprostadil and pramoxine. In embodiments where the cell is cultured in vitro, the culture may include at least one additional growth factor (e.g., FGF2, EGF, NGF, or a combination thereof). The method may involve no substantial change in the differentiation rate of the cells.

In another aspect, the invention features a composition including (a) an isolated cell (e.g., a stem cell such as a SKP, or any cell described herein) and (b) one or more compounds selected from the group consisting of acyclovir, alprostadil, aristolochic acid, carbadox, chlorpyrifos, cyclocreatine, 7,4'-dimethoxyisoflavone, dorzolamide, S(−)eticlopride, evoxine, guaifenesin, hydroxyprogesterone, kaempferol, linamarin, mexicanolide, MG 624, pramoxine, tannic acid, targinine, alpha-methyllycacontine, mecamylamine hexamethonium, alsterpaullone, and yohimbic acid, or an analog thereof, where the compound is present in an amount sufficient to promote proliferation of the stem cell. In particular embodiments, the compounds are (a) alprostadil and kaempferol or (b) alprostadil and pramoxine.

In another aspect, the invention features a composition including (a) an isolated cell (e.g., a stem cell such as a SKP, or any cell described herein) and (b) one or more compounds that decreases p63 expression or activity, where the compound is present in an amount sufficient to promote proliferation of the cell. In particular embodiments, the compounds are (a) alprostadil and kaempferol or (b) alprostadil and pramoxine.

In either of the above two aspects, the composition may further include a growth factor (e.g., FGF2, EGF, NGF, or a combination thereof). The composition may be capable of supporting cell proliferation.

In another aspect, the invention features a kit including (a) one or more compounds that decreases p63 expression or activity (e.g., any described herein) or one or more compounds selected from the group consisting of acyclovir, alprostadil, aristolochic acid, carbadox, chlorpyrifos, cyclocreatine, 7,4'-dimethoxyisoflavone, dorzolamide, S(−)eticlopride, evoxine, guaifenesin, hydroxyprogesterone, kaempferol, linamarin, mexicanolide, MG 624, pramoxine, tannic acid, targinine, alpha-methyllycacontine, mecamylamine hexamethonium, alsterpaullone, and yohimbic acid, or an analog thereof; and (b) instructions for use of (a) to promote cell proliferation, hair growth, skin repair, or skin health. In particular embodiments, the compounds are (a) alprostadil and kaempferol or (b) alprostadil and pramoxine.

In another aspect, the invention features a composition including (a) one or more compounds that decreases p63 expression or activity (e.g., any described herein) or one or more compounds selected from the group consisting of acyclovir, alprostadil, aristolochic acid, carbadox, chlorpyrifos, cyclocreatine, 7,4'-dimethoxyisoflavone, dorzolamide, S(−)eticlopride, evoxine, guaifenesin, hydroxyprogesterone, kaempferol, linamarin, mexicanolide, MG 624, pramoxine, tannic acid, targinine, and yohimbic acid, or an analog thereof, and (b) a topically suitable excipient. The composition may be in the form of a cream or a lotion (e.g., a moisturizing lotion). In particular embodiments, the compounds are (a) alprostadil and kaempferol or (b) alprostadil and pramoxine.

In another aspect, the invention features a method of increasing SKP proliferation in a subject. The method includes administering to the subject a sufficient amount of (a) one or more compounds that inhibits p63 expression or activity; or (b) one or more compounds selected from the group consisting of acyclovir, alprostadil, aristolochic acid, carbadox, chlorpyrifos, cyclocreatine, 7,4'-dimethoxyisoflavone, dorzolamide, S(−)eticlopride, evoxine, guaifenesin, hydroxyprogesterone, kaempferol, linamarin, mexicanolide, MG 624, pramoxine, tannic acid, targinine, alpha-methyllycacontine, mecamylamine hexamethonium, alsterpaullone, and yohimbic acid, or an analog thereof. The compound can be administered topically, systemically, or by any route described herein. In certain embodiments, the compound that inhibits p63 expression or activity is a p63 antibody or an antigen-binding fragment thereof; an RNAi molecule that inhibits p63 expression or a nucleic acid encoding the RNAi molecule; or a polypeptide substantially identical to a dominant negative form of p63, a fragment thereof, or a nucleic acid encoding such a polypeptide, where the polypeptide or the fragment has dominant negative p63 activity. In particular embodiments, the compounds are (a) alprostadil and kaempferol or (b) alprostadil and pramoxine.

In another aspect, the invention features a method of promoting hair growth in a subject. The method includes administering to the subject a sufficient amount of (a) one or more compounds that inhibits p63 expression or activity or (b) one or more compounds selected from the group consisting of acyclovir, alprostadil, aristolochic acid, carbadox, chlorpyrifos, cyclocreatine, 7,4'-dimethoxyisoflavone, dorzolamide, S(−)eticlopride, evoxine, guaifenesin, hydroxyprogesterone, kaempferol, linamarin, mexicanolide, MG 624, pramoxine, tannic acid, targinine, alpha-methyllycacontine, mecamylamine hexamethonium, alsterpaullone, and yohimbic acid, or an analog thereof. The compound may be administered topically, systemically, or by any route described herein. In certain embodiments, the compound that inhibits p63 expression or activity may be a p63 antibody or an antigen-binding fragment thereof; an RNAi molecule that inhibits p63 expression or a nucleic acid encoding the RNAi molecule; or a polypeptide substantially identical to a dominant negative form of p63, a fragment thereof, or a nucleic acid encoding the polypeptide, where the polypeptide or the fragment has dominant negative p63 activity. In particular embodiments, the compounds are (a) alprostadil and kaempferol or (b) alprostadil and pramoxine.

In another embodiment, the invention features a method of repairing skin in a subject, the method including administering a sufficient amount of (a) one or more compounds that inhibits p63 expression or activity or (b) one or more compounds selected from the group consisting of acyclovir, alprostadil, aristolochic acid, carbadox, chlorpyrifos, cyclocreatine, 7,4'-dimethoxyisoflavone, dorzolamide, S(−)eticlopride, evoxine, guaifenesin, hydroxyprogesterone, kaempferol, linamarin, mexicanolide, MG 624, pramoxine, tannic acid, targinine, alpha-methyllycacontine, mecamylamine hexamethonium, alsterpaullone, and yohimbic acid, or an analog thereof. In certain embodiments, the subject has a wound, and the compound is administered in an amount sufficient to improve healing of the wound. The compound may be administered topically, systemically, or by any route described herein. In certain embodiments, the compound that inhibits p63 expression or activity is a p63 antibody or an antigen-binding fragment thereof; an RNAi molecule that inhibits p63 expression or a nucleic acid encoding the RNAi molecule; or a polypeptide substantially identical to a dominant negative form of p63, a fragment thereof, or a nucleic acid encoding such a polypeptide, where the polypeptide or the fragment has dominant negative p63 activity. In particular embodiments, the compounds are (a) alprostadil and kaempferol or (b) alprostadil and pramoxine.

In another aspect, the invention features a method of improving skin health in a subject for example, by reducing skin aging (or the appearance of aging) or reducing wrinkles. The method includes administering to the subject a sufficient amount of (a) one or more compounds that inhibits p63 expression or activity or (b) one or more compounds selected from the group consisting of acyclovir, alprostadil, aristolochic acid, carbadox, chlorpyrifos, cyclocreatine, 7,4'-dimethoxyisoflavone, dorzolamide, S(−)eticlopride, evoxine, guaifenesin, hydroxyprogesterone, kaempferol, linamarin, mexicanolide, MG 624, pramoxine, tannic acid, targinine, alpha-methyllycacontine, mecamylamine hexamethonium, alsterpaullone, and yohimbic acid, or an analog thereof. The compound may be administered topically, systemically, or by any route described herein. In certain embodiments, the compound that inhibits p63 expression or activity is a p63 antibody or an antigen-binding fragment thereof; an RNAi molecule that inhibits p63 expression or a nucleic acid encoding the RNAi molecule; or a polypeptide substantially identical to a dominant negative form of p63, a fragment thereof, or a nucleic acid encoding the polypeptide, where the polypeptide or the fragment has dominant negative p63 activity. In particular embodiments, the compounds are (a) alprostadil and kaempferol or (b) alprostadil and pramoxine.

In any of the above methods, the subject may be a human.

In another aspect, the invention features a method of identifying a compound capable of altering cell proliferation, the method including (a) contacting (e.g., in vitro) a SKP (e.g., human or non-human SKP, such as a mouse or rat SKP) with a candidate compound, and (b) determining the proliferation rate of the SKP, where an alteration in the proliferation rate of the SKP in the presence of the compound as compared to in the absence of the compound, indicates that the compound alters the rate of cell proliferation. In certain embodiments, the compound is selected from a chemical library.

In embodiments of the above aspects of the invention where the subject is administered acyclovir or analog thereof, the subject may not suffer from, or be diagnosed with, herpes (e.g., genital herpes) or chicken pox. In embodiments where the subject is administered alprostadil or an analog thereof, the subject may not suffer from, or be diagnosed with erectile dysfunction or be in need of weight loss (e.g., be overweight or obese). In embodiments where the subject is administered aristolochic acid or an analog thereof, the subject may not be in need of weight loss (e.g., be overweight or obese). In embodiments where the subject is administered dorzolamide or an analog thereof, the subject may not have, or may not be diagnosed with, increased intraocular pressure (e.g., ocular hypertension or open-angle glaucoma). In embodiments where the subject is administered guaifenesin or an analog thereof, the subject may not be in need of an expectorant (e.g., suffering from a cold, an allergy, or airway infection). In embodiments where the subject is administered hydroxyprogesterone, the subject may not be suffering from, or may not be diagnosed with, congenital adrenal hyperplasia, 21-hydroxylase deficiency, or breast neoplasms, or is not at risk of having a preterm birth. In embodiments where the subject is administered pramoxine, the subject may not be in need of a topical anesthetic (e.g., due to itching, burning, or other pain). In embodiments where the subject is administered yohimbic acid, the subject may not be suffering from erectile dysfunction, panic disorder, alcoholism, or depression.

In any of the above aspects, the SKP may express any one, two, three, four, five, or more of the markers for SKPs described herein, or may not express any one, two three, four, five, or more of the markers not expressed by SKPs. In any of the above aspects, the analogs of the compounds may be any analog described herein.

By "decreasing expression" of a gene or protein is meant reducing (e.g., by 5%, 10%, 25%, 50%, 75%, 90%, 95%, 99%, or 99.9%) in the amount the gene or protein produced. Decreased expression may occur, for example, by a reduction in transcription, translation, or mRNA processing.

By "decreased activity" is meant a reduction (e.g., by 5%, 10%, 25%, 50%, 75%, 90%, 95%, 99%, or 99.9%) by in the total activity of a protein in a cell. Reduction of activity may result, for example, from direct inhibition of the protein (e.g., by a compound that specifically binds the protein), increased degradation or processing, or decreased expression of the protein.

By a compound or composition that "selectively inhibits" a target protein (e.g., p63) is meant a compound or composition that decreases expression or activity of the target protein and (a) binds specifically to the target protein (e.g., a small molecule or an antibody) and decreases its activity, (b) binds specifically to an mRNA encoding the target protein, thereby decreasing expression of the protein, or (c) prevents the target protein from performing its normal function (e.g., by binding to a binding partner of the target protein).

A compound which "specifically binds" a target molecule is a compound which recognizes and binds the target, but which does not substantially recognize and bind other molecules.

By "subject" is meant a human or non-human animal (e.g., a mammal).

By a cell which does "not express" a protein or gene is meant that expression of the protein or gene cannot be detected by standard methods. In the case of cell surface markers, expression can be measured by flow cytometry, using a cut-off value as obtained from negative controls (i.e., cells known to lack the antigen of interest) or by isotype controls (i.e., measuring non-specific binding of the antibody to the cell). Thus, a cell that "does not express" a marker appears similar to the negative control for that marker. For gene expression, a gene "does not express" if the presence of its mRNA cannot be visually detected on a standard agarose gel following standard PCR protocols.

A nucleic acid molecule or polypeptide is said to be "substantially identical" to a reference molecule if it exhibits, over its entire length, at least 50% or 55% identity, preferably at least 60%, 65%, or 70% identity, more preferably at least 75% or 85% identity, and most preferably at least 90%, 95%, or 99% identity to the sequence of the reference molecule. For polypeptides, the length of comparison sequences is at least 16 amino acids, preferably at least 20 amino acids, more preferably at least 25 amino acids, and most preferably at least 35 amino acids. For nucleic acid molecules, the length of comparison sequences is at least 50 nucleotides, preferably at least 60 nucleotides, more preferably at least 75 nucleotides, and most preferably at least 110 nucleotides.

The term "antibody" is used in the broadest sense and specifically covers, for example, single monoclonal antibodies against p63, antibody compositions with polyepitopic specificity, single chain antibodies, nanobodies, and fragments of antibodies. "Antibody" includes intact immunoglobulin or antibody molecules, polyclonal antibodies, multispecific antibodies (e.g., bispecific antibodies formed from at least two intact antibodies), and immunoglobulin fragments (such as Fab, F(ab')$_2$, or Fv), so long as they exhibit any of the desired properties (e.g., antigen binding) described herein.

"Antibody fragments" comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

"Humanized" forms of non-human (e.g., murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin.

A "human antibody" is one which possesses an amino acid sequence which corresponds to that of an antibody produced by a human and/or has been made using any of the techniques for making human antibodies known in the art. A "human antibody" includes antibodies comprising at least one human heavy chain polypeptide or at least one human light chain polypeptide.

By "small molecule" is meant a molecule having a molecular weight of less than about 1000 Da (e.g., less than 900, 800, 700, 600, 500, or 400 Da).

Compounds useful in the invention include those described herein in any of their pharmaceutically acceptable forms, including isomers such as diastereomers and enantiomers, salts, esters, amides, thioesters, solvates, and polymorphs thereof, as well as racemic mixtures and pure isomers of the compounds described herein. As an example, by "alprostadil" is meant the free base as well as any pharmaceutically acceptable salt thereof.

The term "pharmaceutically acceptable salt" represents those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, isethionate, lactobionate, lactate, laurate, lauryl sulfate, malate, maleate, malonate, mesylate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-12}$ heteroalkyl, for example, includes from 1 to 12 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 12 ring carbon atoms, inclusive. Exemplary cyclic groups include cyclopropyl, cyclobutyl, cyclopentyl, and cyclohexyl groups.

By "$C_{1-4}$ alkyl" is meant a branched or unbranched hydrocarbon group having from 1 to 4 carbon atoms. A $C_{1-4}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxy groups. $C_{1-4}$ alkyls include, without limitation, methyl, ethyl, n-propyl, isopropyl, cyclopropyl, cyclopropylmethyl, n-butyl, iso-butyl, sec-butyl, tert-butyl, and cyclobutyl.

By "$C_{2-4}$ alkenyl" is meant a branched or unbranched hydrocarbon group containing one or more double bonds and having from 2 to 4 carbon atoms. A $C_{2-4}$ alkenyl may optionally include monocyclic or polycyclic rings, in which each ring desirably has from three to six members. The $C_{2-4}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-4}$ alkenyls include, without limitation, vinyl, allyl, 2-cyclopropyl-1-ethenyl, 1-propenyl, 1-butenyl, 2-butenyl, 3-butenyl, 2-methyl-1-propenyl, and 2-methyl-2-propenyl.

By "$C_{2-4}$ alkynyl" is meant a branched or unbranched hydrocarbon group containing one or more triple bonds and having from 2 to 4 carbon atoms. A $C_{2-4}$ alkynyl may optionally include monocyclic, bicyclic, or tricyclic rings, in which each ring desirably has five or six members. The $C_{2-4}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-4}$ alkynyls include, without limitation, ethynyl, 1-propynyl, 2-propynyl, 1-butynyl, 2-butynyl, and 3-butynyl.

By "$C_{2-6}$ heterocyclyl" is meant a stable 5- to 7-membered monocyclic or 7- to 14-membered bicyclic heterocyclic ring which is saturated, partially unsaturated, or unsaturated (aromatic), and which consists of 2 to 6 carbon atoms and 1, 2, 3, or 4 heteroatoms independently selected from N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated $\pi$ electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 3 to 10 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3, or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, hydroxyalkyl, carboxyalkyl, and carboxyl groups. Examples of $C_{1-7}$ heteroalkyls include, without limitation, methoxymethyl and ethoxyethyl.

By "halide" or "halogen" is meant bromine, chlorine, iodine, or fluorine.

By "fluoroalkyl" is meant an alkyl group that is substituted with a fluorine atom.

By "perfluoroalkyl" is meant an alkyl group consisting of only carbon and fluorine atoms.

By "carboxyalkyl" is meant a chemical moiety with the formula —(R)—COOH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^+$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl, heteroalkyl, heteroaryl, and/or aryl groups, resulting in a positive charge at the nitrogen atom.

Other features and advantages of the invention will be apparent from the following Detailed Description, the drawings, and the claims.

BRIEF DESCRIPTION OF THE DRAWINGS

FIG. 16 is a table showing that topical application of certain compounds promotes hair growth. Mice were treated topically with the indicated compounds. At specific time points, approximately 30-40 hairs were plucked from each mouse and their length was measured. Three mice were used to test each compound.

FIG. 20 is a series of photomicrographs and graphs showing topical application of certain compounds induces anagen hair cycle and follicle density. Skin samples were also analysed for density and morphology of hair follicles. The density is expressed as number of follicles per mm whereas the anagen hair follicles are determined by morphology.

FIGS. 22A-22C are graphs showing the effect of in vivo hair growth on topical treatment with either kaempferol or alprostadil. FIG. 22A shows the length of hair in mice treated with either kaempferol, alprostadil, or a vehicle control at days 16, 19, and 23. FIGS. 22B and 22C show the hair length distribution on day 23 from mice treated with either kaempferol or alprostadil as compared to control mice.

DETAILED DESCRIPTION

Figure 1A:
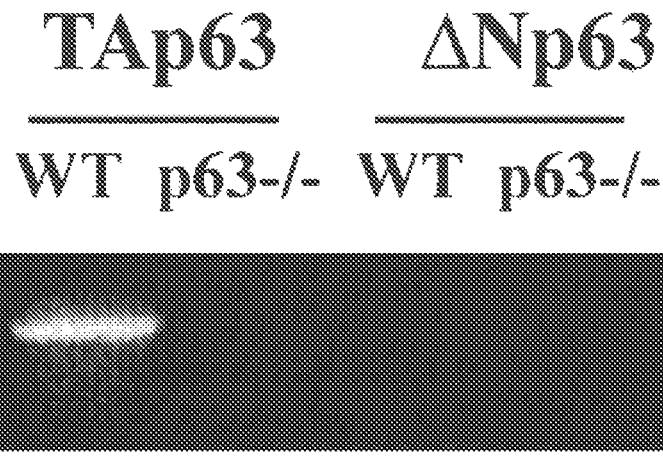
FIG. 1A is a photograph of a gel showing that wild-type SKPs express TAp63 mRNA, whereas SKPs from p63 null mice do not.

We have discovered that the p63 pathway is involved in inhibition of proliferation of skin-derived precursors (SKPs). The invention thus features methods of increasing proliferation of a cell (e.g., a stem cell such as a SKP) by inhibiting p63 expression or activity.

In addition, we have performed a screen to identify agents useful for enhancing cellular proliferation. This screen resulted in identification compounds including acyclovir, alprostadil, aristolochic acid, carbadox, chlorpyrifos, cyclocreatine, 7,4'-dimethoxyisoflavone, dorzolamide, S(−)eticlopride, evoxine, guaifenesin, hydroxyprogesterone, kaempferol, linamarin, mexicanolide, MG 624, pramoxine, tannic acid, targinine, and yohimbic acid. On this basis, these compounds, or analogs of these compounds, can be used to increase proliferation of cells, including SKPs or neuroblastoma cells. As SKPs are known to be involved in skin regeneration and hair growth, stimulation of SKPs using these compounds can enhance skin repair (e.g., wounded skin), improve dermal maintenance or skin health, or promote hair growth in a subject.

Cells

The compounds identified herein may be used to increase proliferation of any cell that is capable of proliferation, such as tumor cell lines (e.g., neuroblastoma) or stem cells. In certain embodiments, the cell is a stem cell such as a SKP cell. Other stem cells include embryonic stem cells and adult stem cells such as mesenchymal cells and hematopoietic stem cells.

SKPs are described in U.S. Patent Application Publication Nos. 2004/0033597 and 2007/0248574. SKPs can express at least one, two, three, or more of the following molecular markers: nestin, WNT-1, vimentin, versican, fibronectin, S100β, slug, snail, twist, Pax3, Sox9, Dermo-1, and Sox2. SKPs may also express increased levels of slug, snail, twist, and Pax3 relative to central nervous system neural stem cells. Desirably, the multipotent stem cells of the invention do not express measurable levels of at least one, two, three, or more of the following molecular markers: tyrosinase, c-kit, tryp-1, and DCT, which are markers of melanoblasts and melanocytes. The multipotent stem cells also may not express of one or more of the following markers of Schwann cells: MBP, P0, p75NTR, and Sox10.

SKPs are capable of differentiating into various non-neural cells (e.g., hair follicle cell, bone cell, smooth muscle cell, or adipocyte) and neural cells (e.g., a neuron, astrocyte, Schwann cell, or oligodendrocyte).

SKPs can be isolated as described in the art. In one example, dorsal or facial skin from mouse embryos (E15-19), mouse or rat neonates (P2-P6), or adults (3 weeks and older) was dissected from the animal and cut into 2-3 mm$^2$ pieces.

Tissue was digested with 0.1% trypsin for 10-45 min at 37° C., mechanically dissociated and filtered through a 40 μm cell strainer (Falcon).

Cell Culture

The cells (e.g., SKPs) may be cultured under standard cell culture conditions, such as those described herein or known in the art. In one example, SKPs are cultured as described in Toma et al. (Nat. Cell Biol. 3:778-784, 2001). Dissociated cells (e.g., as described above) were pelleted and plated in DMEM-F12, 3:1 (Invitrogen), containing 20 ng/ml EGF and 40 ng/ml FGF2 (both from Collaborative Research), hereafter referred to as proliferation medium. Cells were cultured in 25 $cm^2$ tissue culture flasks (Falcon) in a 37° C., 5% $CO_2$ tissue culture incubator. SKPs were passaged by mechanically dissociating spheres and splitting 1:3 with 75% new medium and 25% conditioned medium from the initial flask. For neuronal differentiation, SKP spheres or primary dissociated skin cells were mechanically dissociated and plated on chamber slides (Nunc) coated with poly-D-lysine/laminin in DMEM-F12 3:1 supplemented with 40 ng/ml FGF2 and 10% FBS (Bio-Whittaker) for 5-7 days. Cells were then cultured an additional 5-7 days in the same medium without FGF2 but with the addition of 10 ng/ml NGF (Cedar Lane), 10 ng/ml BDNF (Peprotech), and 10 ng/ml NT3 (Peprotech). For Schwann cell differentiation, dissociated spheres were cultured in DMEM-F12 3:1 supplemented with 10% FBS for 7 days, then switched to the same medium supplemented with 4 μM forskolin (Sigma).

Compounds that Decrease p63 Expression or Activity

The compositions, methods, and kits of the invention may employ a compound that decreases p63 expression or activity. These compounds can be used either in place of or in addition to other growth factors (e.g., FGF2 or EGF). In certain embodiments, the addition of a compound that decreases p63 expression or activity allows for the use of a reduced concentration of another growth factor or factors (e.g., FGF2 or EGF). Exemplary compounds include RNAi molecules that target p63 mRNA, antibodies that specifically bind p63, and dominant negative forms of p63.

p63 RNAi Molecules

RNAi molecules such as siRNA molecules that target p63 are known in the art or can be designed and tested for RNA interference activity. p63 RNAi molecules are commercially available (e.g., from Santa Cruz Biotechnology, Inc., Santa Cruz, Calif., Catalog No. sc-36161). Additional RNAi molecules (e.g., siRNA molecules) can be designed based on the human p63 mRNA sequence (NCBI accession Nos. NM_003722, NM_001114978, NM_001114979, NM_001114980, NM_001114981, and NM_001114982) or the corresponding mouse (NCBI accession Nos. NM_011641, NM_001127259, NM_001127260, NM_001127261, NM_001127262, NM_001127263, NM_001127264, NM_001127265) or rat (NCBI accession Nos. NM_001127339, NM_001127341, NM_001127342, NM_001127343, NM_001127344, and NM_019221) sequences.

p63 Antibodies

Anti-p63 antibodies may be employed in the compositions, methods, and kits of the invention. Any antibody or antibody variant (e.g., monoclonal, polyclonal, human, humanized, single chain), a fragment thereof, or a nanobody can be employed.

Such antibodies are commercially available (e.g., from Abcam, Inc., Cambridge, Mass., Catalog No. ab735, or from Santa Cruz Biotechnology, Inc., Catalog No. sc-8431). Additional antibodies (polyclonal or monoclonal) against p63 or regions of p63 can also be generated using methods known in the art.

Humanized antibodies can be generated following the method of Winter and co-workers (Jones et al., Nature, 321: 522-525, 1986; Riechmann et al., Nature, 332:323-327 (1988); Verhoeyen et al., Science, 239:1534-1536 (1988)), by substituting rodent CDRs or CDR sequences for the corresponding sequences of a human antibody.

Accordingly, such "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human monoclonal antibodies can be made by the hybridoma method, as is known in the art (see, e.g., Kozbor, J. Immunol. 133, 3001, 1984, and Brodeur et al., Monoclonal Antibody Production Techniques and Applications, pp. 51-63 (Marcel Dekker, Inc., New York, 1987)).

Nanobodies can be generated by immunization of an animal (e.g., a camel or llama) which produces nanobodies, which can then be purified using standard techniques.

Single chain Fv fragments may be produced such as described in Iliades et al., FEBS Letters, 409:437-441 (1997). Coupling of such single chain fragments using various linkers is described in Kortt et al., Protein Engineering, 10:423-433 (1997).

The compositions, methods, and kits of the invention can also include a p63 antibody fragment (e.g., a fragment of a murine, human or humanized antibody, and antibody variants). Such fragments can be derived by proteolytic digestion of intact antibodies (see, e.g., Morimoto et al., J. Biochem. Biophys. Methods 24:107-117 (1992) and Brennan et al., Science 229:81, 1985) or can be produced directly by recombinant host cells. For example, Fab'-SH fragments can be directly recovered from E. coli and chemically coupled to form $F(ab')_2$ fragments (Carter et al., Bio/Technology 10:163-167, 1992). Single chain Fv fragments may be produced such as described in Iliades et al., FEBS Letters, 409: 437-441 (1997). Coupling of such single chain fragments using various linkers is described in Kortt et al., Protein Engineering, 10:423-433, 1997.

Triabodies can also be used in the compositions, methods, and kits of the invention. Such antibodies are described for instance in Iliades et al., supra and Kortt et al., supra.

The antibodies of the present invention may be modified by conjugating the antibody to an agent (e.g., any of the compounds described herein). Further antibody modifications are also contemplated. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington: *The Science and Practice of Pharmacy,* 20th edition, 2000, ed. A. R. Gennaro, Lippincott Williams & Wilkins, Philadelphia. To increase the serum half-life of the antibody, one may incorporate a salvage receptor binding epitope into the antibody (especially an antibody fragment), as described in U.S. Pat. No. 5,739,277, for example. A "salvage receptor binding epitope" is an epitope of the Fc region of an IgG molecule (e.g., IgG1, IgG2, IgG3, or IgG4) that is responsible for increasing the in vivo serum half-life of the IgG molecule.

Dominant Negative p63

Dominant negative forms of p63, polypeptides substantially identical to such dominant negative forms and having dominant negative activity, or fragments thereof having dominant negative activity can be used in the compositions, methods, and kits of the invention. Forms of p63 with the N-terminal transactivation domain are termed TAp63, whereas those lacking this domain (ΔN-p63 isoforms) have dominant negative activity. See, e.g., Ghioni et al., Mol Cell Biol 22:8659-8668, 2002. Exemplary sequences encoding dominant negative proteins are known in the art and include DN p63 alpha (NCBI accession Nos. AAG45610 and AAC62636 (human); AAP87985 and AAC62644 (mouse)); DN p63 beta (NCBI accession Nos. AAG45611 and AAC62638 (human); AAP87986 and AAC62643 (mouse)); and DN p63 gamma (NCBI accession Nos. AAG45612 and AAC62634 (human); AAP87987 and AAC62642 (mouse)). Other dominant negative p63 polypeptides can sequences substantially identical to those sequences, or may contain chemical modifications, as is known in the art.

Gene Therapy

Decreases in p63 expression or activity may also be achieved through introduction of a gene vector into a subject. To increase cellular proliferation, enhance skin repair or skin health, or promote hair growth, p63 expression or activity may be decreased, for example, by administering to a subject a vector containing a polynucleotide sequence encoding a dominant negative form of p63 or an RNAi molecule that targets p63 mRNA, operably linked to a promoter capable of driving expression in targeted cells. Any standard gene therapy vector and methodology may be employed for such administration.

Compounds

Based on the results of the screen described herein, we have identified compounds capable of increasing proliferation. Accordingly, these compounds, or analogs of these compounds, may be used in methods for increasing proliferation (e.g., without affecting differentiation) in vivo or in vitro of any type of cell capable of proliferation (e.g., stem cells, such as SKPs). The compounds may be used in conjunction with any cell culture techniques known in the art. Use of these compounds may allow for reduced concentrations of other growth factors. In addition, the compounds can also be used to treat a disease or condition where increases in SKP proliferation are desirable (e.g., those described herein).

Acyclovir

The compositions, methods, and kits of the invention may include acyclovir or an analog thereof. Acyclovir has the structure:

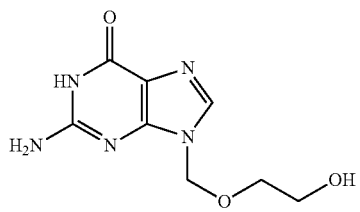 [SMILES: Nc1nc2c(ncn2COCCO)c(=O)[nH]1]

Analogs of acyclovir are described in U.S. Pat. No. 4,199,574 and have the structure:

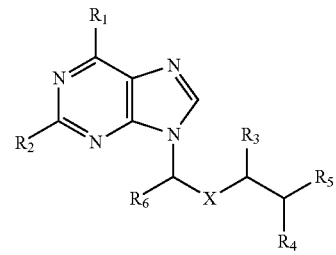

where X is sulfur or oxygen, $R_1$ is H, halogen, OH, $C_{1-4}$ alkoxy, azide, thio, $C_{1-6}$ alkylthio, amino, $C_{1-6}$ alkylamino or dialkylamino; $R_2$ is H, halogen, $C_{1-4}$ alkylthio, acylamino, amino or azide; $R_3$ is H, straight or branch chain or cyclic $C_{1-6}$ alkyl, $C_{1-6}$ hydroxyalkyl, benzyloxyalkyl, or phenyl; $R_4$ is H, OH, or alky; $R_5$ is H, OH, $NH_2$, $C_{1-4}$ alkyl, $C_{1-4}$ hydroxyalkyl, benzyloxy, benzoyloxy, benzoyloxymethyl, sulfamoyloxy, phosphate carboxypropiamyloxy, straight chain or cyclic acyloxy having from 1 to 8 carbon atoms e.g., acetoxy or substituted carbamoyl group of formula NH.CO—Z wherein Z is alkyl, aryl or aralkyl optionally substituted by one or more of sulfonyl, amino, carbamoyl or halogen; $R_6$ is H or alkyl (e.g., when X is O and $R_2$, $R_3$, $R_4$, and $R_6$ are H, $R_1$ is not amino or methylamino when $R_5$ is hydrogen or hydroxy), or a salt thereof.

Other analogs of acyclovir include 1-O-hexadecylpropanediol-3-p-acyclovir, 1-O-hexadecylpropanediol-3-phosphoacyclovir, 1-O-octadecyl-sn-glycero-3-phosphoacyclovir, 2'-O-glycyl acyclovir, 2,6-diamino-9-(2-hydroxyethoxymethyl)purine, 3,9-dihydro-3-((2-hydroxyethoxy)methyl)-6-ethyl-9-oxo-5H-imidazo(1,2-a) purine, 3-methyl-cyclosal-PCVMP, 6-deoxypenciclovir, 8-fluoropenciclovir, 9-((1,3-dihydroxy-2-propylthio)methyl)guanine, 9-((2-aminoethoxy)methyl)guanine, 9-(2'-(9"-octadecenoyloxy)ethoxymethyl)guanine, 9-(3,4-dihydroxybutyl)guanine, 9-(4-hydroxy-2-(hydroxymethyl)butyl)-guanine triphosphate, 9-(4-hydroxybutyl)guanine, acyclovir β-glucoside, acyclovir diphosphate dimyristoylglycerol, acyclovir fluorophosphate, acyclovir monophosphate, acyclovir monophosphate-lactosaminated serum albumin conjugate, acyclovir phosphite, acyclovir triphosphate, acyclovir-5'-(phenyl methoxy alaninyl)phosphate, BIOLF 143, bis(2-(guanin-9-ylmethoxy)ethoxy)-4-(methylsulfonyl)phenyl phosphate, BRL 42359, bucyclovir triphosphate, desciclovir, diamminechloro(9-(2-hydroxyethoxymethyl)guan-7-yl) platinum(II), famciclovir, γ-glutamylacyclovir, ganciclovir, guanin-9-yl methyloxy-2-ethyl bis(S-acetyl-2-thioethyl) phosphate, guanin-9-yl methyloxy-2-ethyl bis(S-pivaloyl-2-thioethyl)phosphate, penciclovir, penciclovir triphosphate, tyrosylacyclovir, val-valacyclovir, and valacyclovir.

Additional analogs are described in U.S. Pat. Nos. 4,806,642, 4,957,924, 5,580,571, 6,214,811, and 6,031,096.

Prostaglandins

The compositions, methods, and kits of the invention may include a prostaglandin such as alprostadil (prostaglandin E1), or an analog thereof. Alprostadil has the formula:

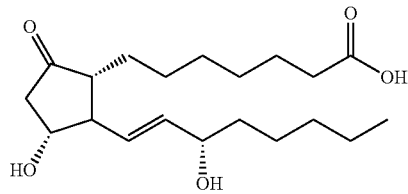 [SMILES: CCCCC[C@H](O)/C=C/C1[C@H](O)CC(=O)[C@@H]1CCCCCCC(=O)O]

Analogs of alprostadil are described in U.S. Pat. No. 3,735,005 and have the formula:

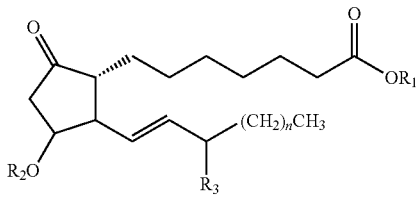

where $R_1$ is hydrogen or a $C_{1-8}$ alkyl group, $R_2$ is a member selected from the group consisting of H, $C_{1-8}$ alkyl, and the acyl group of a hydrocarbon carboxylic acid of 2 to 18 carbon atoms; $R_3$ is OH, n is 3, 4, or 5, and $OR_2$ and $R_3$ may have an α or β configuration. Exemplary of lower alkyl containing from 1 to 8 carbon atoms suitable for include branched or straight chain hydrocarbon groups such as methyl, ethyl, propyl, isopropyl, butyl, tert-butyl, pentyl, and hexyl. Exemplary acyl groups include acetyl, propionyl, butyryl, hexanoyl, octanoyl, lauroyl, palmitoyl, stearoyl, and oleoyl. Other alprostadil analogs are described in U.S. Pat. No. 5,219,885. Other prostaglandins that can be used in the invention are described below.

Other prostaglandins include 2-chloro-4-hydroxy-5-(6-methoxycarbonyl-2-hexyenylidene)-4-n-octyl-2-cyclopentanone, 4-fluoroenisoprost, 7-hydroxy-5,11-dioxotetranor-prostane-1,16-dioic acid, AY 22093, bromovulone III, carijenone, claviridenone E, claviridenone F, claviridenone G, clavubicyclone, MR 256, NEPP11 compound, NEPP6 compound, NEPP6-biotin, prostaglandin endoperoxides, prostaglandins A, prostaglandins B, prostaglandins D, prostaglandins E, prostaglandins F, prostaglandins I (e.g., epoprostenol), RS 61756-007, S 1033, tricycloclavulone.

Prostaglandins A include 13,14-dihydro-15-deoxy-Δ-prostaglandin-A1-methyl ester, 13,14-dihydro-Δ7-prostaglandin A1 methyl ester, 15-keto-13,14-dihydroprostaglandin A2, 16,16-dimethylprostaglandin A2 methyl ester, 5-(4-N,N-dimethylaminophenylmethylene)-4-hydroxy-2-(1-methylimidazol-2-ylthio)-4-(4-phenylbutyl)-2-cyclopentenone, 8-isoprostaglandin A2, chlorovulone I, clavulone II, clavulones, prostaglandin A1, prostaglandin A2, prostaglandin A2 isopropyl ester, and TEI 3313.

Prostaglandins B include 15-ketoprostaglandin B1, 16,16-dimethyl-15-dehydroprostaglandin B1 trimer, 19-hydroxyprostaglandin B2, di-Calciphor, OC 5181, OC 5186, prostaglandin B1, prostaglandin B2, and prostaglandin Bx.

Prostaglandins D include 9-chloro-15-cyclohexyl-11,15-dihydroxypentanor-5,13-prostadienoic acid, 9-fluoro-15-cyclohexyl-11,15-dihydroxypentanor-5,13-prostadienoic acid, 9-fluoro-15-hydroxy-16-phenoxy-17,18,19,20-tetranor-5,13-prostadienoic acid, 9-hydroxy-11,15-dioxo-2,3,18,19-tetranorprost-5-ene-1,20-dioic acid, prostaglandin D2, and prostaglandin D3.

Prostaglandin D2 analogs include 11,15-dioxo-9-hydroxy-2,3,4,5-tetranorprostan-1,20-dioic acid, 11-methoxime prostaglandin D2, 11-methyleneprostaglandin D2, 13,14-dihydro-15-ketoprostaglandin D2, 15-deoxy-Δ(12,14)-prostaglandin J2, 15-deoxyprostaglandin J2, 15-methylprostaglandin D2, 9-deoxy-9,10-didehydro-12,13-didehydro-13,14-dihydroprostaglandin D2, 9-deoxy-Δ-9-prostaglandin D2, anhydrolevulgandin D2, Δ(12)-prostaglandin J(2), prostaglandin D2 4-azidophenacyl ester, prostaglandin D2 methyl ester, and TS-002.

Prostaglandins E include 17-isolevuglandin E4, 6(9)-oxy-11,15-dihydroxy-prosta-7,13-dienoic acid, anhydrolevuglandin E2, levuglandin E2, lymphocytic thyroid stimulator (non-immunoglobulin), alprostadil, dinoprostone, prostaglandin-inositol cyclic phosphate, Ro 22-1327, and suppressor active peptide (thermal injury.)

Prostaglandin E1 analogs include 11,15-bisdeoxyprostaglandin E1, 11-deoxy-10-hydroxyprostaglandin E1 methyl ester, 11-deoxy-13,14-dihydro-8-azaprostaglandin E(1), 11-deoxy-16,16-trimethyleneprostaglandin E1, 11-deoxy-16-phenoxy-17,18,19,20-tetranorprostaglandin E1, 11-deoxy-4,4-dimethyl-4-silaprostaglandin E1, 11-deoxy-8-azaprostaglandin E(1), 11-deoxyprostaglandin E1, 11-deoxyprostaglandin E1 4-hydroxyphenyl ester, 13,14-dihydro-15-ketoprostaglandin E1, 13,14-dihydroprostaglandin E1, 15(S)-15-methylprostaglandin E1, 15-cyclohexyl-omega-pentanor-7-thiaprostaglandin E1, 15-fluoro-11,15-dideoxyprostaglandin E1, 15-keto-13,14-dihydro-6-ketoprostaglandin E1, 15-keto-prostaglandin E0, 15-ketoprostaglandin E, 16,16-dimethyl-Δ2-prostaglandin E1, 16,18-ethano 20-ethyl-6-oxoprostaglandin E1, 16,18-ethano-20-ethyl-6-oxoprostaglandin E1 leucinamide, 17,18-dehydroprostaglandin E1, 18-hydroxyprostaglandin E1, 19-hydroxyprostaglandin E1, 20-dimethyl-7-thiaprostaglandin E1 methyl ester, 20-hydroxyprostaglandin E1, 3,7-dithia(11α,13E,15S)-11,15-Dihydroxy-9-oxoprost-13-en-1-oic acid, 3-oxa-4,5,6-nor-(3,7-inter)-3-phenyleneprostaglandin E1 methyl ester, 3-oxa-4,5,6-nor-3,7-inter-3-phenyleneprostaglandin E1, 3-oxa-4,5,6-trinor-3,7-inter-3-phenyleneprostaglandin E1 amide, 4-thiaprostaglandin E1, 5(6)-epoxyprostaglandin E1α, 5,6-dihydroxyprostaglandin E1, 6-ketoprostaglandin E1, 7-keto-9,9-ethylenedioxiprostanoid, 7-oxo-15-methylprostaglandin E1 methyl ester, 8-azaprostaglandin E1, alibra, AY 23626, butaprost, δ-17-tetranorprostaglandin E1, enisoprost, gemeprost, isoprostaglandin E1, limaprost, limaprost-alfadex, lubiprostone, MDL 646, MR 356, NP 01A, NP 07 A, NP 13 A, ONO 1082, ONO 1206, ONO-DI-004, ornoprostil, prostaglandin E0, prostaglandin E1 ethyl ester, prostaglandin E1 methyl ester, prostaglandin E1α-cyclodextrin, prostaglandin E1-hexyl-sepharose, prostaglandin E3, SC 29169, SC 31391, SC-46275, SPM 206, tetranorprostaglandin E1, TFC 612, and TR4161.

Dinoprostone (prostaglandin E2) analogs include 11-deoxy,16,16-dimethyl prostaglandin E2, 11-deoxy-11,12-methanoprostaglandin E2, 11-deoxy-11α-(2-hydroxyethylthio)-prostaglandin E2 methyl ester, 11-deoxy-15-keto-13,14-dihydro-11 beta,16-cycloprostaglandin E2, 11-deoxyprostaglandin E2-1-alcohol, 12-isoprostaglandin F(2α), 13,14-didehydroprostaglandin E2, 13,14-dihydro-16-phenyl-Ω-tetranorprostaglandin E2, 13,14-dihydroprostaglandin E2, 15-deoxy-16-hydroxy-16-vinylprostaglandin E2, 15-fluoro-15-deoxyprostaglandin E2, 15-hydroperoxyprostaglandin E2, 15-keto-13,14-dihydroprostaglandin E2, 15-keto-13,14-dihydroprostaglandin E2-thyroglobulin conjugate, 15-ketoprostaglandin E2, 16-methyl prostaglandin E2, 16-methyl-13,14-didehydroprostaglandin E2, 16-methyl-16-methoxyprostaglandin E2, 16-methyl-20-methoxy-prostglandin E2, 17,17-dimethylprostaglandin E2, 17-(4-azidophenyl)-18,19,20-trinorprostaglandin E2, 17-phenyltrinorprostaglandin E2, 18,18,20-trimethylprostaglandin E2, 18-hydroxyprostaglandin E2, 19,20-dehydroprostaglandin E2, 19-hydroxyprostaglandin E2, 1a,1b-dihomoprostaglandin E2, 20-hydroxyprostaglandin E2, 20-isopropylidene prostaglandin E2, 20-methyl-13,14-didehydroprostaglandin E2, 8,12-epi-prostaglandin E2, 8-isoprostaglandin E2, 9-deoxy-9-chloro-15-deoxy-16-hydroxy-17,17-trimethylene-19,20-didehydroprostaglandin E2, 9-enol-prostaglandin E2 methyl ester trimethylsilyl ether, FCE 20700, HOE 260, N-acetylprostaglandin E2 carboxamide, ONO AE 248, prostaglandin D2 ethanolamide, prostaglandin E2 azidophenacyl ester, prostaglandin E2 ethanolamide, prostaglandin E2 glyceryl ester, prostaglandin E2 methyl ester, prostaglandin E2 methyl oxime, prostaglandin F2α ethanolamide, prostamide H2, sulprostone, trimoprostil, and viprostol.

Prostaglandins F analogs include (5Z)-7-((1R,2R,3R,5S)-2-((1E)-3,3-difluoro-4-phenoxy-1-butenyl)-3,5-dihydroxycyclopentyl)-5-heptenoic acid, 15-cis-(4-n-propylcyclohexyl)-16,17,17,19,20-pentanor-9-deoxy-6,9-α-nitriloprostaglandin F1, 2,3-dinor-6-oxoprostaglandin F1β, 5(6)-epoxyprostaglandin F1α, 5,6-dihydroxyprostaglandin F1, 5,7-dihydroxy-11-ketotetranorprostanoic acid, alfaprostol, butyryl prostaglandin F1 butyl ester, C22-prostaglandin F4α, 6-Ketoprostaglandin F1α, lymphocytic thyroid stimulator (non-immunoglobulin), Dinoprost, prostaglandin F-main urinary metabolite, prostaglandin F1, prostaglandin F1β, prostaglandin F2β, prostaglandin F3α, and tafluprost.

6-Ketoprostaglandin F1α analogs include 2,3-dinor-6-ketoprostaglandin F1α, 5-hydroxy-6-ketoprostaglandin F1α, 6,15-diketo-13,14-dihydroprostaglandin F1α, 6,15-diketoprostaglandin F1α, 6-ketoprostaglandin F1α-thyroglobulin conjugate, 6-ketoprostaglandin F1α-tyramide, Δ(17)-6-ketoprostaglandin F1α, and endothelin-1,2-6-ketoprostaglandin F1α.

Dinaprost (prostaglandin F2α) analogs include 1-ethyl (5Z)-7-((1R,2R,3R,5S)-2-((1E)-3,3-difluoro-4-phenoxy-1-butenyl)-3,5-dihydroxycyclopentyl)-5-heptenoate, 1-methyl (5Z)-7-((1R,2R,3R,5S)-2-((1E)-3,3-difluoro-4-phenoxy-1-butenyl)-3,5-dihydroxycyclopentyl)-5-heptenoate, 11-fluoro-11-dehydroxyprostaglandin F2α, 11-fluoro-11-deoxyprostaglandin F2α, 11-ketotetranorprostaglandin F2α, 13,14-dihydroprostaglandin F2α, 13,14-dihydroxy-15-ketoprostaglandin F2α, 15-fluoro-15-deoxyprostaglandin F2α, 15-keto-13,14-dihydroprostaglandin F2α, 15-keto-17-phenyl-18,19,20-trinorprostaglandin F2α-1-isopropyl ester, 15-ketoprostaglandin F2α, 15-propionat-prostaglandin F2α-isopropyl ester, 16,16-dimethylprostaglandin F2α, 16-(3-chlorophenoxy)-17,18,19,20-tetranorprostaglandin F2α, 16-aminoprostaglandin F2α methyl ester, 16-fluoromethyleneprostaglandin F2α, 17-azaprostaglandin F2α, 17-phenyl-18,19,20-trinor-prostaglandin F2α-1-isopropyl ester, 17-phenyl-18,19,20-trinorprostaglandin F2α, 17-phenylprostaglandin F2α, 18,19,20-trinor-17-cyclohexyl-13,14-dehydroprostaglandin F2α methyl ester, 19-hydroxyprostaglandin F, 1a,1b-dihomoprostaglandin F2, 2,3-dinor-5,6-dihydro-15-F-isoprostane, 2,3-dinor-5,6-dihydro-8-isoprostaglandin F2α, 2,3-dinor-5,6-dihydroisoprostane F2α-III, 2-decarboxy-2-(P-methylphosphinico)-16-phenoxytetranorprostaglandin F2α, 20-methyl-13,14-(didehydroprostaglandin) F2α, 3-(3,5-dihydroxy-2-(oxodecyl)cyclopentyl)propionic acid, 6-keto-prostaglandin F2α, 7-(3,5-dihydroxy-2-(3-oxodecyl)cyclopentyl)hept-5-enoic acid, 8,12-iso-isoprostane F2α-III, 8,12-iso-isoprostane F2α-VI, 8-epi-prostaglandin F2α, 9-chloro-15-cyclohexyl-11,15-dihydroxy-3-oxa-16,17,18,19,20-pentanor-5-prostenoic acid, AFP-157, AL 6598, AL 8810, AL 8810 ethylamide, AL-3138, AY 24366, delprostenate, dinoprost tromethamine, etiproston, etiproston tromethamine, fluprostinol, ICI 79939, isopropyl unoprostone, N-dimethylamino-prostaglandin F2α, PhXa 85, prostaglandin F2 ethyl ester, prostaglandin F2 isopropyl ester, prostaglandin F2 methyl ester, prostaglandin F2α 11-methyl ether, prostaglandin F2α 15-methyl ether, prostaglandin F2α 9-methyl ether, prostaglandin F2α N-dimethylamide, ZK 110841, ZK 118182, and ZK 71677.

Epoprostenol analogs include 10,10-difluoro-13-dehydroprostacyclin, 11-desoxyprostacyclin, 13,14-dehydroprostaglandin I2, 13,14-dehydroprostaglandin I2 methyl ester, 13,14-didehydro-20-methylcarboprostacyclin, 13,14-dinor-inter-p-phenylene carbacyclin, 15-cyclopentyl-7-oxo-prostaglandin I2-ephedrine, 15-deoxy-(16-m-tolyl)-17,18,19,20-tetranorisocarbacyclin methylester, 15-deoxy-16-m-tolyl-17,18,19,20-tetranorisocarbacyclin, 15-fluoro-13,14-dehydrocarbacyclin, 15-ketoprostaglandin I2, 16-tolyl-17,18,19,20-tetranorisocarbacyclin, 17,20-dimethylisocarbacyclin, 19-(3-azidophenyl)-20-norisocarbacyclin, 2,2,10,10-tetrafluoro-13-dehydroprostacyclin, 20-methyl-13,14-didehydro-2,4-inter-3-phenylene prostaglandin I2, 3-oxa-9(O)-methano-delta(6,9)prostaglandin I(1), 3-oxacarbacyclin, 3-oxahomoisocarbacyclin, 4,5-didehydroisocarbacyclin, 5,6-dihydroprostacyclin, 5-hydroxyprostaglandin I, 5-methyleneisocarbacyclin, 5-nitroprostaglandin I1, 5-nitroprostaglandin I2, 6,9-thiaprostacyclin, 6a-carbaprostaglandin I3, 7-fluoroprostacyclin, 7-oxo-cyclopentyl-prostaglandin I2, 7-oxo-prostaglandin I2-ephedrine, 7-oxoprostaglandin I2, 7a-homo-2-norprostacyclin, 9-O-methanoprostaglandin I, AFP 03, AFP 06, AFP 07, APS 306, benzodioxane prostacyclin, beraprost, bicyclo(4.3.0)non-2-ene homoisocarbacyclin, carbaprostacyclin, carboprostacyclin, CG 4303, Chinoin 7284, Chinoin 7384, cicaprost, ciprostene, CL 115999, dehydro-15-cyclohexylcarbaprostacyclin, dihomo-prostaglandin I(2), FCE 21258, HOE 892, homoisocarbacyclin, KP 10614, MM 706, naxaprostene, nileprost, nitriloprostaglandin I2, ONO 41483, OP 2507, OP 41483-α-cyclodextrin, piriprost, prostaglandin I2 11-methyl ether, prostaglandin I2 15-methyl ether, prostaglandin I2 methyl ester, prostaglandin I3, R 59274, SC 39902, SM 10902, SM 10906, taprostene, TEI 1324, TEI 3356, TEI 4343, TEI 9090, TFC 132, tilsuprost, treprostinil, TRY 200, TTC 909, TY 10957, TY 11223, U 56467, U 68215, and U 72382.

Synthetic prostaglandin analogs include (+)(−)-8,12-trans-9-oxo-prosta-5,14-dienoic acid, 11-methoxime prostaglandin D2, 9α,11α,15α-trihydroxy-16-phenoxy-17,18,19,20-tetranorprosta-4,5,13-trienoic acid, 9-chloro-15-cyclohexyl-11,15-dihydroxypentanor-5,13-prostadienoic acid, 9-fluoro-15-cyclohexyl-11,15-dihydroxypentanor-5,13-prostadienoic acid, AL-12182, EMD 33290, EP 045, EP 092, GIF 0010, GIF 0037, Iloprost, synthetic prostaglandin endoperoxides, synthetic prostaglandins A, synthetic prostaglandins E, synthetic prostaglandins F, and U 62840. Iloprost analogs include 2,6-dichloro-4-aminophenol iloprost, eptaloprost, and iloprost phenacyl ester. Synthetic prostaglandin endoperoxides include 9,11-azo-13-oxa-15-hydroxyprostanoic acid, 9,11-iminoepoxyprosta-5,13-dienoic acid, prostaglandin H2 9-cyclic ether, prostaglandin H2 methyl ester, and U 44069. Synthetic prostaglandins A include 16,16-dimethylprostaglandin A1, 9-oxo-15-hydroxy-Δ7,10,13-prostatrienoic acid methyl ester, GSH-prostaglandin A1, HR 546, punaglandin III, and TEI9826. Synthetic prostaglandins E include 16,16-dimethylprostaglandin E, 16-hydroxy-16-methyl-9-oxo-prosta-10,13-dien-1-oic acid methyl ester, CL 115574, CL 116069, CP 48630, 16,16-dimethylprostaglandin E2 or an analog thereof (e.g., 11-methyl-16,16-dimethylprostaglandin E2, 16,16-dimethylprostaglandin E2 (4-acetamidobenzamido)phenyl ester, 16,16-dimethyprostaglandin E2 4-benzaldehyde semicarbazone ester, 19-hydroxy-16,16-dimethylprostaglandin E2, 9-deoxy-16,16-dimethyl-tetranor-9-methyleneprostaglandin E2, and meteneprost), enprostil, GR 63799X, arbaprostil or a analog thereof (e.g., 15-deoxy-16-methyl-16-hydroxy-3,4-didehydroprostaglandin E2 methyl ester and 15-methylprostaglandin E2 methyl ester), misoprostol or an analog thereof (e.g., 2-demethoxycarbonyl-2-ethoxycarbonyl-11-deoxymisoprostol, Arthrotec, diclofenac-misoprostol, misoprostol acid, and SC 53450), ONO-747, rioprostil, Ro 22-6923, RS 20216, RS 61565, and Wy 17186.

Aristolochic Acid

The compositions, methods, and kits of the invention may include the use of aristolochic acid, or an analog thereof. Aristolochic is a phospholipase A inhibitor. The structure of aristolochic acid is:

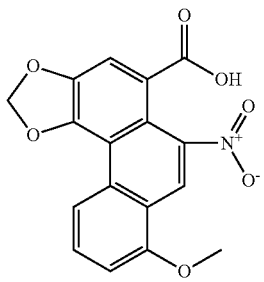 [SMILES: COc1cccc2c1cc([N+](=O)[O-])c1c(C(=O)O)cc3c(c12)OCO3]

Analogs of aristolochic acid include 7-(deoxyadenosin-N(6)-yl)aristolactam II, 7-(deoxyadenosin-N(6)-yl)aristolactam I, 7-(deoxyguanosin-N(2)-yl)aristolactam II, 7-(deoxyguanosin-N(2)-yl)aristolactam I, 7-methoxyaristolochic acid A, 7-methoxyaristololactam IV, 9-ethoxyaristolactone, 9-ethoxyaristololactam, 9-hydroxy aristolochic acid I, aristolactam I, aristolic acid, aristolochic acid C, aristolochic acid E, aristolochic acid II, aristololactam BII, aristololactam IVa, aristololactam-glucoside, aristoloside, methyl aristolate, and N-((6'-p-coumaroyl)glucopyranosyl)aristolactam.

Carbadox

The compositions, methods, and kits of the invention may include the use of carbadox, or an analog thereof. The structure of carbadox is:

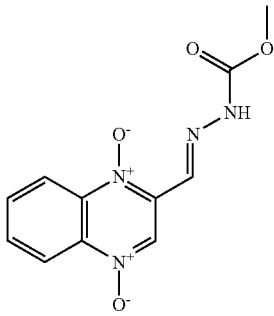 [SMILES: COC(=O)N/N=C/c1c[n+]([O-])c2ccccc2[n+]1[O-]]

Analogs of carbadox are described in U.S. Pat. No. 3,371,090 and have the formula:

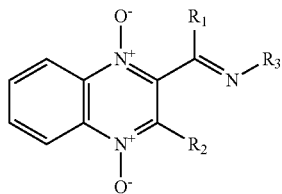

where each of $R_1$ and $R_2$ is individually selected from the group consisting of H and $C_{1-8}$ alkyl; $R_3$ is selected from the group consisting of $NHCONH_2$, $NHC(S)NH_2$, $NHCNHNH_2$, $NHR_4$, $NHCOOR_5$, $NHCOR_6$, $OR_7$, where $R_4$ is selected from the group consisting of $C_{1-8}$ alkyl, phenyl, benzyl, and hydroxyalkyl containing from 2 to 4 carbon atoms; $R_5$ is selected from the group consisting of lower alkyl, hydroxyalkyl containing from 2 to 4 carbon atoms, and haloalkyl containing from 2 to 4 carbon atoms; $R_6$ is selected from the group consisting of $C_{1-8}$ alkyl and phenyl; and $R_7$ is selected from the group consisting of hydrogen and $C_{1-8}$ alkyl.

Chlorpyrifos

The compositions, methods, and kits of the invention may include the use of chlorpyrifos, or an analog thereof. The structure of chlorpyrifos is:

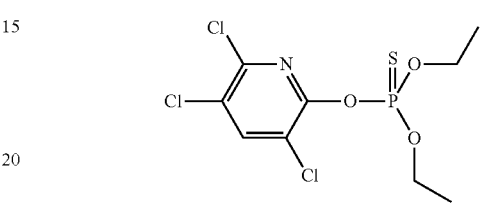

Analogs of chlorpyrifos are described in U.S. Pat. No. 3,244,586 and have the structure:

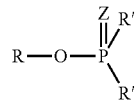

where R is pyridyl optionally substituted with one or more (e.g., 2, 3, 4) halogen groups, Z is O or S, and each R' independently represents $C_{1-8}$ alkoxy, amino, or $C_{1-8}$ alkylamino.

Cyclocreatine

Creatines, such as cyclocreatine, may be used in the compositions, methods, and kits of the invention. Cyclocreatine has the structure:

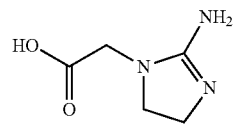

Creatine analogs are described in U.S. Pat. No. 5,998,457 and have the structure:

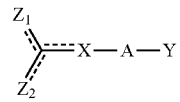

wherein

Y is —COOHNHOH, —NO$_2$, —SO$_3$H, —C(=O)NHSO$_2$J, or —P(=O)(OH)(OJ), where J is H, $C_{1-6}$ alkyl, $C_{2-6}$ alkenyl, or aryl;

A is C, CH, $C_{1-5}$ alkyl, $C_{2-5}$ alkenyl, $C_{2-5}$ alkynyl, or $C_{1-5}$ alkoyl, each having 0-2 substituents selected independently from K, where K is $C_{1-6}$ alkyl, $C_{2-6}$ alkenyl, $C_{1-6}$ straight alkoyl, and $C_{4-6}$ branched alkoyl, having 0-2 substituents independently selected from Br, Cl, epoxy, and acetoxy; a 1-2 ring aryl group optionally heterocyclic having 0-2 substituents independently selected from —CH$_2$L and —COCH$_2$L, where L is Br, Cl, epoxy, or acetoxy; and 3) —NH-M, where M is H, C$_{1-4}$ alkyl, C$_{2-4}$ alkenyl, C$_{1-4}$ alkoyl, and C$_4$ branched alkoyl;

X is NR$_1$, CHR$_1$, CR$_1$, O, or S, where R$_1$ is H; K, where K is C$_{1-6}$ alkyl, C$_{2-6}$ alkenyl, C$_{1-6}$ straight alkoyl, and C$_{4-6}$ branched alkoyl, having 0-2 substituents independently selected from Br, Cl, epoxy, and acetoxy; a 1-2 ring aryl group optionally heterocyclic having 0-2 substitutions of —CH$_2$L and —COCH$_2$L where L is Br, Cl, epoxy, or acetoxy; a C$_{5-9}$ α-amino-ω-methyl-ω-adenosylcarboxylic acid attached by the ω-methyl carbon; a C$_{5-9}$ α-amino-ω-aza-ω-methyl-ω-adenosylcarboxylic acid attached by the ω-methyl carbon; and a C$_{5-9}$ α-amino-ω-thia-ω-methyl-ω-adenosylcarboxylic acid attached by the ω-methyl carbon;

Z$_1$ and Z$_2$ are chosen independently from the group consisting of: =O, —NHR$_2$, —CH$_2$R$_2$, —NR$_2$OH; where Z$_1$ and Z$_2$ are not both =O and where R$_2$ is H; K, where K is C$_{1-6}$ alkyl; C$_{2-6}$ alkenyl, C$_{1-6}$ straight alkoyl, and C$_{4-6}$ branched alkoyl and contains 0-2 substituents independently selected from Br, Cl, epoxy, and acetoxy; a 1-2 ring aryl group optionally heterocyclic containing 0-2 substituents independently selected from —CH$_2$L and —COCH$_2$L where L is Br, Cl, epoxy, or acetoxy; a C$_{4-8}$ α-amino-carboxylic acid attached via the ω-carbon; B, where B represents —CO$_2$H—NHOH, —SO$_3$H, —NO$_2$, OP(=O)(OH)(OJ), or —P(=O)(OH)(OJ), where J is H, C$_{1-6}$ alkyl, C$_{2-6}$ alkenyl, or aryl, and B is optionally connected to the nitrogen by C$_{1-2}$ alkyl, C$_2$ alkenyl, or C$_{1-2}$ alkoyl; -D-E, where D is C$_{1-3}$ alkyl, C$_{2-3}$ alkenyl, C$_{1-3}$ straight alkoyl, aryl, or aroyl; and E is —(PO$_3$)$_n$NMP, where n is 0-2 and NMP is ribonucleotide monophosphate connected by the 5'-phosphate, 3'-phosphate, or the aromatic ring of the base; —[P(=O)(OCH$_3$)(O)]$_m$-Q, where m is 0-3 and Q is a ribonucleoside connected via the ribose or the aromatic ring of the base; —[P(=O)(OH)(CH$_2$)]$_m$-Q, where m is 0-3 and Q is a ribonucleoside connected via the ribose or the aromatic ring of the base; and an aryl group containing 0-3 substituents chosen independently from Cl, Br, epoxy, acetoxy, —OG, —C(=O)G, and —CO$_2$G, where G represents C$_{1-6}$ alkyl, C$_{2-6}$ alkenyl, C$_{1-6}$ straight alkoyl, C$_{4-6}$ branched alkoyl, and where E may be attached to any point to D, and if D is alkyl or alkenyl, D may be connected at either or both ends by an amide linkage; and -E, where E represents —(PO$_3$)$_n$NMP, where n is 0-2 and NMP is a ribonucleotide monophosphate connected by the 5'-phosphate, 3'-phosphate, or the aromatic ring of the base; —[P(=O)(OCH$_3$)(O)]$_m$-Q, where m is 0-3 and Q is a ribonucleoside connected via the ribose or the aromatic ring of the base; —[P(=O)(OH)(CH$_2$)]$_m$-Q, where m is 0-3 and Q is a ribonucleoside connected via the ribose or the aromatic ring of the base; and an aryl group containing 0-3 substituents chose independently from the group consisting of: Cl, Br, epoxy, acetoxy, —OG, —C(=O)G, and —CO$_2$G, where G represents C$_{1-6}$ alkyl, C$_{2-6}$ alkenyl, C$_{1-6}$ straight alkoyl, C$_{4-6}$ branched alkoyl; and if E is aryl, E may be connected by an amide linkage;

if R$_1$ and at least one R$_2$ group are present, R$_1$ may be connected by a single or double bond to an R$_2$ group to form a 5-7 member ring;

if two R$_2$ groups are present, they may be connected by a single or a double bond to form a 4-7 member ring; and if R$_1$ is present and Z$_1$ or Z$_2$ is —NHR$_2$, —CH$_2$R$_2$, or —NR$_2$OH, then R$_1$ may be connected by a single or double bond to the carbon or nitrogen of either Z$_1$ or Z$_2$ to form a 4-7 member ring.

7,4'-dimethoxyisoflavone

Isoflavones such as 7,4'-dimethoxyisoflavone can be used in the compositions, methods, and kits of the invention. 7,4'-dimethoxyisoflavone has the structure:

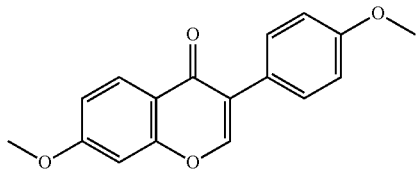

Isoflavone analogs include (3R)-4'-methoxy-2',3,7-trihydroxyisoflavanone, (3R)-6,2'-dihydroxy-7-methoxy-4',5'-methylenedioxyisoflavan, (R)-3',5-dihydroxy-4',7-dimethoxyspiro(2H-1-benzopyran-3(4H),7'-bicyclo(4.2.0)-octa(1,3,5)-trien)-4-one, 10,11-dihydroxydracaenone C, 2",6"-O-diacetyloninin, 2"-O-glycosylisovitexin, 2',4',7-trihydroxyisoflavone, 2'-hydroxy-5'-methoxybiochanin A, 2'-hydroxy-5,6,7-trimethoxyisoflavonoid, 2'-hydroxy-6,4',6",4"'-tetramethoxy(7-O-7")-bisisoflavone, 2'-methoxybonducellin, 2'-methoxydihydrobonducellin, 2,7,4'-trihydroxyisoflavanone, 2-methoxy-3,8,9-trihydroxy coumestan, 3',4',7-trihydroxyisoflavone, 3',7-dihydroxy-2',4',5',8-tetramethoxyisoflavan, 3',7-dihydroxyisoflavan, 3'-chloro-5,7-dihydroxyisoflavone, 3'-hydroxy-6,4'-dimethoxy-7-O-glucopyranozylisoflavone, 3'-methoxypuerarin, 3'-prenyl-4'-methoxyisoflavone-7-O-beta-(2"-O-4-coumaroyl) glucopyranoside, 3(2H)-isoflavene, 3-(3-bromophenyl)-5,7-dihydroxy-4-oxo-4H-chromene-2-carboxylic acid ethyl ester, 3-(4'-methoxybenzyl)-7,8-methylenedioxychroman-4-one, 3-(4-hydroxybenzyl)-5-hydroxy-6,7,8-trimethoxychroman-4-one, 4',5,6,7-tetrahydroxy-8-methoxyisoflavone-7-O-beta-D-galactopyranosyl-(1-3)-O-beta-D-xylopyranosyl-(1-4)-O-alpha-L-rhamnopyranoside, 4',5,7-trihydroxy-6,8-dimethylisoflavone, 4',5-dihydroxy-2',3'-dimethoxy-7-(5-hydroxyoxychromen-7yl)-isoflavanone, 4',5-dihydroxy-7-O-methylisoflavone-3'-O-(3"-cinnamoyl)glucoside, 4',7,8-trihydroxyisoflavone, 4',7-dimethoxy-2'-isoflavonol, 4',8-dihydroxyl-7-methoxylisoflavone, 4'-methoxypuerarin, 4'-O-coumaroyl-isovitexine, 4'-O-methyl equol, 4'-O-methylalpinumisoflavone, 5,4'-dimethoxy-3'-prenylbiochanin A, 5,6,6'-trimethoxy-3',4'-methylenedioxyisoflavone 7-O-(2"-O-4-coumaroylglucopyranoside), 5,6,7-trihydroxy-3-(3,4,5-trimethoxyphenyl)-1H-benzopyran-4-one, 5,7,4'-trihydroxy-2'-methoxyisoflavone, 5,7,4'-trihydroxy-3'-(3-hydroxy-3-methylbutyl)isoflavone, 5,7,8,4'-tetrahydroxyisoflavone, 5,7-dihydroxy-2',3',5',6'-tetramethoxy isoflavone, 5,7-dihydroxy-2',4',5'-trimethoxyisoflavanone, 5,7-dihydroxy-2'-methoxy-3',4'-methylenedioxyisoflavanone, 5,7-dihydroxy-3-(3-hydroxy-4-methoxybenzyl)-6-methoxychroman-4-one, 5-hydroxy-2',4',5'-trimethoxy-2",2"-dimethylpyrano(5",6":6,7) isoflavanone, 5-methoxyxanthocercin A, 6"-O-malonyldaidzin, 6"-O-xylosyltectoridin, 6,7,4'-trihydroxyisoflavan, 6,7,4'-trihydroxyisoflavanone, 6,7,4'-trihydroxyisoflavone, 6,7,8,3',4',5'-hexamethoxyisoflavone, 6,7-dihydroxy-4'-methoxyisoflavanone, 6-aldehydo-7-methoxyiso-ophiopogonanone B, 6-chloro-3(2H)-isoflavene, 6-hydroxy-7,2',4',5'-tetramethoxyisoflavone, 6-hydroxybiochanin A, 6-hydroxydaidzein, 6-O-glucuronopyranosyl-2',5,6-trihydroxyisoflavone, 2'-O-sulfate, 6-oxazolinylisoflavan, 7,2'-dihydroxy-3',4'-dimethoxyisoflavane-7-O-glucoside, 7,3',4'-trihydroxy-5-O-alpha-L-rhamnopyranosylisoflavone, 7,3',4'-trihydroxy-5-O-beta-D-(2"-acetyl)-xylopyranosylisoflavone, 7,3'-dihydroxy-4'-methoxy-5'-(gamma,gammadimethylally)isoflavone, 7,3'-dihydroxy-4'-methoxyisoflavone, 7,3'-dihydroxy-6",6"-dimethyl-4",5"-dehydropyrano(2",3":4',5')isoflavone, 7,3'-dihydroxyl-5'-methoxyisoflavone, 7,4'-dimethoxy-5-hydroxyisoflavone, 7,4'-dioxyethoxydaidzein, 7,4'-disuccinic acid monoester-O-ethoxydaidzein, 7,6'-dihydroxy-3'-methoxyisoflavone, 7,8,3',4',5'-pentamethoxyisoflavone, 7,8,4'-trihydroxyisoflavone, 7,8,4'-trimethoxyisoflavone, 7,8-dihydroxy-2',4',5'-trimethoxyisoflavan, 7-hydroxy-2',3',4',5',8-pentamethoxyisoflavan, 7-hydroxy-4'-methoxy-3'-prenylisoflavone, 7-hydroxy-6,4'-dimethoxy-isoflavonequinone, 7-methoxy-4'-hydroxy-3'-diethylaminomethylisoflavone, 7-O-(carboxypropyl)-4'-hydroxyisoflavone, 7-O-beta-glucopyranosyl-4'-hydroxy-5-methoxyisoflavone, 7-O-methyleucomol 5-O-glucopyranoside, 7-O-methyleucomol 5-O-neohesperidoside, 7-O-methyleucomol 5-O-rutinoside, 7-O-methylisolupalbigenin, 8-chloro-3',4',5,7-tetrahydroxyisoflavone, 8-hydroxydaidzein, 8-hydroxyglycitein, 8-isopentenylnaringenin, 8-methoxy-5,6,4'-trihydroxyisoflavone-7-O-glucopyranoside, 8-methoxyvestitol, 8-prenyldaidzein, 8-prenylmucronulatol, acetylpuerarin, afromosin, alpinumisoflavone, astraisoflavanin, auriculasin, bavadin, bidwillon B, biochanin A 7-O-(apiofuranosyl-(1-5)-apiofuranosyl-(1-6)-glucopyranoside), bolusanthol A, bolusanthol B, bolusanthol C, cabreuvin, cajanol, calycosin-7-O-beta-D-glucoside, calycosin-7-O-glucopyranoside, chungkookjang, CJY compound, CK 122, claussequinone, colutehydroquinone, colutequinone, coromandelin, coumestrol, daidzein, daidzein 7-O-beta-D-glucuronide-4'-O-sulfate, daidzein-4',7-yl diglucopyranosiduronic acid, daidzein-4'-O-sulfate, daidzein-4,7-diglucoside, daidzein-7,4'-di-O-sulfate, daidzein-7-yl glucopyranosiduronic acid, daidzin, dalbergion 4'-O-glucopyranoside, dalcongestin, dalnigrein7-O-beta-D-apiofuranosyl-(1-6)-beta-D-glucopyranoside, dalpatein 7-O-beta-D-apiofuranosyl-(1-6)-beta-D-glucopyranoside, dehydroequol, derrubone, desmodianone A, desmodianone B, desmodianone C, dichotomitin, dihydrobonducellin, dihydrodaidzein, dihydrodaidzin, dihydrogenistin, dihydroisoderrondiol, dihydrolicoisoflavone, duartin, echinoisoflavanone, EMD 16795, equol, eriotriochin, erycristagallin, euchrenone b10, eurycarpin A, eurycarpin B, formononetin, fremontin, fremontone, fujiflavone P40, furowanin B, gancaonin A, genistein, genistein 4',7'-bis(6-deoxytalopyranoside), genistein 7-(6-deoxytalopyranoside), genistein 7-O-alpha-L-rhamnopyranoside-4'-O-(6'''-O-alpha-L-rhamnopyranosyl)-beta-sophoroside, genistein 7-O-beta-D-glucopyranoside-4'-O-(6'''-O-alpha-L-rhamnopyranosyl)-beta-sophoroside, genistin, glabrene, glabrizoflavone, glaziovianin A, glicoisoflavanone, glisoflavanone, glycitein, glycitin, haginin A, hydroxyethylpuerarin, indicanine C, intricatinol, ipriflavone, irigenin, irilin A, irilin B, irilin D, irilone, irisone A, irisone B, isocytisoside, isocytisoside-7-O-glucopyranoside, isoflavanone, isovitexin 2"-O-glucoside, isovitexin-4'-O-glucoside, judaicin (isoflavone), kakkalide, kievitone, kraussianone 1, kraussianone-1, kraussianone-2, kwakhurin, lanceolarin, licoisoflavone A, licoisoflavone B, lupinalbisone A, lupinalbisone B, mahuangchiside, malonylgenistin, manuifolin D, manuifolin E, manuifolin F, manuifolin Q, menoflavon, methylaminium 4',7-dihydroxyisoflavone-3'-sulfonate, methylophiopogonanone B, millewanin G, millewanin H, munetone, muscomin, N99-596 A, N99-596 B, nigrolineaisoflavone A, O-desmethylangolensin, O-methylclaussequinone, ormosidin, osajaxanthone, osajin, pallidiflonic acid methyl ester, pallidiflorin, pentandrin, pentandrin glucoside, phaseollin (isoflavan), phenoxodiol, phytosoya, promensil, prunetin, prunetin-4'-O-beta-D-gentiobioside, psi-baptigenin, psi-tectorigenin, Pterocarpans, puerarin, robustic acid, rotenone, sativan, scandenone, senegalensin, sigmoidin I, sigmoidin J, sigmoidin K, smiranicin, sophoraisoflavanone D, sophoraisoflavone A, sophorol, soy isoflavone aglycone, tectoridin, tectorigenin, tectorigenin 7-O-(apiofuranosyl-(1-6)-glucopyranoside), tetrahydrodaidzein, tlatancuayin, torvanol A, triquetrumone A, triquetrumone B, triquetrumone C, triquetrumone D, ulexin C, ulexin D, vavain, vavain 3'-O-glucoside, vogelin A, vogelin B, vogelin C, vogelin H, vogelin I, vulgarin (isoflavones), warangalone, warangalone-4'-methyl ether, and yufengningxin. Analogs are also described in U.S. Pat. Nos. 2,764,596, 2,892,845, 2,892,846, 3,755,372, 3,907,830, 3,864,362, 4,841,077, and 4,264,509.

Dorzolamide

The compositions, methods, and kits of the invention may use dorzolamide or an analog thereof. Dorzolamide has the structure:

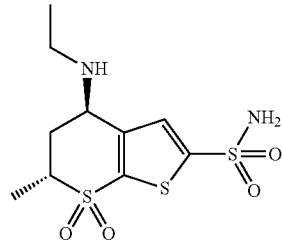 [SMILES: CCN[C@@H]1C[C@@H](C)S(=O)(=O)c2sc(S(N)(=O)=O)cc21]

Analogs of dorzolamide are described in U.S. Pat. No. 4,677,115 and have the structure:

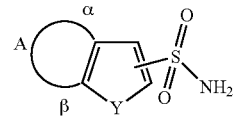

wherein A together with the two carbon atoms denoted as α and β is the group:

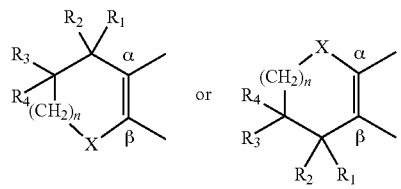

wherein

X is S, SO, $SO_2$ or $CH_2$;

Y is S, O, or $NR_3$ where $R_3$ is H; $C_{1-3}$ alkyl, or benzyl;

n is 1 or 2;

$R_1$, $R_2$, $R_3$, $R_4$ are independently:

H;

$OR_5$ where $R_5$ is H, $C_{1-5}$ alkyl optionally substituted with OH or $NR_6R_7$ where $R_6$ and $R_7$ are independently H or $C_{1-5}$ alkyl or are joined together form a heterocycle with the nitrogen to which they are attached (e.g., piperidino, morpholino, or piperazino), $C_{1-5}$ alkanoyl optionally substituted with OH, $NR_6R_7$, $NHCOR_8$, or $COR_8$ where $R_8$ is OH, $NR_6R_7$, or $C_{1-5}$ alkoxy; or $COR_9$, where $R_9$ is $NR_6R_7$ or a 5- or 6-membered aromatic heterocycle such as pyridyl, imidazolyl, pyrazinyl, thiazolyl, thienyl, or oxazolyl;

$NR_6R_7$;

$NHR_{10}$ wherein $R_{10}$ is $SO_2NR_6R_7$, $SO_2R_{11}$ where $R_{11}$ is $C_{1-5}$ alkyl, or $CONR_6R_7$, $C_{1-5}$ alkyl, optionally substituted with $OR_5$, CN, $NR_6R_7$, or $COR_8$, $SO_2R_{11}$;

$SO_2NR_6R_7$, or halo, such as Cl, Br, or F;

$R_1$ and $R_3$, or $R_2$ and $R_4$ taken together represent a double bond; $R_1$ and $R_2$, or $R_3$ and $R_4$ taken together represent =O, or =$NOR_{12}$ where $R_{12}$ is H or $C_{1-3}$ alkyl; and one of the $CH_2$ groups of —$(CH_2)_n$— is optionally substituted with —$COR_8$, —$CH_2R_8$, or —$CH_2COR_8$.

S(−)eticlopride

S(−)eticlopride, or an analog thereof can be used in the compositions, methods, and kits of the invention. S(−)eticlopride has the structure:

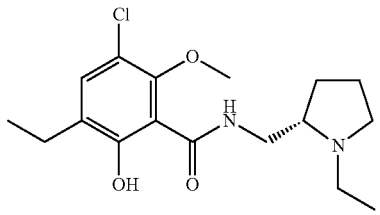 [SMILES: CCc1cc(Cl)c(OC)c(C(=O)NC[C@@H]2CCCN2CC)c1O]

Analogs of eticlopride are described in U.S. Pat. No. 4,789,683 and have the formula:

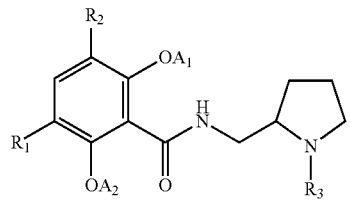

where $R_1$ and $R_2$ are independently H, a halogen, CN, $C_{1-6}$ alkyl, or acyl; $R_3$ is $C_{1-6}$ alkyl, a $C_{2-6}$ alkenyl, or $C_{6-12}$ aryl optionally substituted with F, Cl, Br, $CF_3$, $C_{1-6}$ alkyl, or $C_{1-6}$ alkoxy, $A_1$ and $A_2$ are independently H, $C_{1-6}$ alkyl group, acyl, $C_{1-6}$ alkoxycarbonyl, or a dialkylcarbamyl group, (e.g., provided that when $A_1$ and $A_2$ are the same lower alkyl group and $R_3$ is ethyl, $R_1$, $R_2$, or both are selected among CN, $C_{1-6}$ alkyl, and acyl); or a physiologically acceptable salt or optical isomers thereof.

Evoxine

Evoxine, or an analog thereof, may be used in the compositions, methods, and kits of the invention. Evoxine has the structure:

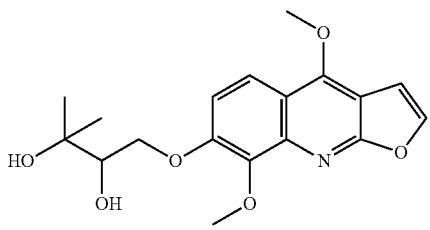 [SMILES: COc1c2ccoc2nc2c(OC)c(OCC(O)C(C)(C)O)ccc12]

Evoxine acts as a sedative and is an antagonist of strychnine and pentylenetrazole.

Guaifenesin

Guaifenesin, or an analog thereof, may be used in the compositions, methods, and kits of the invention. Guaifenesin has the structure:

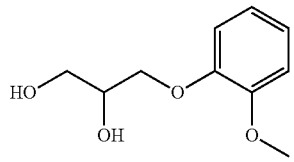

Gauifenesin is used as an expectorant.

Hydroxyprogesterones

17α-Hydroxyprogesterone (CAS No. 68-96-2), or an analog thereof, may be used in the compositions, methods, and kits of the invention. 17α-Hydroxyprogesterone has the structure:

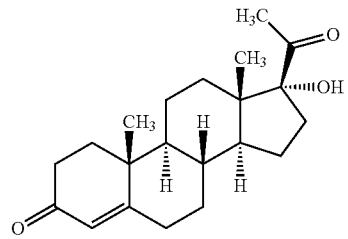

Other hydroxyprogesterone compounds include 11α-bromoacetoxyprogesterone, 11,14-dihydroxypregn-4-ene-3,20-dione, 11-hydroxyprogesterone, 11-hydroxyprogesterone 11-glucuronide, 12α-hydroxyprogesterone, 14-hydroxypregna-1,4-diene-3,20-dione, 14-hydroxyprogesterone, 15,17-dihydroxyprogesterone, 15-hydroxyprogesterone, 16α,17α-isopropylidenedioxyprogesterone, 16α-bromoacetoxyprogesterone, 16,17-epoxy-3-hydroxypregn-5-en-20-one, 16-hydroxyprogesterone, 16-methylene-17α-acetoxyprogesterone, 16-methylene-17α-hydroxyprogesterone, 17α,20β-dihydroxypregn-4-en-3-one, 17α-acetoxy-2',2',6β-trifluoro-6β,7β-dihydro-16-methylenecyclopropa(6,7)progesterone, 17,20-dihydroxy-4-pregnen-3-one, 17-(bromoacetoxy)progesterone, 17-acetoxy-11-oxaprogesterone, 17-acetoxy-7-oxaprogesterone, 17-α-hydroxy-progesterone caproate, 17-hydroxypregn-4-ene-3-one, 17-hydroxyprogesterone 17-(9-oxo-10-chlorodecanoate), 17-hydroxyprogesterone heptanoate, 17α-hydroxy-6-methylene-progesterone, 18-hydroxyprogesterone, 19-hydroxyprogesterone, 2-bromoacetoxyprogesterone, 21-amino-17-hydroxyprogesterone, 21-bromoacetoxyprogesterone, 3-O-glucopyranosyl-3,15-dihydroxypregn-5-en-20-one, 4-pregnen-20,21-diol-3-one, 6β-acetoxyprogesterone, 6,17,20-trihydroxypregn-4-ene-3-one, 6-bromoacetoxyprogesterone, 6-hydroxy-6-methyl-17-acetoxyprogesterone, 6-hydroxyprogesterone, 6-trifluoromethyl-16-methylene-17α-hydroxy-4,6-pregnadiene-3,20-dione 17-acetate, 7α-carboxymethyl-17-hydroxyprogesterone, 7β-carboxymethyl-17-hydroxyprogesterone, 7,14-dihydroxypregn-4-ene-3,20-dione, 7-hydroxyprogesterone, caprovestrol, deluteval, flumedroxone, 17α-acetoxy-3β-butanoyloxy-6-methyl-pregna-4,6-dien-20-one, 17α-acetoxy-3β-isopropyloxy-6-methylpregna-4,6-dien-20-one, 17α-acetoxy-3β-phenylpropionyloxy-6-methylpregna-4,6-dien-20-one, 17-α-hydroxyprogesterone, Injectable No. 1, methylene-dehydroacetoxy-progesterone, pregna-1,4-diene-11-ol-3,20-dione, primosiston, progesterone 11-glucuronide-alkaline phosphatase conjugate, progesterone 11-hemisuccinate, progesterone 11-hemisuccinate-(2-iodohistamine), thymine-hydroxyprogesterone, and trophobolen.

Kaempferol

Kaempferol, or an analog thereof, may be used in the compositions, methods, and kits of the invention. The structure of kaempferol is:

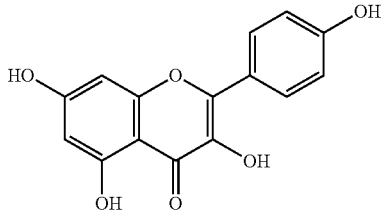 [SMILES: O=c1c(O)c(-c2ccc(O)cc2)oc2cc(O)cc(O)c12]

Analogs of kaempferol include (6'''-O-(delphinidin 3-O-(6''-O-p-coumaroylglucoside) 7-O-glucosyl)) (6''''-O-(kaempferol 3-O-glucoside, 7-O-xyloside, 4'-O-glucosyl)) succinate, (6'''-O-(delphinidin 3-O-(6''-O-p-coumaroylglucoside) 7-O-glucosyl)) (6''''-O-(kaempferol 3,7-di-O-glucoside, 4'-O-glucosyl))succinate, 3,4'-dimethyl-kaempferol, 3,7-O-dimethylkaempferol, 3-hydroxy-2,3-dihydroapigenyl-(I-4',O,II-3')-dihydrokaempferol, 3-methyl-kaempferol, 3-O-((xylopyranosyl(1-3)-rhamnopyranosyl(1-6))(apiofuranosyl(1-2)))-galactopyranosyl kaempferol, 3-O-β-(β-(6'''-acetyl)-D-glucopyranosyl(1-2))-D-glucopyranosyl kaempferol, 3-O-glucosyl-1-6-glucosylkaempferol, 3-O-rhamnopyranosylkaempferol-7-O-glucopyranoside, 4'''-acetylvitexin-2''-O-rhamnoside, 6,8-di-C-methylkaempferol 3-methyl ether, 6,8-dihydroxyafzelin, 6-hydroxykaempferol-3-O-glucoside, 6-methoxykaempferol 3-O-rhamnoside, 7-O-acetyl-3-O-glucosylkaempferol, 7-O-α-L-rhamnopyranosyl-kaempferol-3-O-α-L-rhamnopyranoside, 7-O-α-L-rhamnopyranosyl-kaempferol-3-O-β-D-glucopyranoside, 8-lavandulylkaempferol, 8-methoxykaempferol-3-O-glucoside, afzelin 3''-O-gallate, amoenin A3, astragalin, camelliaside A, camelliaside C, clitorin, des-O-methylicariine, kaempefrol-3-O-arabinofuranoside-7-O-rhamnopyranoside, kaempferide, kaempferide 3-O-glucopyranosyl-1-2-O-(rhamnopyranosyl-1-6)glucopyranoside, kaempferide 3-O-neohesperidoside, kaempferol 3-(2(Gal)-(4-acetylrhamnosyerobinobioside), kaempferol 3-(2(Gal)-rhamnosylrobinobioside), kaempferol 3-(2,4-di-(4-coumaroyl)rhamnoside), kaempferol 3-arabinoside, kaempferol 3-gentiobioside, kaempferol 3-glucosyl(1-3)rhamnosyl(1-6)galactoside, kaempferol 3-O-((6''''-feruloyl)-β-D-glucopyranosyl-(1-3))-(α-L-rhamnopyranosyl-(1-6))-β-D-glucopyranoside, kaempferol 3-O-(2''-O-galloylrutinoside), kaempferol 3-O-(2(G)-(E)-coumaroyl-3(G)-O-β-D-glucosyl-3(R)—O-β-D-glucosylrutinoside), kaempferol 3-O-(apiofuranosyl-(1'''-2'')-rhamnopyranosyl-(1''''-6''))-galactopyranoside, kaempferol 3-O-α-L-3''-acetyl-arabinofuranoside, kaempferol 3-O-α-rhamnopyranosyl(1-2)-β-galactopyranoside-7-O-β-glucopyranoside, kaempferol 3-O-α-rhamnopyranosyl-(1-2)-β-galactopyranoside, kaempferol 3-O-apiofuranoside 7-O-α-rhamnosyl-(1'''-6'')-O-galactopyranoside, kaempferol 3-O-apiofuranoside 7-O-rhamnosyl-(1''''-6''')-O-(2'''-O-E-caffeoylgalactopyranoside), kaempferol 3-O-apiofuranosyl-1-6-glucopyranoside, kaempferol 3-O-glucopyranoside-6''-(3-hydroxy-3-methyl glutarate), kaempferol 3-O-glucopyranosyl-1-4-rhamnopyranosyl-1-6-galactopyranoside, kaempferol 3-O-neohesperidoside, kaempferol 3-O-rhamnopyranosyl(1-2)-galactopyranoside-7-O-arabinofuranoside, kaempferol 3-O-rhamnopyranosyl(1-6)-galactopyranoside-7-O-arabinofuranoside, kaempferol 3-O-rhamnopyranosyl-1-6-glucopyranosyl-1-6-galactopyranoside, kaempferol 3-O-rhamnopyranosyl-1-6-O-(glucopyranosyl-1-3-O-rhamnopyranosyl-1-2)-O-galactopyranoside, kaempferol 3-O-rhamnoside, kaempferol 3-O-sophoroside, kaempferol 3-O-sophoroside-7-O-glucoside, kaempferol 3-rhamnosyldiglucoside, kaempferol 7-neohesperidoside, kaempferol 7-O-(2,3-di-E-p-coumaroyl-α-L-rhamnoside), kaempferol 7-O-(2-E-p-coumaroyl-α-L-rhamnoside), kaempferol 7-O-glucoside, kaempferol rhamnorobinoside, kaempferol-2,4-dicoumaroyl-3-O-glucoside, kaempferol-3-(4-coumaroyl triglucoside), kaempferol-3-β-D-(6-O-trans-p-coumaroyl)glucopyranoside, kaempferol-3-O-((xylopyranosyl(1-3)-rhamnopyranosyl(1-6))(rhamnopyranosyl(1-2)))galactopyranoside, kaempferol-3-O-(2,3,4-tri-O-acetyl-α-1-rhamnopyranoside), kaempferol-3-O-(2,3-di-O-acetyl-α-1-rhamnopyranoside), kaempferol-3-O-(6'',4''-di-p-coumaroyl)mannopyranoside, kaempferol-3-O-(6''-p-coumaroyl)mannopyranoside, kaempferol-3-O-(6-trans-caffeoyl)-β-D-glucopyranosyl-(1-2)-β-D-glucopyranoside-7-O-β-D-glucopyranoside, kaempferol-3-O-(apiofuranosyl-(1'''-2''))-galactopyranoside, kaempferol-3-O-(rhamnopyranosyl-rhamnopyranosyl-(1-6)-galactoside), kaempferol-3-O-α-L-(6''-ethyl)-rhamnopyranoside, kaempferol-3-O-α-L-(6''-methyl)-rhamnopyranoside, kaempferol-3-O-α-L-5''-acetyl-arabinofuranoside, kaempferol-3-O-α-L-arabifuranoside, kaempferol-3-O-β-D-(6''-O-p-coumaroyl)galactopyranoside, kaempferol-3-O-β-D-galactoside, kaempferol-3-O-β-D-glucopyranoside-7-O-α-L-arabinofuranoside, kaempferol-3-O-galactoside, kaempferol-3-O-glucopyranoside-6''-(3-hydroxy-3-methyl glutarate)-7-O-glucopyranoside, kaempferol-3-O-glucopyranosyl-1-4-rhamnopyranoside, kaempferol-3-O-glucoside, kaempferol-3-O-glucosyl (1-2)rhamnoside, kaempferol-3-O-rutinoside, kaempferol-4',7-dimethyl-3-O-glucoside, kaempferol-7-O-α-L-rhamnopyranoside, lespenefril, mauritianin, morindaoside, nigeglanoside, siparunoside, and trifolin acetate.

Linamarin

Linamarin, or an analog thereof, may be used in the compositions, methods, and kits of the invention. The structure of linamarin is:

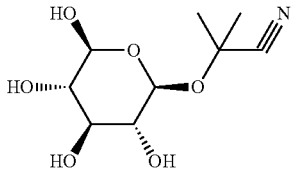 [SMILES: CC(C)(C#N)O[C@@H]1O[C@H](O)[C@@H](O)[C@H](O)[C@H]1O]

Linamarin is a cyanogenic glucoside found in the leaves and roots of plants such as cassava, lima beans, and flax.

Mexicanolide

Mexicanolide, or an analog thereof, may be used in the compositions, methods, and kits of the invention. The structure of mexicanolide is:

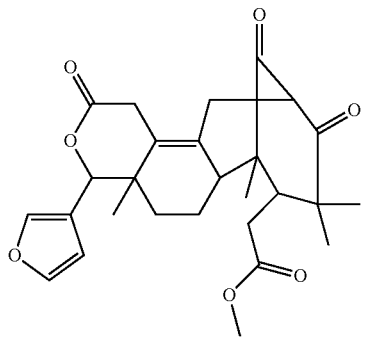 [SMILES: COC(=O)CC1C(C)(C)C(=O)C2C(=O)C23CC2=C4CC(=O)OC(c5ccoc5)C4(C)CCC2C13C]

Mexicanolide is found in the Spanish cedar (*Cedrela odorata* L).

MG 624

MG 624, or an analog thereof, may be used in the compositions, methods, and kits of the invention. The structure of MG 624 is:

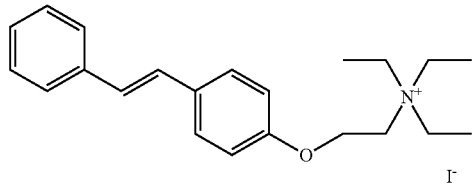 [SMILES: CC[N+](CC)(CC)CCOc1ccc(/C=C/c2ccccc2)cc1 ; [I-]]

Analogs of MG 624 are described in Mantegazza et al., Arch. Int. Pharmacodyn., 4:371, 1955 and Gotti et al., Br. J. Pharmacol. 124:1197, 1998.

Pramoxine

Pramoxine, or an analog thereof, may be used in the compositions, methods, and kits of the invention. The structure of pramoxine is:

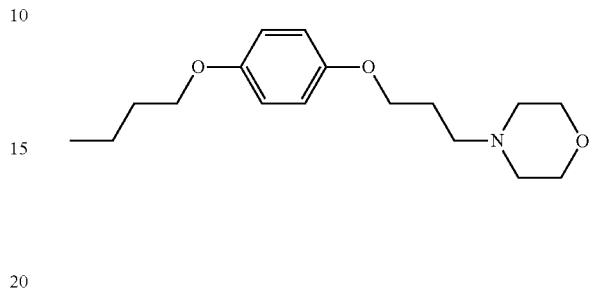

Pramoxine is used as a topical anesthetic, often in treatment of insect bites.

Tannic Acid

Tannic acid or tannic complexes may be used in the compositions, methods, and kits of the invention. Tannic acid is a polymer made up of a glucose molecule attached by ester linkages and to one or more gallic acid units, which, in turn, may be further attached to additional gallic acid units. Tannic acid can have the structure:

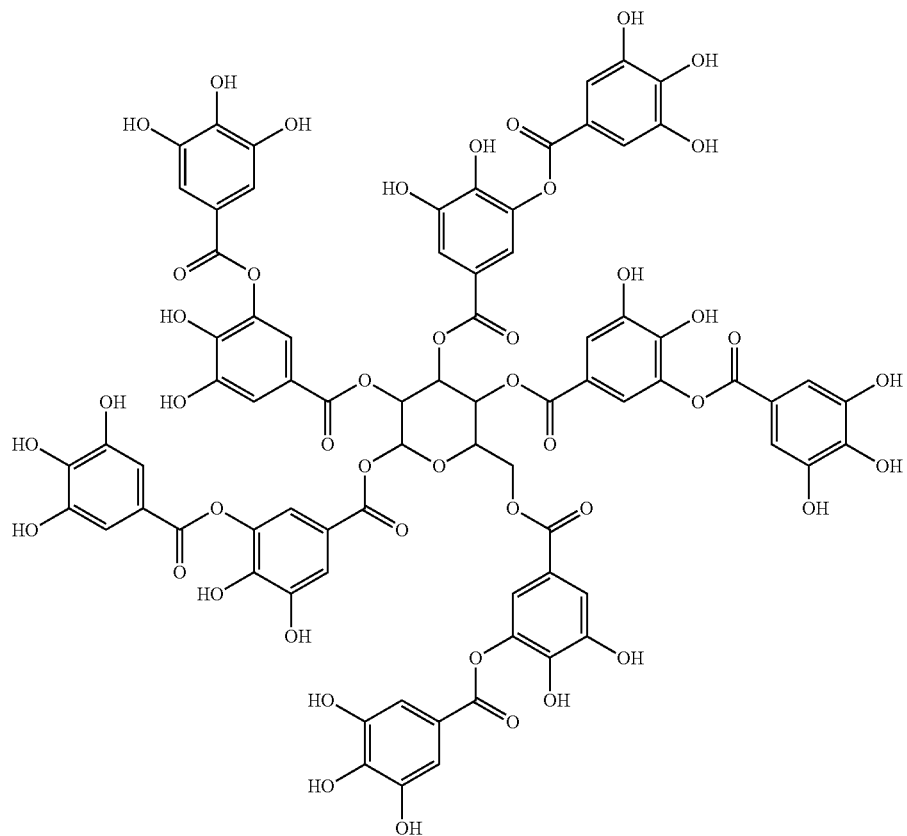 [SMILES: O=C(OCC1OC(OC(=O)c2cc(O)c(O)c(OC(=O)c3cc(O)c(O)c(O)c3)c2)C(OC(=O)c2cc(O)c(O)c(OC(=O)c3cc(O)c(O)c(O)c3)c2)C(OC(=O)c2cc(O)c(O)c(OC(=O)c3cc(O)c(O)c(O)c3)c2)C1OC(=O)c1cc(O)c(O)c(OC(=O)c2cc(O)c(O)c(O)c2)c1)c1cc(O)c(O)c(OC(=O)c2cc(O)c(O)c(O)c2)c1]

Tannic acid is used topically to treat injuries such as burns, and has been shown to have some antineoplastic effects.

Targinine

Targinine, or an analog thereof, may be used in the compositions, methods, and kits of the invention. The structure of targinine is:

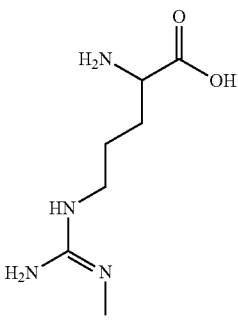

Analogs of targinine are described in U.S. Pat. No. 4,698,442 and have the structure:

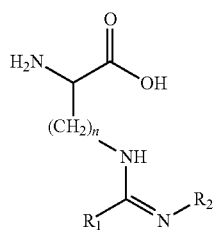

where n is 1-5; $R_1$ is $C_{1-12}$ alkyl, $C_{1-4}$ halogen substituted alkyl, or $NHR_3$ where $R_3$ is $C_{1-12}$ alkyl, $C_{3-12}$ cycloalkyl, phenyl, benzyl, $C_{1-4}$ halogen substituted alkyl, morpholino, or $(CH_2)_nN(R_4)_2$ where n is 1-5 and $R_4$ is $C_{1-4}$ alkyl; $R_2$ is H or $R_3$; or $R_1$ and $R_2$ comprise a ring represented by the following structural formulas:

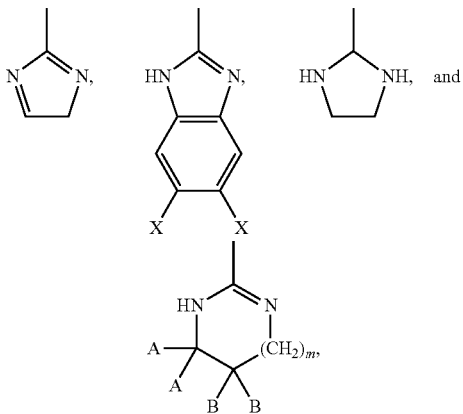

where m is 0-6; A and B are independently H, $C_{1-6}$ alkyl, or $C_{3-12}$ cycloalkyl; and X is halo or A (e.g., provided that wherein n is 3 and $R_1$ is —$NHR_3$, wherein $R_3$ is methyl and $R_2$ is H or methyl are excluded).

Yohimbic Acid

Yohimbic acid, or an analog thereof, may be used in the compositions, methods, and kits of the invention. The structure of yohimbic acid is:

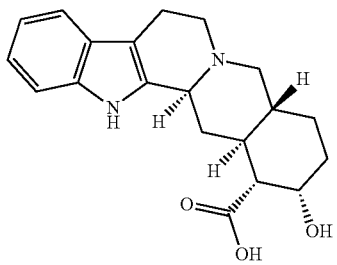 [SMILES: O=C(O)[C@@H]1[C@H]2C[C@H]3c4[nH]c5ccccc5c4CCN3C[C@@H]2CC[C@@H]1O]

Analogs of yohimbic acid are described in U.S. Pat. Nos. 2,796,420, 2,841,586, 2,977,367, 2,998,556, 3,120,532, 3,126,390, 3,139,434, 3,337,559, and 3,940,387. Analogs of yohimbic acid include yohimbine, 1-methylyohimbine, 10-hydroxyyohimbine, 11-hydroxy-yohimbine, 11-hydroxyyohimbine, 14-(4-nitrobenzoyloxy)yohimbine, 14-benzoyloxyyohimbine, 17-hydroxy-20-yohimban-16-(N-(4-azido-3-iodo)phenyl)carboxamide, 5-carboxytetrahydroalstonine, 9-methoxy-3-epi-alpha-yohimbine, raubasine, apoyohimbine, iodinated rauwolscine, NMI 187, rauwolscine 4-aminophenylcarboxamide, rauwolscine, Reserpine or an analog thereof (e.g., 16,18-reserpinediol, adelphan-esidrex, adelphane, aldatense, Bendigon, bietaserpine, Briserin, bromoreserpine, butiserpazide, caprinol, CD 3400, Crystepin CH, deserpidine, dibromoreserpine, enderpins, FH 109 C, Hyparez, meprocalm, methyl reserpate, Nortensin, Regroton, rescinamine, rescinnamine, reserpic acid, reserpine methonitrate, sinepres, and syrosingopine), and trimethoxybenzoylyohimbine.

Treatment of a Subject

The invention also provides methods for increasing cellular proliferation, enhancing skin repair or skin health, and promoting hair growth by administration of a compound that decreases expression or activity of p63 (e.g., dominant negative forms of p63, a p63 antibody, or a compound selected from the group consisting of acyclovir, alprostadil, aristolochic acid, carbadox, chlorpyrifos, cyclocreatine, 7,4'-dimethoxyisoflavone, dorzolamide, S(–)eticlopride, evoxine, guaifenesin, hydroxyprogesterone, kaempferol, linamarin, mexicanolide, MG 624, pramoxine, tannic acid, targinine, and yohimbic acid, or an analog thereof, to a subject in need thereof. The compounds can be further modified using standard chemical, physical, or biochemical methods.

Formulation of Pharmaceutical Compositions

The administration of any compound or composition described herein may be by any suitable means that results in a concentration of the compound that increases cellular proliferation, enhances skin repair or skin health, or promotes hair growth. The compound may be contained in any appropriate amount in any suitable carrier substance, and is generally present in an amount of 1-95% by weight of the total weight of the composition. The composition may be provided in a dosage form that is suitable for the oral, skin (e.g., topical or by patch), cutaneous, parenteral (e.g., intravenous or intramuscular), rectal, nasal, vaginal, inhalant, ocular, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

Pharmaceutical compositions may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agents of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the compound to a particular target cell type. Administration of the compound in the form of a controlled release formulation is especially preferred for compounds having a narrow absorption window in the gastro-intestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, molecular complexes, microspheres, nanoparticles, patches, and liposomes.

Topical Formulations

Pharmaceutical compositions according to the present invention can be formulated for topical administration. Subjects can be administered effective amounts of a compound described herein by means of a solution (e.g., drops), ointment, gel, or aerosol (e.g., nebulizer). The composition is typically administered to the affected area by topically applying, for example, one to four drops of a solution or suspension, or a comparable amount of an ointment, gel, or other solid or semisolid composition, once, twice, three times, or more than three times per day. These formulations can be made according to known and conventional methods for preparing such formulations.

For compounds of the invention that are not highly soluble in water at physiological conditions, a solubilizing excipient may be used to increase solubility. Solubilization is taken to mean an improvement in the solubility by virtue of surface-active compounds that can convert substances that are insoluble or virtually insoluble in water into clear, or opalescent, aqueous solutions without changing the chemical structure of these substances in the process. Excipients used for this purpose are restricted to those that are safe for administration to humans. Typically such co-solvents are employed at a level of about 0.01% to 2% by weight.

A variety of solubilizing excipients may be used for the formulation of a compound of the invention, including compounds belonging to the following classes: polyethoxylated fatty acids, PEG-fatty acid diesters, PEG-fatty acid mono-ester and di-ester mixtures, polyethylene glycol glycerol fatty acid esters, alcohol-oil transesterification products, polyglycerized fatty acids, propylene glycol fatty acid esters, mixtures of propylene glycol esters and glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, or ionic surfactants.

The compounds described herein can also be formulated as part a lotion such as a moisturizing lotion. Exemplary lotion formulations are described in U.S. Pat. Nos. 4,595,586; 4,459,285; 3,867,528; 3,265,571; 4,512,978; 4,564,462; 4,165,385; 3,062,721; 3,949,071; 4,482,537; 4,295,985; 2,507,236; and 3,987,775.

Solid Dosage Forms for Oral Use

Formulations for oral use include tablets containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or may be coated by known techniques, optionally to delay disintegration and absorption in the gastrointestinal tract and thereby providing a sustained action over a longer period. The coating may be adapted to release the compound in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols, and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes, (e.g., chemical degradation prior to the release of the active substances). The coating may be applied on the solid dosage form in a similar manner as that described in *Encyclopedia of Pharmaceutical Technology*, supra.

The compositions of the invention may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

Parenteral Compositions

A composition containing a compound described herein or identified using the methods of the invention may be administered parenterally by injection, infusion, or implantation (subcutaneous, intravenous, intramuscular, intraperitoneal, or the like) in dosage forms, formulations, or via suitable delivery devices or implants containing conventional, nontoxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Dosages

The dosage of any compound described herein depends on several factors, including: the administration method, the amount of increase in cellular proliferation, skin repair, hair growth, or skin health enhancement desired, and the age, weight, and health of the subject to be treated.

With respect to the treatment methods of the invention, it is not intended that the administration of a compound to a subject be limited to a particular mode of administration, dosage, or frequency of dosing; the present invention contemplates all modes of administration, including oral, cutaneous, subcutaneous, intramuscular, intravenous, intraperitoneal, intravesicular, intraarticular, intralesional, or any other route sufficient to provide a dose adequate to increase cellular proliferation, enhance skin repair or skin health, or promote hair growth treat. The compound may be administered to the subject in a single dose or in multiple doses. For example, a compound described herein may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compound. For example, the dosage of a compound can be increased if the lower dose does not provide sufficient activity in the treatment of a metabolic disorder (e.g., diabetes or obesity). Conversely, the dosage of the compound can be decreased if the metabolic disorder is reduced or eliminated.

While the attending physician ultimately will decide the appropriate amount and dosage regimen, a therapeutically effective amount of a compound described herein may be, for example, in the range of 0.0035 μg to 20 μg/kg body weight/day or 0.010 μg to 140 μg/kg body weight/week. Desirably a therapeutically effective amount is in the range of 0.025 μg to 10 μg/kg, for example, at least 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 μg/kg body weight administered daily, every other day, or twice a week. In addition, a therapeutically effective amount may be in the range of 0.05 μg to 20 μg/kg, for example, at least 0.05, 0.7, 0.15, 0.2, 1.0, 2.0, 3.0, 4.0, 5.0, 6.0, 7.0, 8.0, 10.0, 12.0, 14.0, 16.0, or 18.0 μg/kg body weight administered weekly, every other week, or once a month. Furthermore, a therapeutically effective amount of a compound may be, for example, in the range of 100 $\mu g/m^2$ to 100,000 $\mu g/m^2$ administered every other day, once weekly, or every other week. In a desirable embodiment, the therapeutically effective amount is in the range of 1000 $\mu g/m^2$ to 20,000 $\mu g/m^2$, for example, at least 1000, 1500, 4000, or 14,000 $\mu g/m^2$ of the compound administered daily, every other day, twice weekly, weekly, or every other week.

Example 1 p63 Inhibits Cellular Proliferation

Figure 1B:
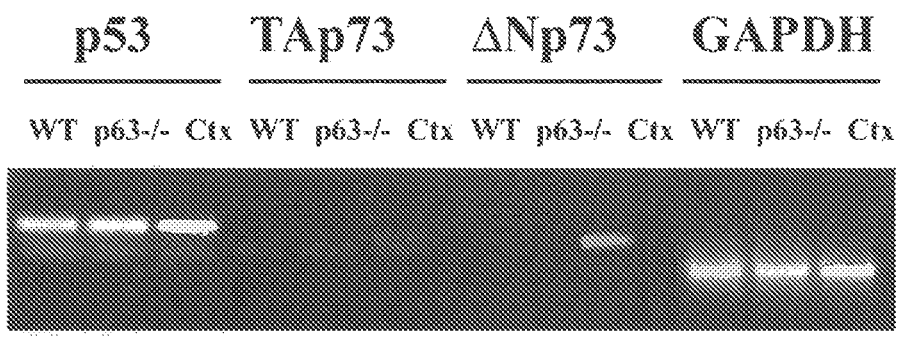
FIG. 1B is photograph of a gel showing that SKPs from both wild-type and p63 null mice express p53, but do not express p73. GAPDH is shown as a control.
Figure 1C:
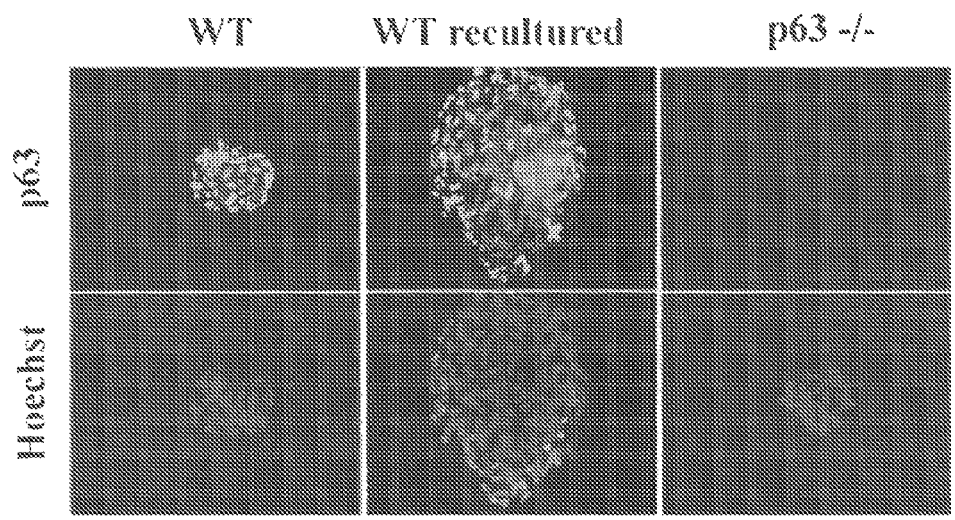
FIG. 1C is a set of photomicrographs showing that p63 is expressed in wild-type SKPs, but not in SKPs from p63 null mice (top panels). Hoescht stained cells are shown in the corresponding lower panels.

To determine whether there is a cell-autonomous requirement for tumor antigen p63 (TAp63) in the maintenance of dermal stem cells, we isolated and analyzed SKPs from wild-type and p63 null mice. We used RT-PCR to characterize the p53 family members expressed in cultured wild-type SKPs. Consistent with the expression of p63 in dermal sheath cells in vivo, SKPs expressed TAp63 mRNA, whereas p63 expression was not observed in cells taken from p63−/− mice (FIG. 1A). These cells did not express dominant negative p63 (dNp63) or p73, and p53 levels were similar in p63−/− and p63+/+ SKPs (FIG. 1B). Immunostaining with anti-p63 confirmed that wild-type, but not p63−/−, SKPs expressed detectable levels of p63 protein (FIG. 1C). Thus, of the p53 family members, SKPs express only TAp63 and p53.

Figure 1D:
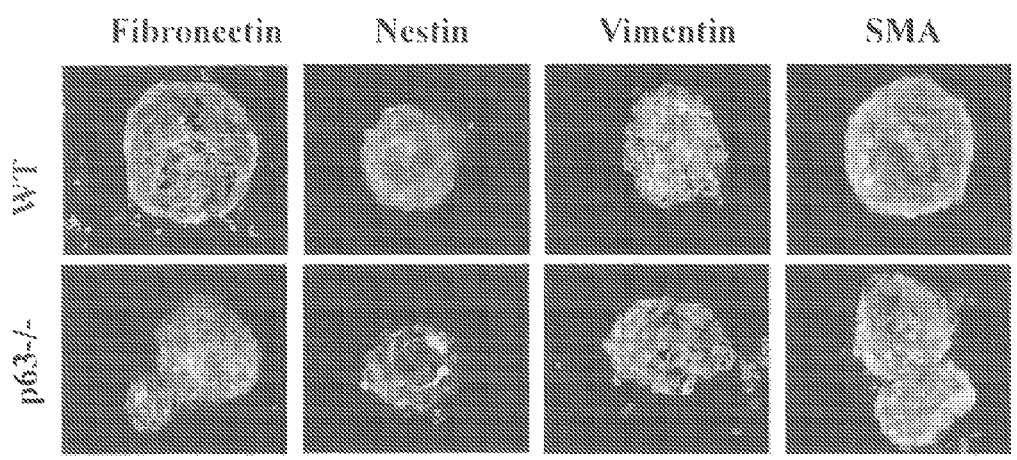
FIG. 1D is a set of photomicrographs showing that both SKPs from both wild-type and p63 null mice express the SKP markers fibronectin, nestin, vimentin, and SMA.
Figure 1E:
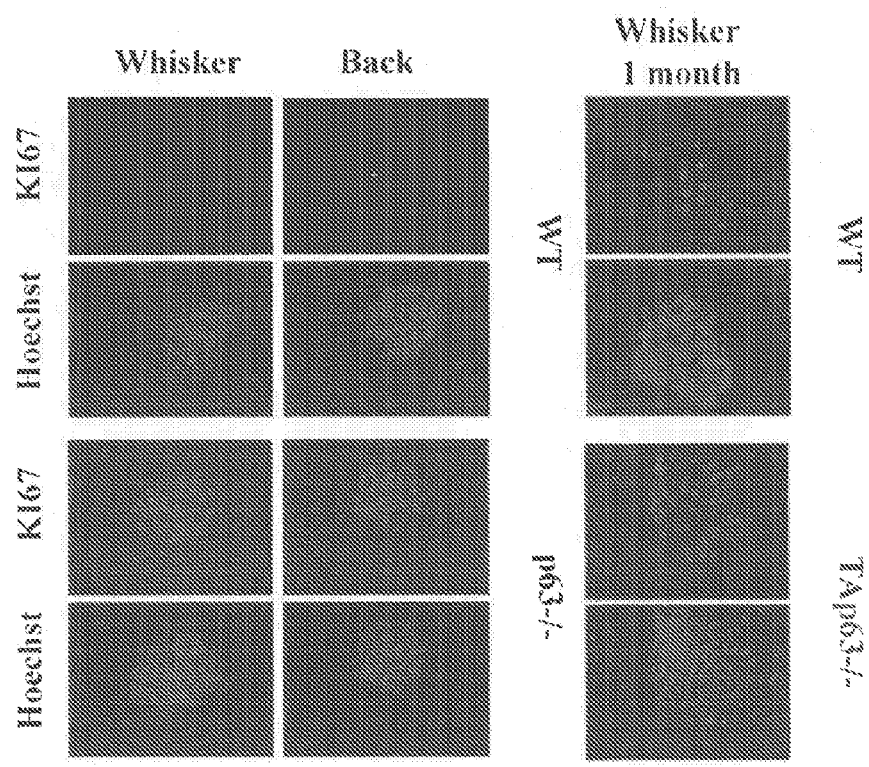
FIG. 1E is a set of photomicrographs showing that the proliferation marker Ki67 is expressed at higher levels in SKPs from p63 null mice than in wild-type SKPs. Results using whisker and back cells from neonatal mice, as well as using whisker cells from one-month-old mice, are shown.
Figure 1F:
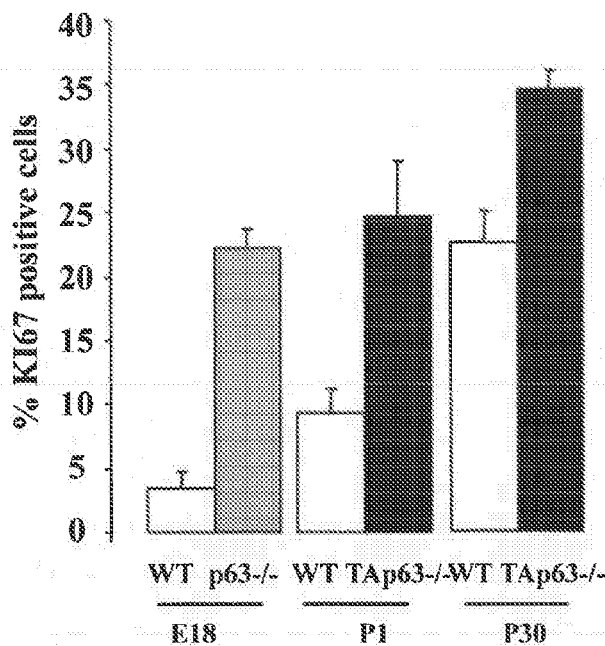
FIG. 1F is graph showing increasing Ki67 expression in p63 null mice as compared to wild-type mice in SKPs taken from E18, P1, and P30 mice.
Figure 1G:
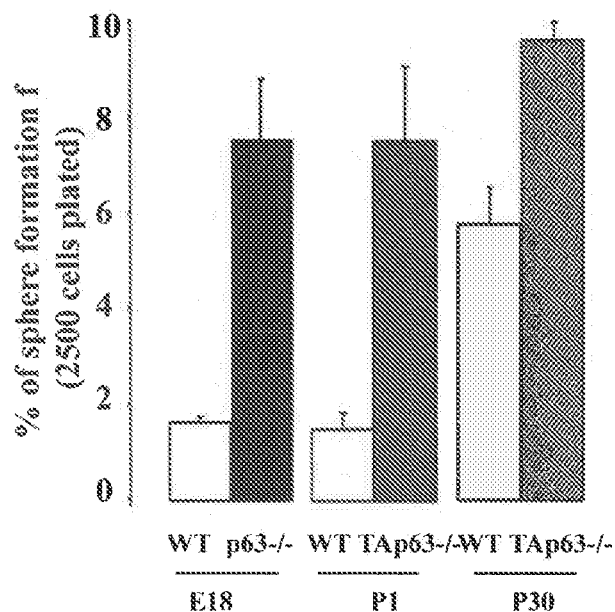
FIG. 1G is a graph showing that newborn TAp63−/− and E18 p63−/− SKPs self-renewed approximately 4 times more robustly than did wild-type SKPs and SKPs from one-month-old mice proliferated and self-renewed about 1.5 fold more than wild-type SKPs.
Figure 2A:
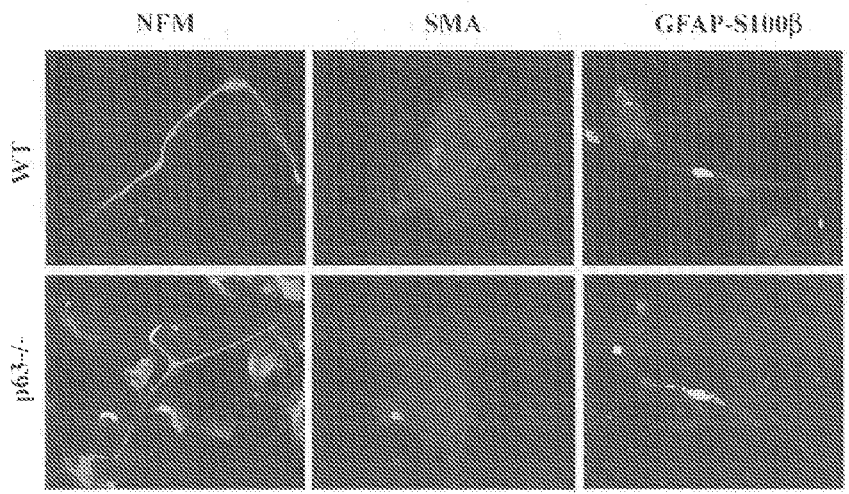
FIG. 2A is a set of photomicrographs showing that wild-type and p63−/− SKPs are capable of differentiating to neural and mesoderm subtypes. Left, neurofilament medium (NFM) expression; center, smooth muscle actin (SMA) expression; right, glial fibrillary acidic protein (GFAP) and S100β expression.
Figure 2B:
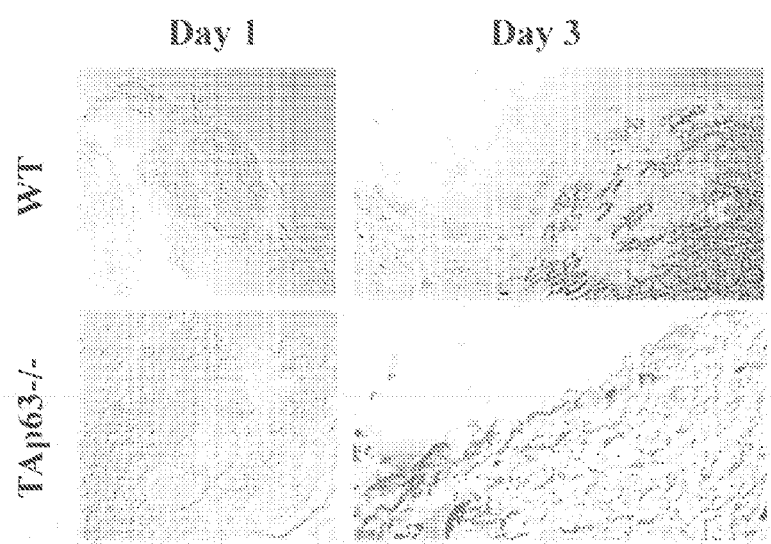
FIG. 2B is a set of photomicrographs showing that both wild-type and p63−/− SKPs, when transplanted into the neural crest migratory stream of HH stage 18 chicks in ovo, migrated into neural crest targets.

To determine whether TAp63 is necessary for maintenance of SKPs, the cells were isolated from the skin of TAp63−/− and TAp63+/+ mice at various times postnatally. Immunocytochemical analysis of SKP spheres for fibronectin, nestin, vimentin, and versican demonstrated that there were no overt differences in expression of these markers for SKPs with the loss of TAp63 (FIG. 1D). By contrast, immunostaining for the proliferation marker Ki67 demonstrated that TAp63−/− neonatal SKPs proliferated approximately 2-3-fold more than their wild-type counterparts. Similar results were obtained when SKPs were isolated from the rudimentary dermis that is present in E18 p63−/− mice (FIGS. 1E and 1F). To determine whether this increased proliferation reflected increased self-renewal, SKPs were dissociated to single cells, plated at low density in medium containing methylcellulose, and the percentage of cells that initiated a new sphere was determined. As seen in the proliferation assay, newborn TAp63−/− and E18 p63−/− SKPs self-renewed approximately 4 times more robustly than did wild type SKPs (FIG. 1G). When TAp63−/− SKPs were isolated from 1 month old mice, they still proliferated and self-renewed more than did wild-type SKPs, although the magnitude of the increase was reduced to approximately 1.5-fold (FIG. 1G). In spite of this hyperproliferation, TAp63−/− and TAp63+/+ SKPs were both able to differentiate into both neural and mesodermal cell types under previously defined conditions (FIG. 2A), and, when transplanted into the neural crest migratory stream of cHH stage 18 chicks in ovo, both populations of SKPs migrated into neural crest targets (FIG. 2B). Thus, TAp63 regulates SKP proliferation and self-renewal, but does not overtly affect their phenotype or differentiation capacity.

Figure 1H:
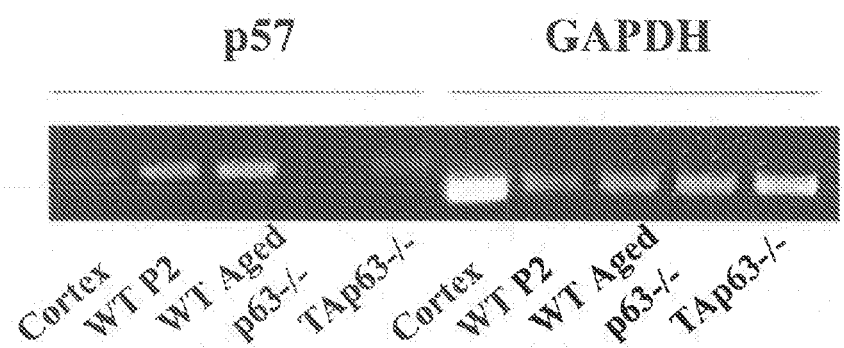
FIG. 1H is a photograph of a gel showing that the p57 mRNA expression is reduced in SKPs from p63 null mice as compare to those from wild-type mice.

Thus, TAp63 may normally function to dampen the self-renewal rate of SKPs, potentially as a mechanism to ensure that the SKPs last for the lifetime of the animal. One p63 target that decreases cellular proliferation is p57. RT-PCR analysis demonstrated that p57 mRNA levels were reduced in TAp63−/− and p63−/− SKPs (FIG. 1H). Immunocytochemistry for p57 confirmed this result, and demonstrated that p57 protein levels were decreased in SKPs in the absence of TAp63 (FIG. 1I) To confirm that p57 is a direct target of p63 in SKPs, as it is in human keratinocyte HaCat cell line (Beretta et al., Cell Cycle. 4:1625-1631, 2005), we performed chromatin immunoprecipitations using an antibody for p63. RT-PCR of the associated DNA demonstrated that p63 was bound to a previously defined binding site in the p57 promoter (FIG. 1J). Thus, TAp63 regulation of SKPs' self-renewal likely involves regulation of p57.

Figure 1I:
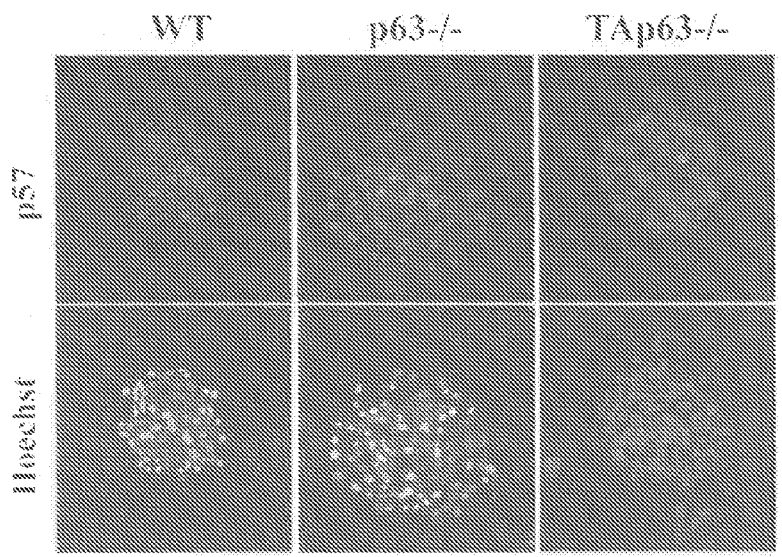
FIG. 1I is a set of photomicrographs showing p57 expression in wild-type, p63−/−, and TAp63−/− cells.
Figure 1J:
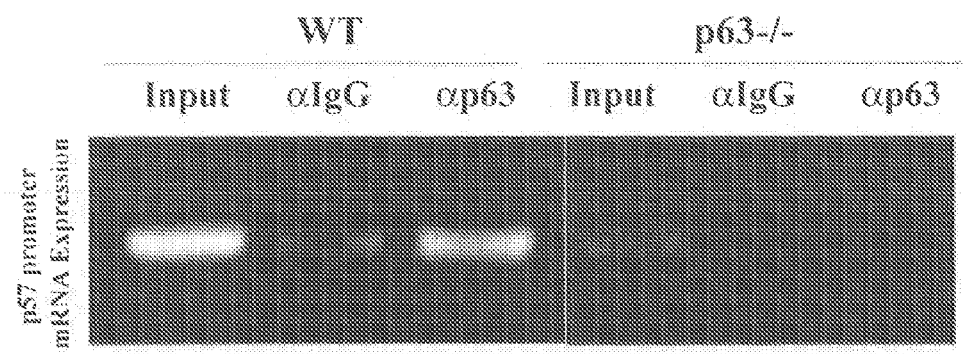
FIG. 1J is a photograph of a gel showing that, using RT-PCR, p63 is was bound to a previously defined binding site in the p57 promoter.
Figure 1K:
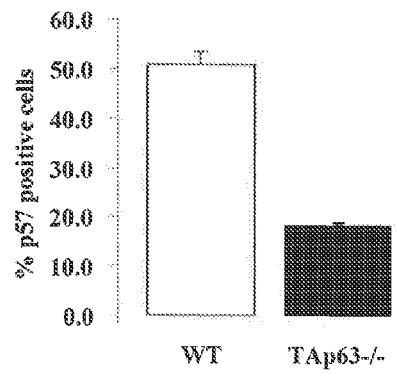
FIG. 1K is a graph showing the percentage of p57 positive cells in wild-type and in Tap63−/− cells.

To quantify the number of p57 positive cells in TAp63−/− cells and in wild-type cells, both types of cells were stained as shown in FIG. 1I, and the percentage of p57 positive cells was calculated. From these results, approximately 50% of the wild-type cells were identified as being p57 positive, whereas only 18% of the TAp63−/− cells were p57 positive (FIG. 1K).

Figure 1L:
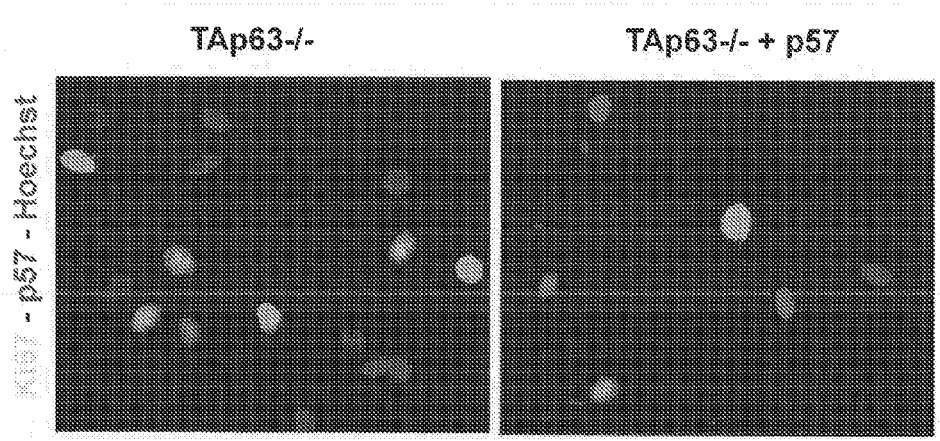
FIG. 1L is a set of photomicrographs showing immunostaining for p57Kip2 and Ki67 in TAp63−/− SKPs, plated on an adherent 4-well chamber slides, two days after transfection with or without a pCMV-p57Kip2 expression vector. Cells were counterstained with Hoechst 33258. Transfected p57-positive cells were never double-labelled for Ki67. The images are taken at 200× magnification with n=3 independent experiments.

We also determined whether the hyperproliferation phenotype in TAp63−/− SKPs could be rescued by p57Kip2 (p57). To do this, TAp63−/− SKPs were plated on an adherent substrate, transfected with either the empty vector or a p57Kip2 expression vector, and immunostained two days later for p57Kip2 and Ki67. Under these conditions, approximately 45% of TAp63−/− cells transfected with the empty vector were dividing, as monitored by Ki67 expression, and none of them expressed p57Kip2 (FIG. 1L). By contrast, approximately 20% of the cells transfected with p57Kip2 expressed detectable levels of this protein, and none of these transfected cells coexpressed Ki67 (FIG. 1L). Thus, p57Kip2 completely rescued the hyperproliferation, indicating that TAp63 regulates SKPs self-renewal at least in part by regulating p57Kip2.

Example 2

Screen for Compounds that Enhance Cellular Proliferation

Figure 3:
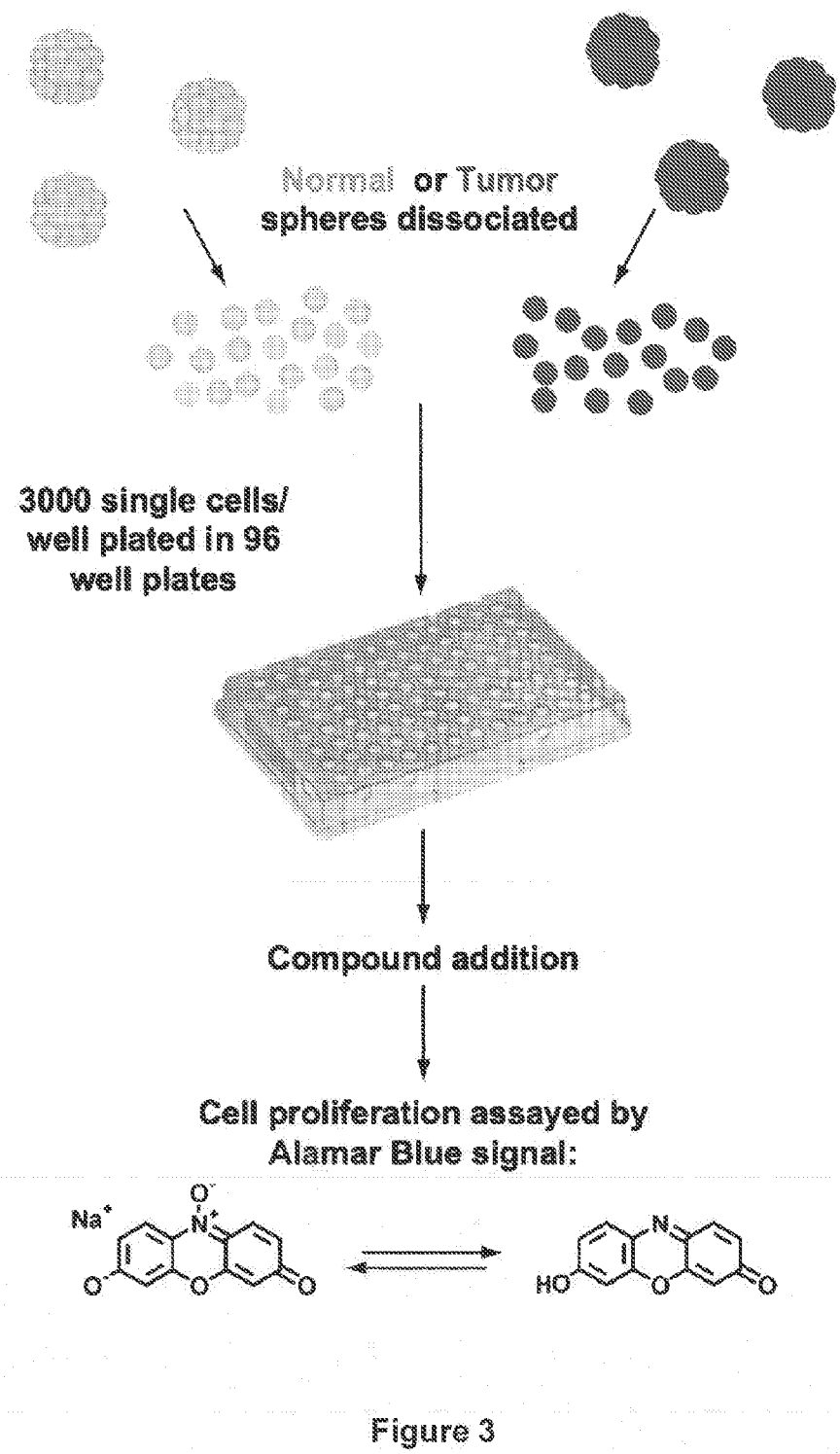
FIG. 3 is a schematic diagram of an exemplary screening procedure described herein.

To identify molecules (e.g., small molecules) that promote proliferation of SKPs, a simple, reproducible and robust assay that measures cell proliferation using Alamar Blue® dye, which yields a fluorescent signal in a response to metabolic activity, was developed. Compounds (5 μM) were added in singlet to 96-well uncoated plates, 3000 early passage dissociated sphere cells were robotically seeded, and plates were incubated in basal growth medium. After 30 hours, Alamar Blue was added and its reduction assessed after another 24 hours. Typically, there is an 8-10 fold difference in Alamar Blue reduction between positive and negative controls. A compound was identified as a hit if Alamar Blue reduction is increased by three standard deviations from the mean of all the compounds in a particular screen. In our assay, the variability of signals are low, with CV values ranging from 3.5-4.5% and the dimensionless statistical parameters Z' and Z factors>0.5, indicative of an excellent assay. The chemical libraries we used include the LOPAC, Prestwick, Biomol, and Spectrum collections, which comprise 3,500 unique low-molecular weight compounds, including both natural products and synthetic chemicals, known drugs and drug-like compounds, and phosphatase and kinase inhibitors. These screens were done at the same time as high-throughput screens using human neuroblastoma tumor cells with the goal of identifying drugs that are cytotoxic for cancer but not for normal cells (SKPs) (FIG. 3).

Using this screen, we identified several compounds that enhance the proliferation of human SKPs, shown in the Table below:

| | | |
|---|---|---|
| Acyclovir | Dorzolamide hydrochloride | Mexicanolide |
| Alprostadil | S(−)Eticlopride hydrochloride | MG 624 |
| Aristolochic acid | Evoxine | Pramoxine hydrochloride |
| Carbadox | Guaifenesin | Tannic acid |
| Chlorpyrifos | Hydroxyprogesterone | Targinine hydrochloride |
| Cyclocreatine | Kaempferol | Yohimbic acid |
| 7,4'-Dimethoxyisoflavone | Linamarin | |

Figures 4A, 4B, 4C:
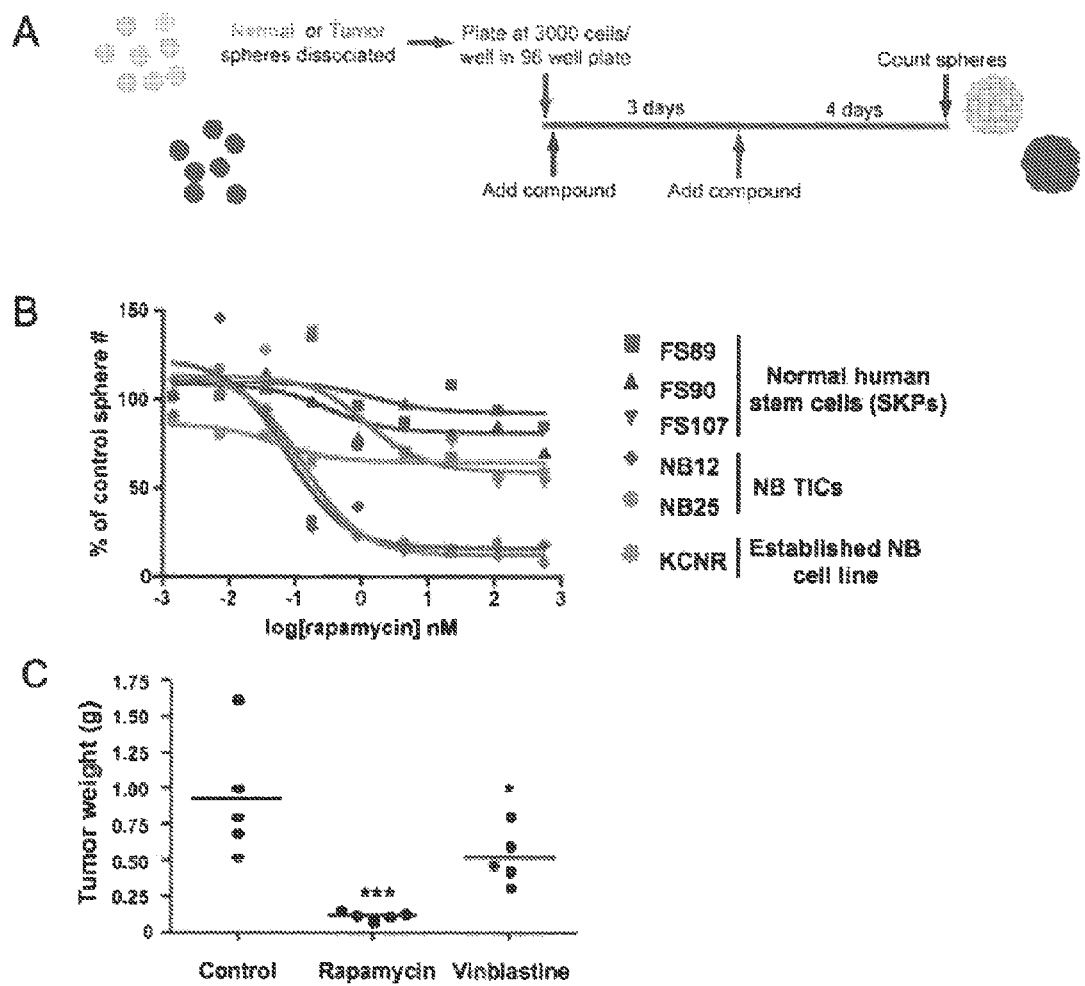
FIG. 4A shows a schematic diagram of the sphere formation assay employed to confirm the hits identified in the screen.
FIG. 4B is a graph showing the effects of increasing concentrations of rapamycin on sphere formation in various cell lines.
FIG. 4C is a graph showing inhibition of tumor formation by rapamycin and vinblastine.

To confirm these hits dose-response curves (IC50s) were determined using human neuroblastoma tumor cells in our standard Alamar Blue proliferation assay. In addition, we monitored proliferation over one week by quantifying cell numbers with trypan blue, and further, examined sphere formation over one week (as described in FIG. 4) with at least 3 independent human SKP cell isolates. The high-throughput screens with human neuroblastoma tumor cells identified several small molecules that are effective in inhibiting proliferation of multiple neuroblastoma patient samples in vitro and xenograft neuroblastoma tumors in vivo (FIG. 4).

Example 3

Characterization of MG 624

Figure 5:
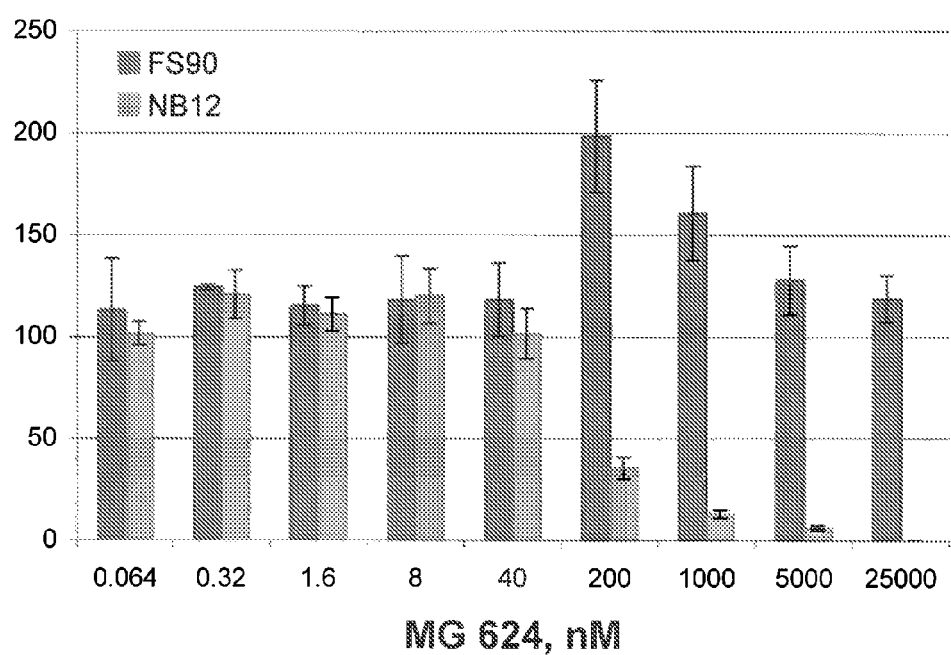
FIG. 5 is a graph showing the effects of MG 624 on SKPs (left) and neuroblastoma (right) proliferation at various concentrations. At 200 nM, SKP proliferation was increased.
Figures 6A, 6B, 6C:
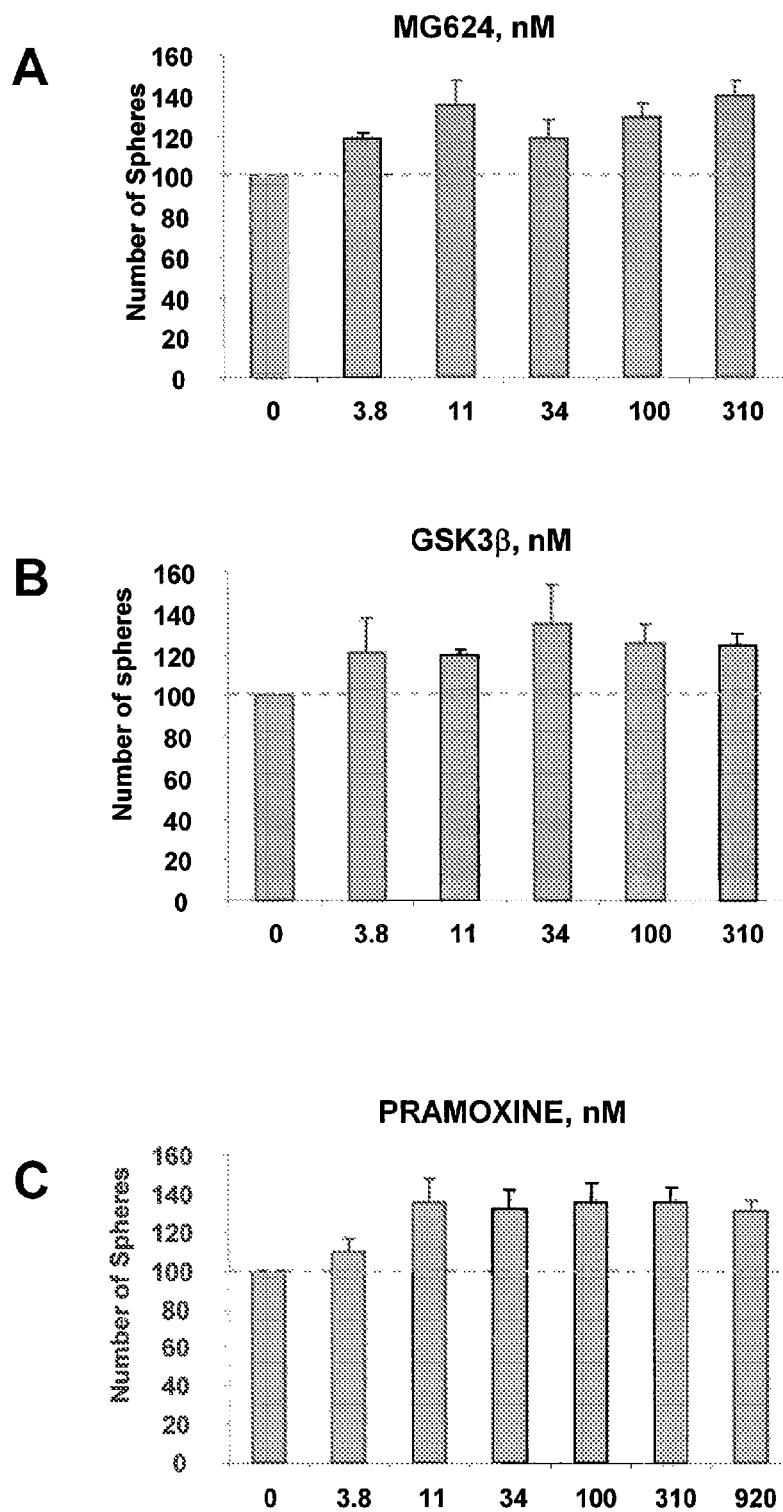
FIGS. 6A-6E are graphs showing dose-response curves for proliferation of human SKPs in response to MG624 (FIG. 6A), GSK3β (FIG. 6B), pramoxine (FIG. 6C), kaempferol (FIG. 6D), and alprostadil (FIG. 6E) in presence of EGF and FGF2.
Figure 6D:
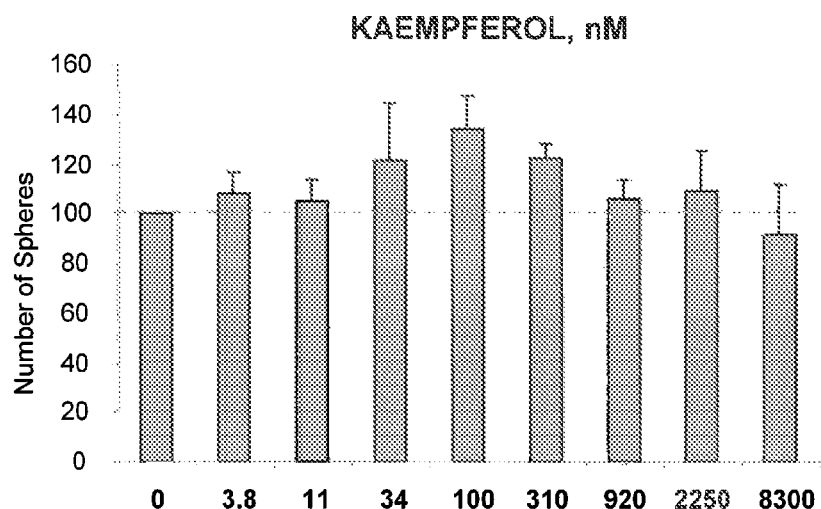
Figure 6E:
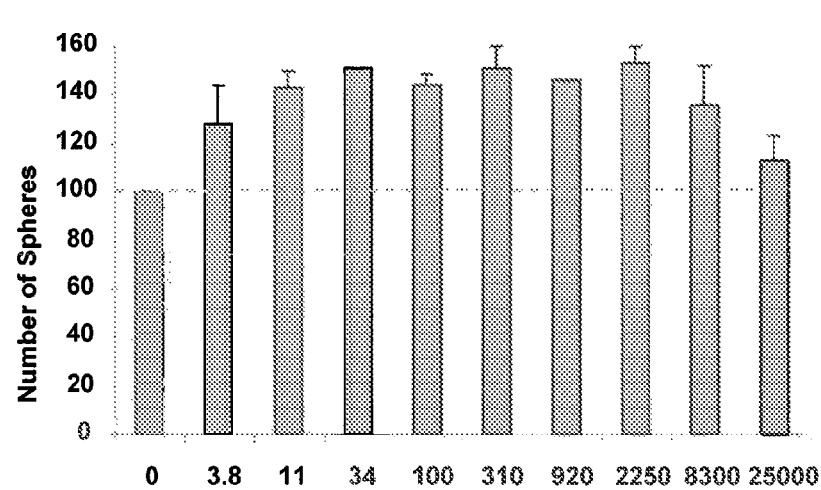

The proliferative effects of MG 624 on SKPs and neuroblastoma tumor initiating cells have also been studied in detail. Dose response curves for proliferation of human SKPs and neuroblastoma tumor initiating cells in response to MG 624 were generated in the presence of EGF and FGF2. At 200 nM MG 624, SKP cell proliferation is enhanced (FIG. 5).

Example 4

Dose-Response for Proliferation of Human SKPs

To characterize enhancement of proliferation brought about by the agents identified above, dose-response curves for MG624, GSK3β, pramoxine, kaempferol, and alprostadil in presence of EGF and FGF2 were generated (FIGS. 6A-6E). In all cases, enhanced proliferation at 100 nM concentration of each agent was observed as compared to cells grown in the absence of the agent.

Example 5

Figure 7:
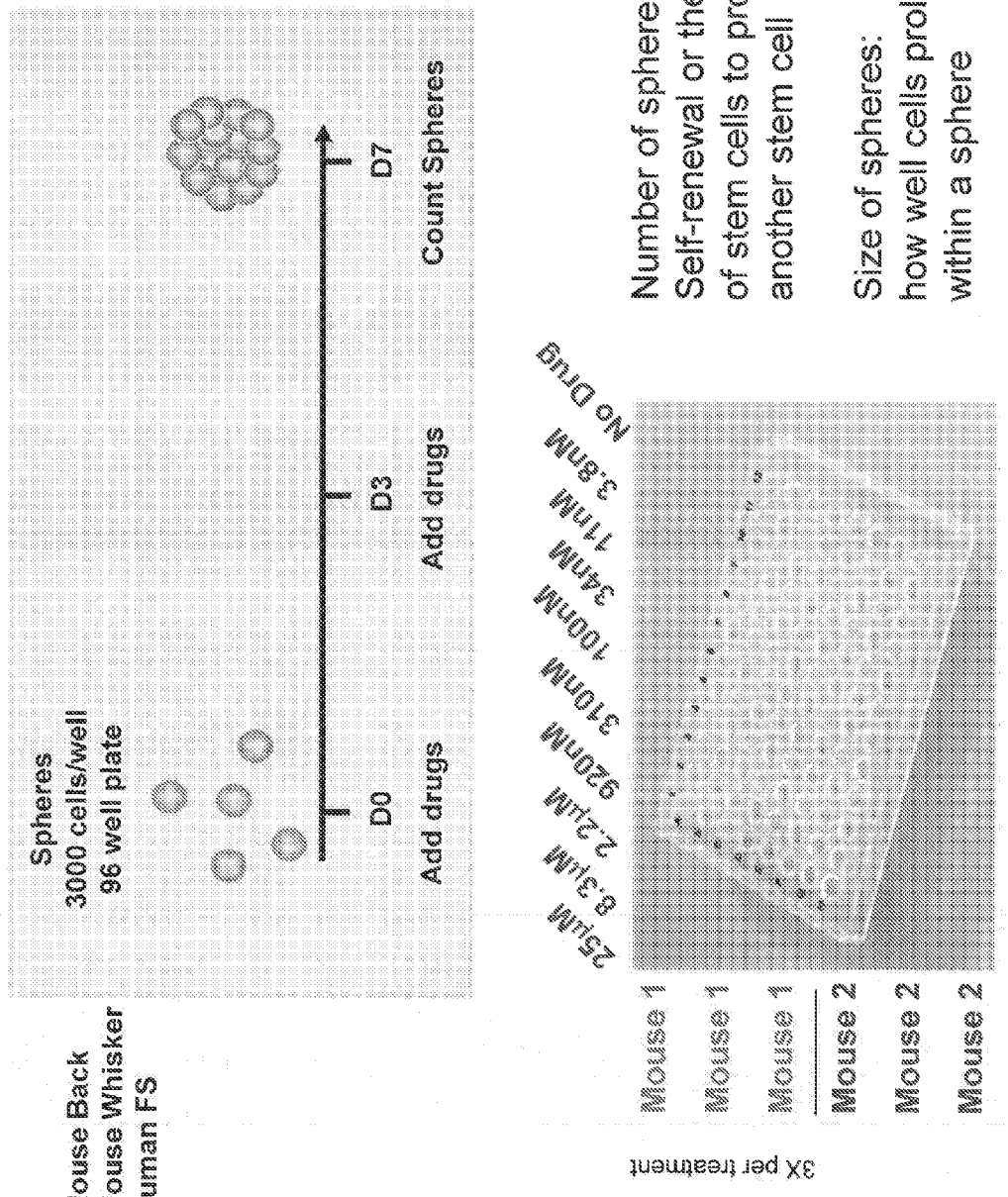
FIG. 7 is a schematic illustration of the in vitro sphere assay. SKPs were isolated from mouse back, whisker and human foreskin and allowed to grow in spheres. After 2-3 passages, spheres were dissociated and 3000 cells were plated in each well of a 96-well plate. Cells were then treated in triplicate with different concentrations of drugs or only with vehicle DMSO. Drugs were applied again on day 3 and the number of spheres was analyzed on day 7.

Assays Demonstrating that Certain Compounds can Induce Proliferation of Human and Mouse SKPs FIG. 7 is a schematic presentation of an in vitro sphere assay employed to demonstrate the ability of compounds to promote proliferation of human and mouse SKPs we performed a secondary drug screen. SKPs were isolated from mouse back, whisker, and human foreskin and allowed to grow in spheres. After 2-3 passages, spheres were dissociated and 3000 cells were plated in each well of a 96 well plate. Cells were then treated in triplicate with different concentrations of drugs or with vehicle (DMSO) only. Drugs were applied again on day 3 and number of spheres was analyzed on day 7.

Figure 8:
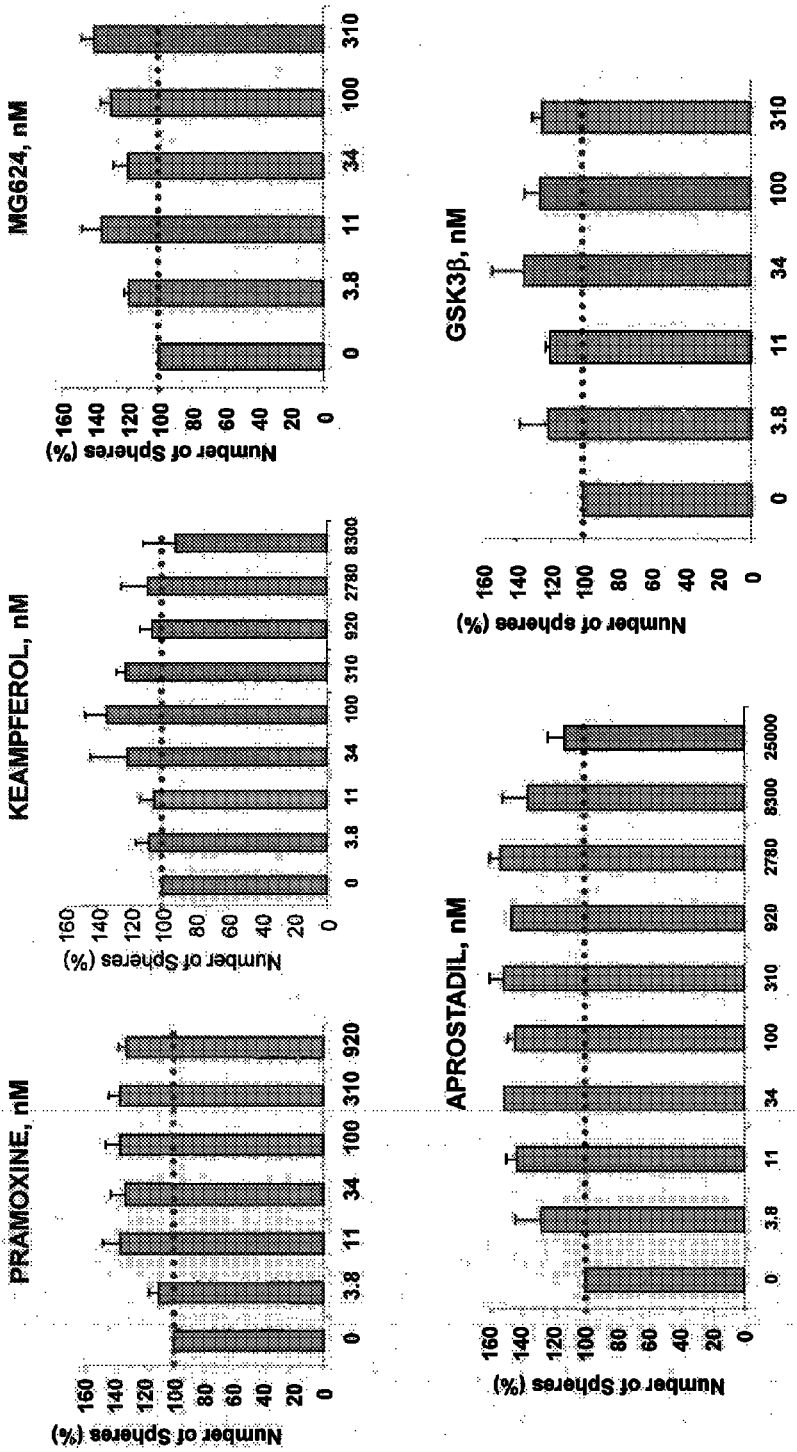
FIG. 8 is a series of graphs showing that various compounds promote human SKPs self-renewal. Graphs show pooled data from two set of experiments. Four different cell lines were used.

FIG. 8 depicts quantification of the percentage of spheres formed after treatments of human SKPs with different concentration of drugs. The sphere assay was performed on human SKPs treated with specific drugs or vehicle for 7 days, as described above. Certain compounds promoted human SKPs self-renewal in a dose-response manner. The graphs show pooled data from two set of experiments, in which four different cell lines were used.

Figure 9:
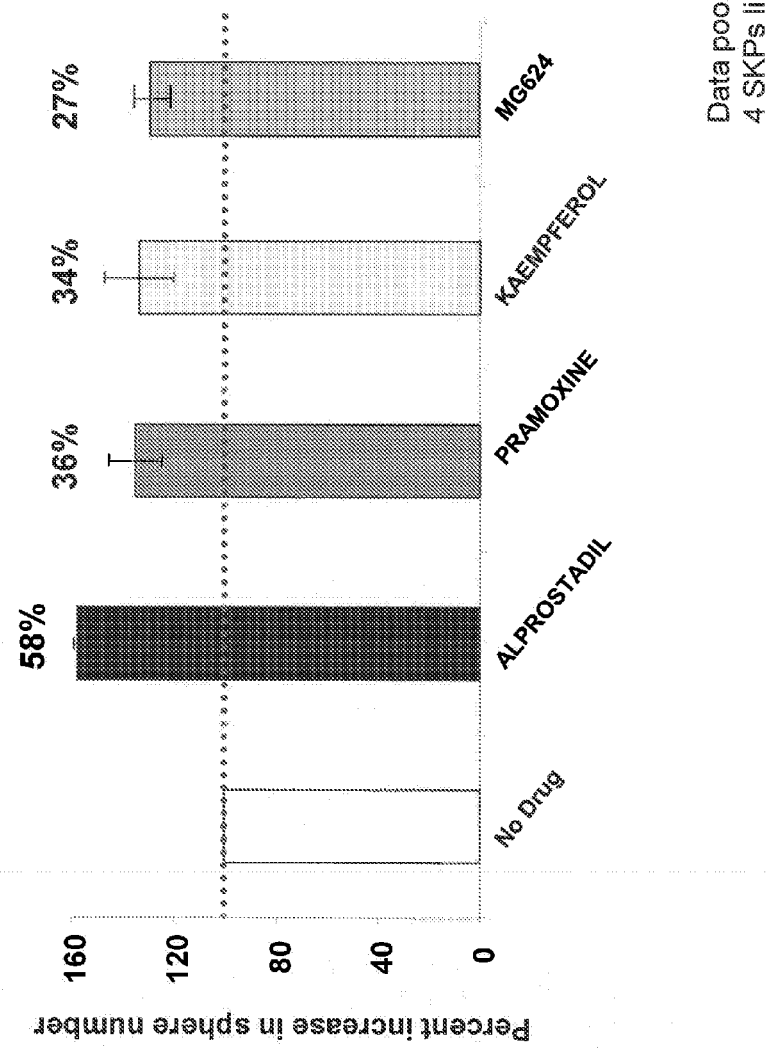
FIG. 9 is a graph showing that various compounds at 100 nM promote human SKPs self-renewal. Pooled data from two different experiments show robust increase of the number of spheres formed after drug treatments at 100 nM. Results indicate that these specific drugs promote the ability of stem cells to produce another stem cell.

FIG. 9 is a graph that shows that compounds at 100 nM promote human SKPs self-renewal. Pooled data from two different experiments show robust increase of the number of spheres formed after drug treatments at 100 nM. The results indicate that these compounds promote the ability of stem cells to produce another stem cell.

Figure 10:
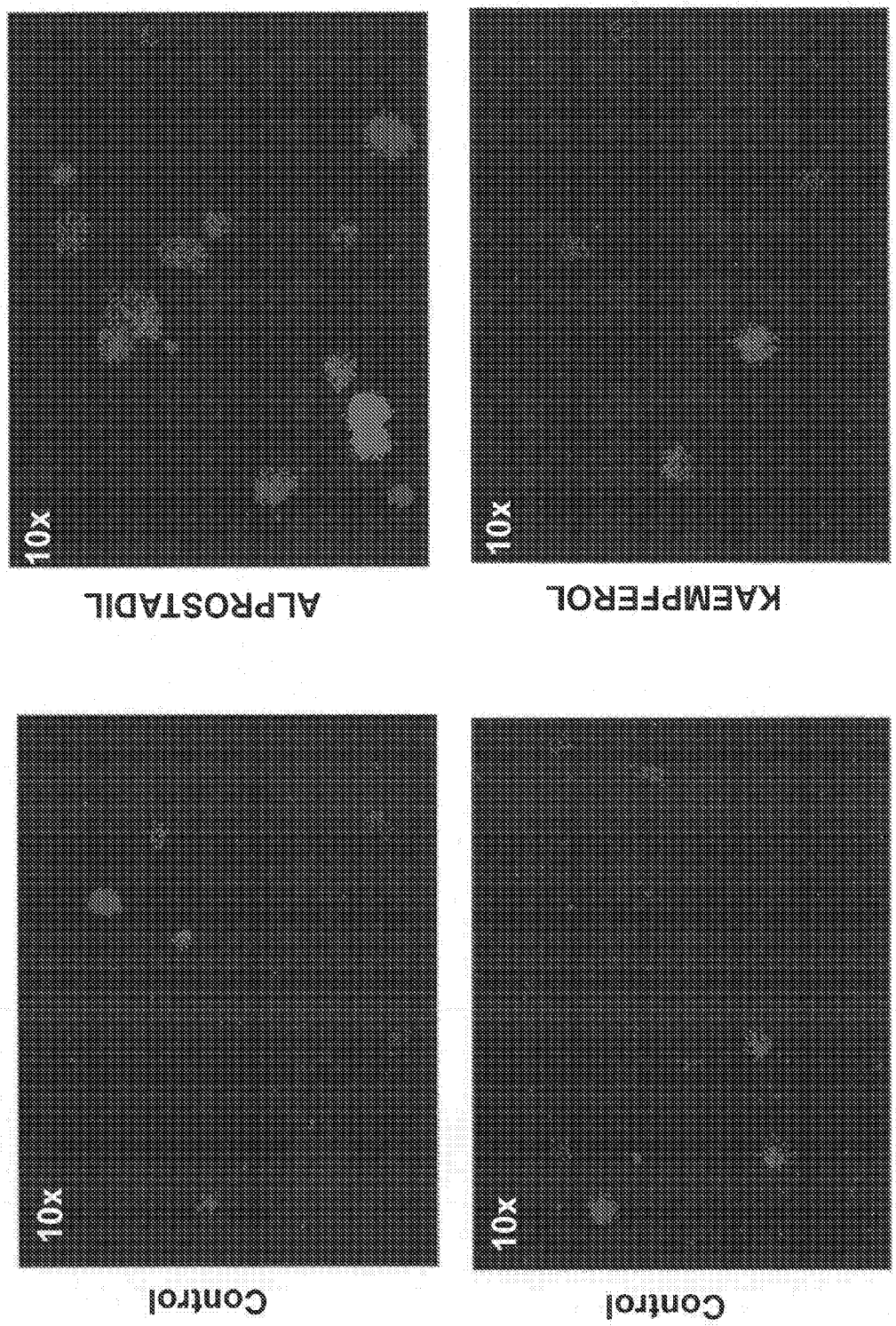
FIG. 10 is a series of photomicrographs showing that alprostadil and kaempferol increase the size of human SKP spheres. Human SKPs were treated with the indicated compound or vehicle for seven days, as indicated in FIG. 7. At the end of the treatment period, cells were stained with Hoechst. An increase in the size of the spheres was observed in the alprostadil- and kaempferol-treated cells compared to vehicle control, indicating that these drugs increase cell proliferation within a sphere.
Figure 11:
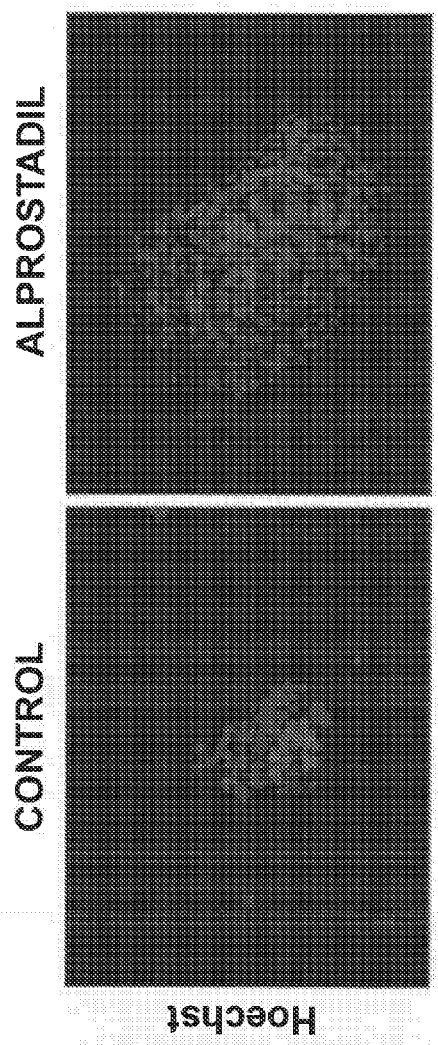
FIG. 11 is a series of photomicrographs of human SKP spheres formed after 7 days of treatment with alprostadil or vehicle respectively.

FIGS. 10 and 11 are each a series of photographs showing that alprostadil and kaempferol increase the size of spheres. Human SKPs were treated with the indicated compound or vehicle for seven days, as described above. At the end of the treatment period, cells were stained with Hoechst. An increase in the size of the spheres was observed in the alprostadil- and kaempferol-treated cells compared to vehicle control, indicating that these drugs increase cell proliferation within a sphere.

Figure 12:
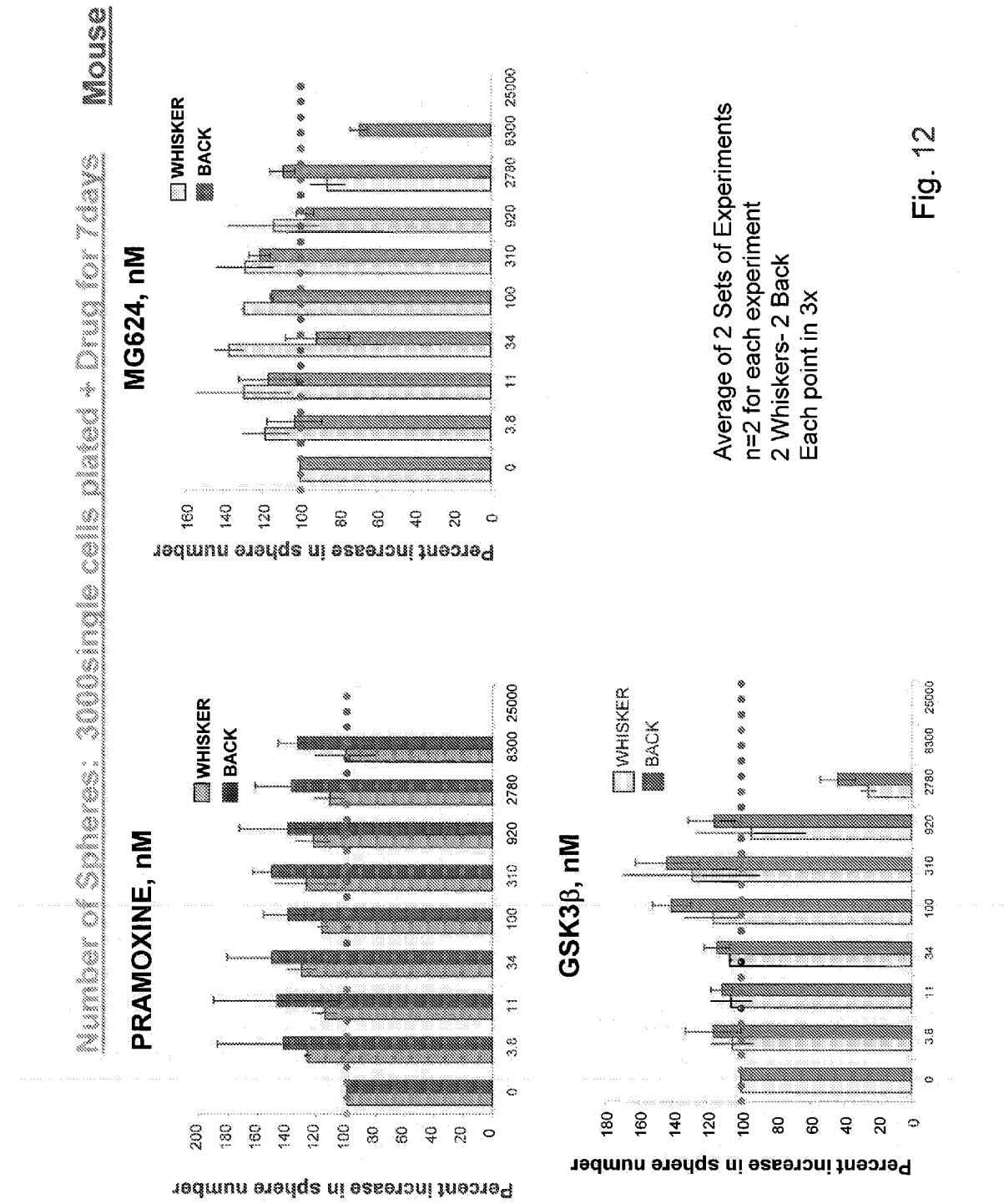
FIG. 12 is a series of graphs showing that various compounds that promote self-renewal of human SKPs also function on mouse SKPs. SKPs were isolated from mouse back and whisker and treated with the indicated concentration of drugs. Results are pooled data from two experiments. A total of four whisker and four back samples were used.
Figure 13:
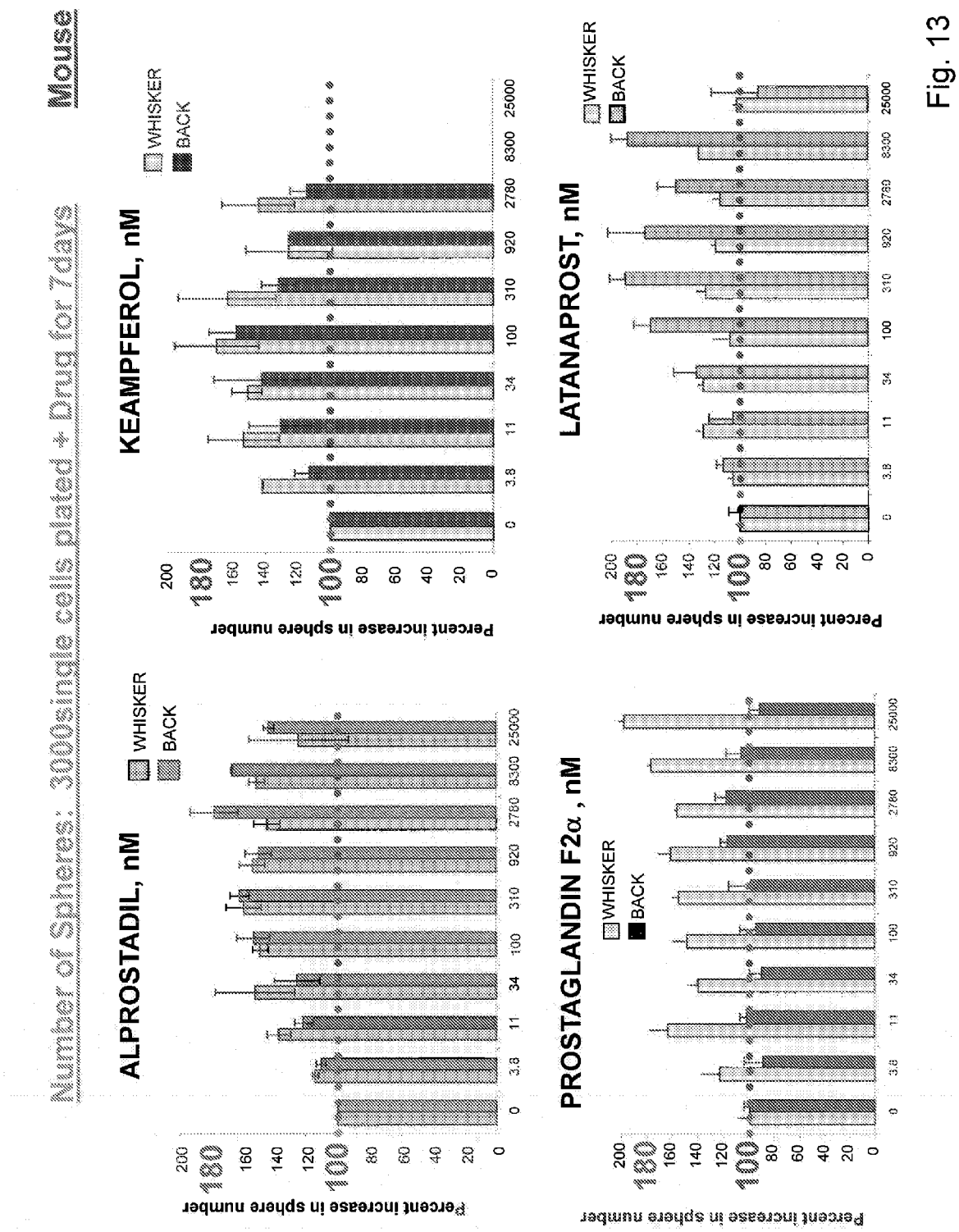
FIG. 13 is a series of graphs showing that various compounds promote self-renewal of mouse SKPs.

FIGS. 12 and 13 are each a series of graphs showing that certain compounds that promote self-renewal of human SKPs also function on mouse SKPs. SKPs were isolated from mouse back and whisker and treated with different concentration of the indicated compounds. The results are pooled data from two experiments. A total of four whisker and four back samples were used.

Figure 14:
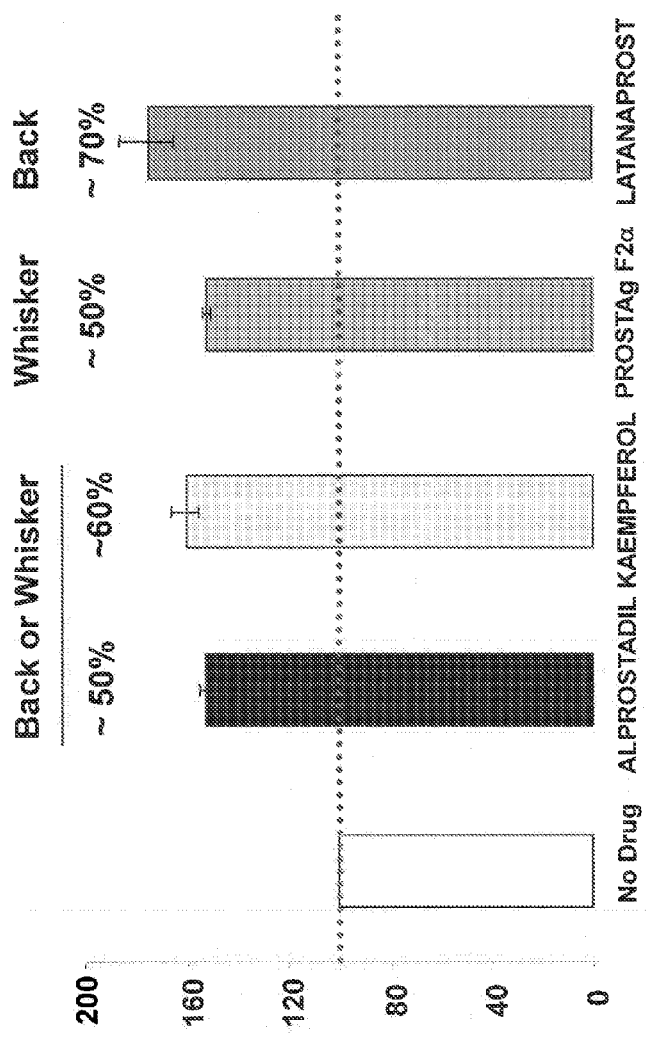
FIG. 14 is a graph showing that various compounds at 100 nM promote mouse SKPs self-renewal. Pooled data from two experiments show robust increase of the number of spheres formed for both back and whisker cells after drug treatment.

FIG. 14 is a graph showing that certain compounds at 100 nM promote mouse SKPs self-renewal. Pooled data from two experiments show robust increase of the number of spheres formed for both back and whisker cells after drug treatments at 100 nM.

Figure 15:
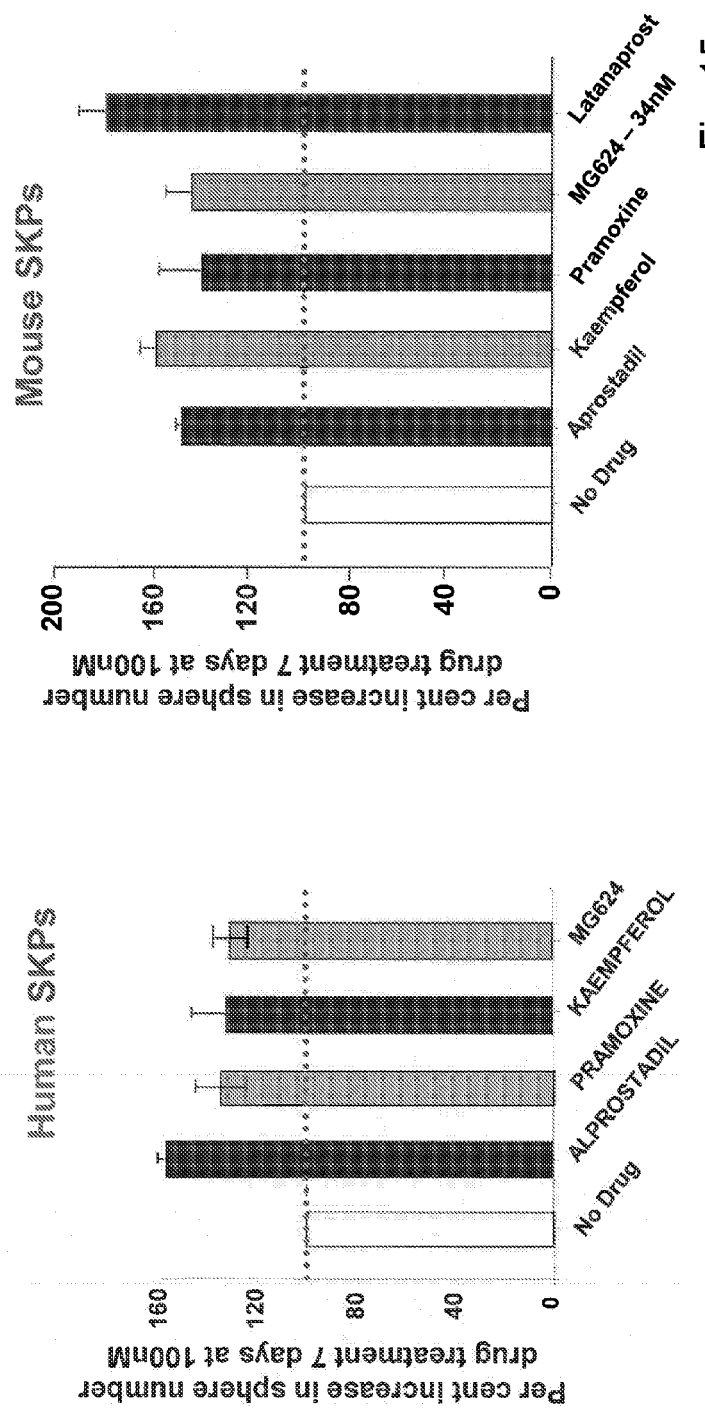
FIG. 15 is a series of graphs summarizing in vitro sphere assay data demonstrating that certain compounds promote self-renewal of both human and mouse SKPs.

FIG. 15 is a series of graphs that summarize the in vitro sphere assay data.

Example 6

Assays Demonstrating that Topical Application of Certain Compounds Induces Anagen Hair Cycle and Greater Follicle Density We tested compounds to determine whether their topical application could induce anagen hair cycle and follicle density. Briefly, seven-week old C57BL/6 mice were used. Their dorsal skin was pinkish in color, indicating that the hair was in telogen (resting) phase. Mice were induced to enter anagen phase by being depilated in the dorsal region. Compounds (100 mL) were topically applied onto the dorsal skin once daily for 3 weeks. Three mice were used for each compound group. Approximately 30 hairs from each mouse were plucked at specific days (day 16, day 19, and day 23) and the hair length was measured. Additionally, skin samples for cryosectioning were obtained from the treated dorsal region of each mouse.

All compounds were resuspended in vehicle solution (1.2 propanediol:EtOH:H20 (40:20:40)). Compound concentrations were as follows: alprostadil 40 μg/mL; kaempferol 28.6 μg/mL; pramoxine 329.8 μg/mL; MG 624 45.13 μg/mL. Also tested was Gold Bond topical anesthetic cream. Latanoprost (150 μg/mL) was used as a positive control and AKT inhibitor A443654 (100 μM) was used as a negative control.

FIG. 16 is a table showing that topical application of certain compounds promote hair growth. Mice were treated topically with compounds described above. At specific time points, approximately 30-40 hairs were plucked from each mouse and their length was measured. Three mice were used to test each compound.

Figure 17:
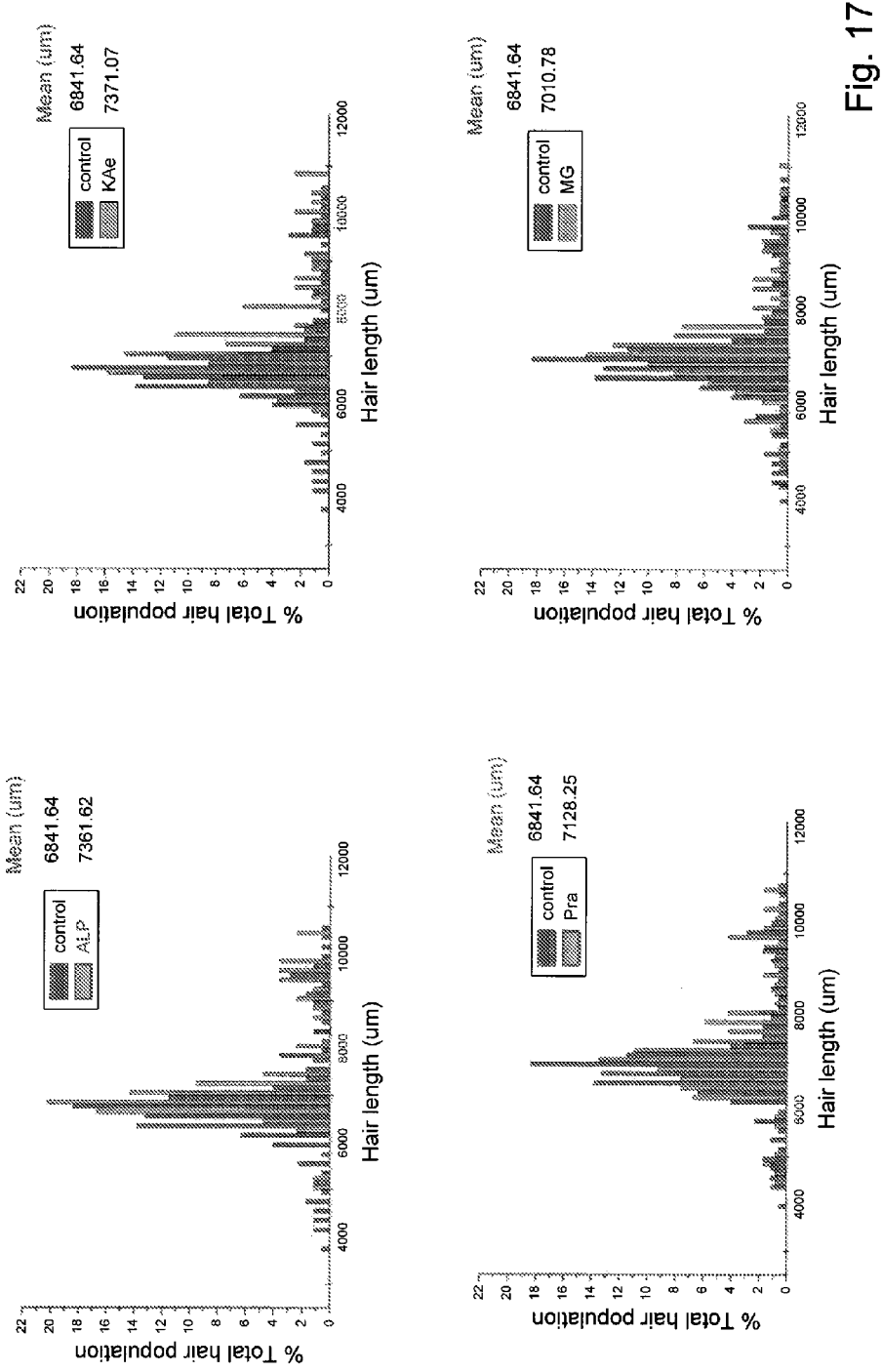
FIGS. 17 and 18 are each a series of graphs showing quantification of hair length on day 23. Hair length promoted by compounds is shown in distribution histograms relative to the control group. Hair length was binned in classes of 200 μm and each class was expressed as a percentage of total hair population. The distribution histograms show a shift versus longer hair length, particularly in the groups treated with alprostadil or kaempferol.
Figure 18:
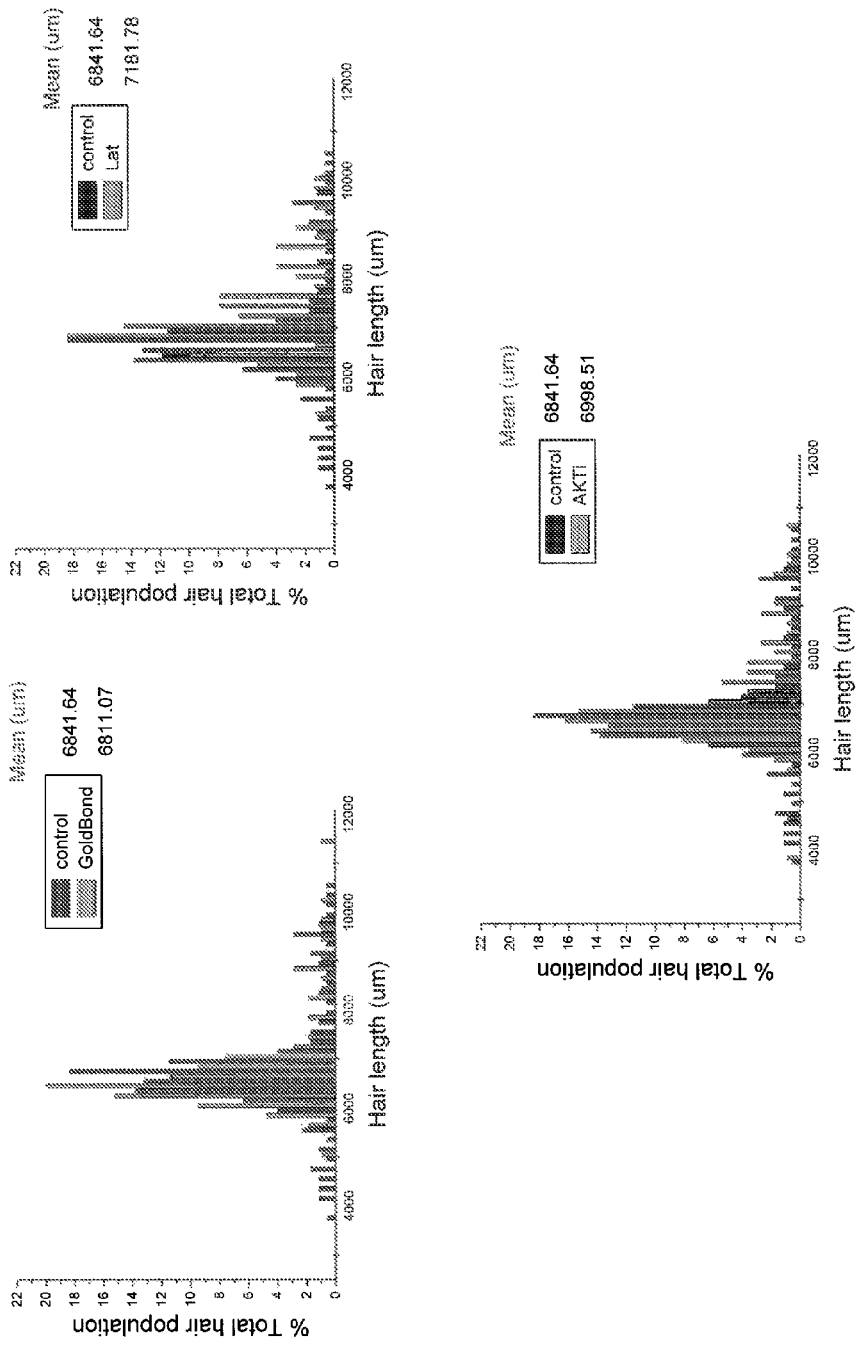

FIGS. 17 and 18 are each a series of graphs showing quantification of hair length on day 23. Hair length promoted by compounds is shown in distribution histograms relative to the control group. Hair length was binned in classes of 200 μm and each class was expressed as a percentage of total hair population. The distribution histograms show a shift versus longer hair length, particularly in the groups treated with alprostadil or kaempferol.

Figure 19:
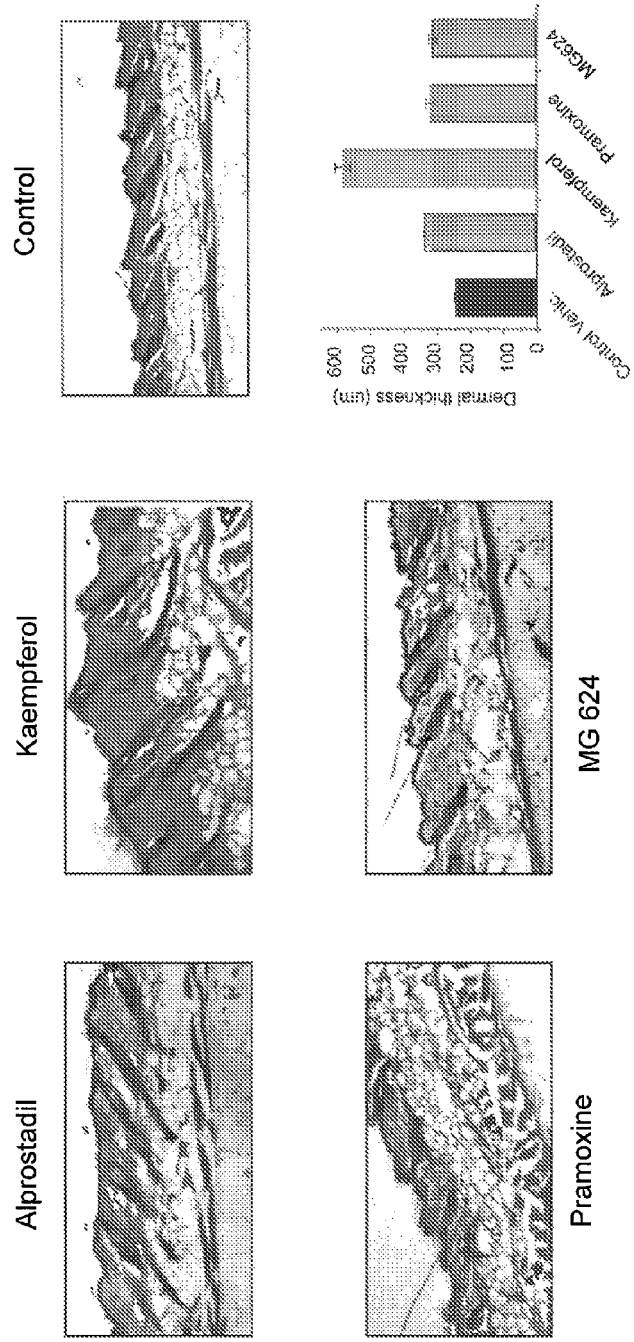
FIG. 19 is a series of photomicrographs and graphs showing that topical application of certain compounds induces dermal thickness. Dorsal skin of animals topically treated with various compounds was isolated, cryosectioned, and stained with hematoxylin and eosin. Dermal thickness was manually measured randomly through the slices. A mean of three measurements through the slice were performed and about 20-30 slices were analyzed for each mouse within each compound group.

FIG. 19 is a series of photomicrographs and graphs showing that topical application of the indicated compounds induces dermal thickness. Dorsal skin of animals topically treated with compounds described above, then isolated, cryosectioned and stained with hematoxylin and eosin. Dermal thickness was manually measured randomly through the slices. A mean of three measurements through the slice were performed and about 20-30 slices were analyzed for each mouse within each compound group.

FIG. 20 is a series of photomicrographs and graphs showing that alprostadil, kaempferol, pramoxine, or MG 624 induces anagen hair cycle and follicle density. The density is expressed as number of follicles per mm whereas the anagen hair follicles are determined by morphology.

Example 7

Combinations of Compounds for Inducing Anagen Hair Cycle and Greater Follicle Density The use of combinations of compounds for inducing anagen hair cycle and greater follicle density is also an aspect of the invention. Any combination of two or more compounds described herein can be used for this purpose, including alprostadil and kaempferol; alprostadil and pramoxine; kaempferol and pramoxine; alprostadil and MG 624; kaempferol and MG 624; and pramoxine and MG 624.

Figure 21:
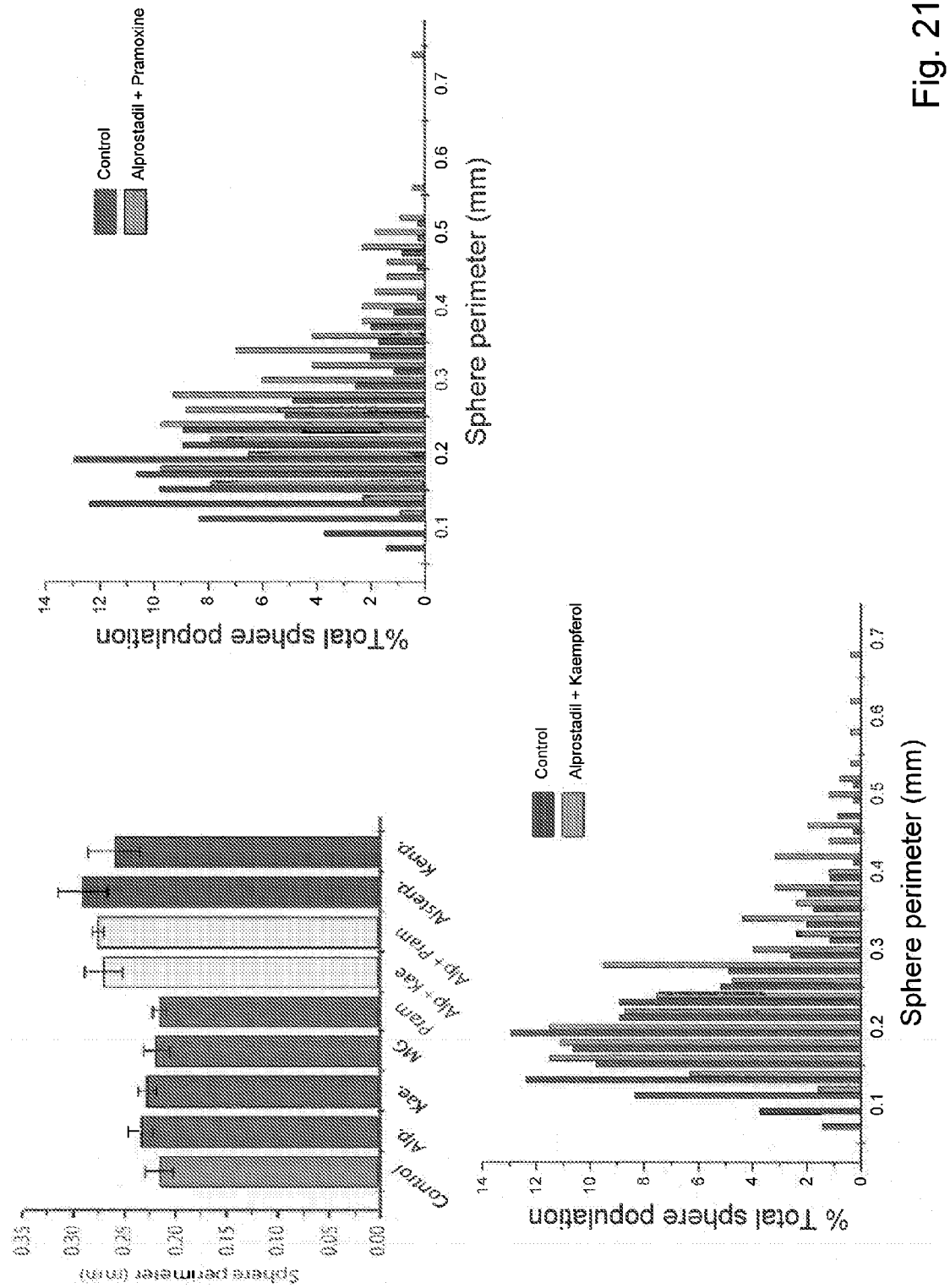
FIG. 21 is a series of graphs showing the effect of certain compounds and compound combinations on human SKP sphere size in vitro. The first graph (left, top) shows mean sphere size following treatment with the indicated compounds, compound combinations, or a DMSO control. The other two graphs are histograms showing the shift in human SKP sphere size when treated by alprostadil and pramoxine (right, top) or alprostadil and kaempferol (left, bottom). Alp.=alprostadil; Kae.=Kaempferol; MG=MG 624; Pram=pramoxine; Alsterp.=alsterpaullone; Kenp.=kenpaullone.

Combinations of (a) alprostadil and kaempferol and (b) alprostadil and pramoxine were demonstrated to increase SKP sphere size in vitro more effectively than single agents or a DMSO control (FIG. 21). Sphere size is corrected with, and is thus a measure of, cell proliferation. SKPs were isolated from human foreskin and allowed to grow in spheres. After 2-3 passages, spheres were dissociated and 3000 cells were plated in each well of a 96 well plate. Cells were then treated in triplicate with (a) 100 nM of a single drug, (b) a combination of drugs in which each drug is present at a concentration of 100 nM, or (c) vehicle (DMSO). Drugs were applied again on day 3. To assess how well cells proliferate within the sphere, the size of spheres was analyzed on day 7. Positive controls are kenpaullone, an inhibitor of GSK3β, and alsterpaullone, an inhibitor of GSK3β, CDK5/p25, and CDK1/cyclin B.

Sphere size in the presence of either (a) alprostadil and kaempferol or (b) alprostadil and pramoxine is shown in distribution histograms relative to the control group (FIG. 21). Sphere size was binned in classes of 20 μm, and each class was expressed as a percentage of total sphere population. The distribution histograms of the compound combinations show a shift to bigger sphere sizes in the presence of the drugs as compared to the control samples.

Example 8

Single Agent In Vivo Data

The efficacy of alprostadil and kaempferol in increasing length of hair growth in mice has been demonstrated. Sox2-EGFP mice, 7-8 weeks old, were shaved on the dorsal back to synchronize the hair cycle, and kaempferol (Kae) or alprostadil (Alp) was topically applied daily. Control mice were treated with vehicle only. At days 16, 19, and 23, about 30-40 hairs were plucked from each mouse, and their length was measured. Three or four mice were used in each group. An increase in hair length is observed in the alprostadil- and kaempferol-treated mice as compared to control mice (FIG. 22A). Hair length promoted by the compounds on day 23 is shown in distribution histograms relative to the control group. Hair length was binned in classes of 200 μm, and each class was expressed as a percentage of total hair population. The distribution histograms show a shift to longer hair lengths in the groups treated with kaempferol (FIG. 22B) and alprostadil (FIG. 22C), as compared to the control mice.

Other Embodiments

All patents, patent applications, and publications mentioned in this specification are herein incorporated by reference, including U.S. Provisional Application No. 61/101,443, filed Sep. 30, 2008, and International Application No. PCT/US2009/058723, filed Sep. 29, 2009, to the same extent as if each independent patent, patent application, or publication was specifically and individually indicated to be incorporated by reference.

What is claimed is:

1. A method of increasing proliferation of skin-derived precursors (SKPs), said method comprising
   culturing SKPs in vitro in medium containing FGF2 or EGF and
   contacting said SKPs in vitro with a sufficient amount of a compound to increase proliferation of SKPs, wherein the compound is selected from the group consisting of alprostadil, kaempferol, and MG 624,
   wherein the contacting is carried out under conditions that support cell proliferation and result in growth of said SKPs as spheres.

2. The method of claim 1, wherein said cell culture further comprises an additional growth factor.

3. The method of claim 1, wherein the compounds are alprostadil and kaempferol.

4. The method of claim 1, wherein the compound is alprostadil and wherein the SKPs are contacted simultaneously with alprostadil and pramoxine.

* * * * *